(12) United States Patent
Palladino et al.

(10) Patent No.: US 7,119,223 B2
(45) Date of Patent: *Oct. 10, 2006

(54) INTERLEUKIN-1 AND TUMOR NECROSIS FACTOR-α MODULATORS, SYNTHESIS OF SAID MODULATORS AND THEIR ENANTIOMERS AND METHODS OF USING SAID MODULATORS

(75) Inventors: Michael Palladino, Encinitas, CA (US); Emmanuel A. Theodorakis, San Diego, CA (US)

(73) Assignees: Nereus Pharmaceuticals, Inc., San Diego, CA (US); The Regents of the University of California, Oakland, CA (US)

(*) Notice: Subject to any disclaimer, the term of this patent is extended or adjusted under 35 U.S.C. 154(b) by 488 days.

This patent is subject to a terminal disclaimer.

(21) Appl. No.: 10/112,681

(22) Filed: Mar. 27, 2002

(65) Prior Publication Data

US 2003/0050338 A1     Mar. 13, 2003

Related U.S. Application Data

(63) Continuation of application No. 10/068,333, filed on Feb. 4, 2002, now Pat. No. 6,881,857, which is a continuation-in-part of application No. 09/570,202, filed on May 12, 2000, now Pat. No. 6,365,768.

(60) Provisional application No. 60/332,031, filed on Nov. 21, 2001, provisional application No. 60/302,850, filed on Jul. 2, 2001, provisional application No. 60/279,952, filed on Mar. 29, 2001, provisional application No. 60/279,381, filed on Mar. 28, 2001, provisional application No. 60/186,853, filed on Mar. 3, 2000, provisional application No. 60/134,295, filed on May 14, 1999.

(51) Int. Cl.
    *C07C 69/74* (2006.01)
(52) U.S. Cl. ............... 560/117; 560/116; 562/498; 562/499
(58) Field of Classification Search ............... 560/116, 560/117; 562/498, 499
    See application file for complete search history.

(56) References Cited

U.S. PATENT DOCUMENTS

| | | | |
|---|---|---|---|
| 4,874,891 A | 10/1989 | Covey et al. | |
| 5,192,817 A | 3/1993 | Takaishi et al. | |
| 6,051,590 A | 4/2000 | Bao et al. | |
| 6,365,768 B1* | 4/2002 | Palladino et al. | 560/117 |
| 6,881,857 B1* | 4/2005 | Palladino et al. | 560/117 |

FOREIGN PATENT DOCUMENTS

| | | |
|---|---|---|
| WO | WO 95/34300 | 12/1995 |
| WO | WO 99/37600 | 7/1999 |
| WO | WO 00/73253 A1 | 12/2000 |

OTHER PUBLICATIONS

G.T. Chapman et al, Journal of the Chemical Society Abstract (1963) Aug. 4010-17.*
A. Taticchi et al, Tetrahedron vol. 25 pp. 5341-5348 1969.*
Kaufman et al. (1987). synthesis and 13C nuclear magnetic resonance spectral analysis of some diterpenoids related to the cleisanthane type hydrocarbon isolated from *Armphilbolis antarctica*, Canadian Journal of Chemistry 65(9) pp. 2024-2026.
Ohtsuka et al. (1973), Dilerpenoids. Chemical and Pharmaceutical Bulletin 21(3): pp. 643-652.
Chemical abstracts, vol. 127, No. 1 Jul. 7, 1997 (Columbus Ohio) pp. 594, abstract No. 5280z F.G. Cruz et al. Relative stereochemistry determination of primarediens through oxidation productions.
Chemical abstracts, vol. 116, No. 11, Mar. 18, 1992 (Columbus Ohio), p. 411, abstract No. 102859c, C.M. Charny et al., "Diterperioids from *Calceolaria* species, Part 10. Diterpenes from *Calceolaria polifolia*" Phytochemistry 1991, 30(10), 3385-8.
Chemical Abstracts, vol. 114, No. 3, Jan. 21, 1991 (Columbus Ohio), p. 408, abstract No. 20960p, C.M. Charny et al. "Diterpernoids from *Calceolaria* speices Part 5. Diterpenes from *Calceolaria lepida*" Phytochemistry 1990, 29(9), 2943-6.
Chemical abstracts, vol. 77, No. 15, Oct. 9, 1072 (Columbus Ohio), p. 193, abstract No. 98751h, V.K. Morozkov et al. "Neutral fraction of the oleoresin of Pinus sylvestri 3. Norditerpene compounds", Izv. Sib. Otd. Akad Nauk SSSR, Ser. Khim. Neuk 1972, (1), 128-34.
Kim, Y.H. Chung B.S. Pimaradiene Diterpenes from *Acanlihopanox koreanum*, Journal of Natural Products, 1998, vol. 51, No. 8, pp. 1080-1083; p. 1080, paragraphs, 1-3, compound No. 2, p. 1082, paragraph Extraction and Isolation (cited in the application).
Kaufman et al. (1995). Synthesis and mass spectral data of four potential biomarkers related to the C19 tricyclanes found in Australian oils and Puget Sound sediments. Synth. Commun., 25(8), pp. 1205-1221.
Cruz et al. Diterpene Acids from *Mikania triangularis*: 31:8 (1992) 2793-2796.
Knudsen et al. Pimaradiene Diterpenes from *Mikania triangularis*L Phytochemistry: 25:5 (1986) 1240-1242.
Ling et al., "Stereoselective Synthesis of (+) -Acanthoic Acid," *Organic Letters*, 2: 2073-2076 (2000).
Suh et al., "Pimarane Cyclooxygenase 2 (COX-2) Inhibitor and its Structure-Activity Relationship," *Bioorganic & Medicinal Chemistry Letters*, 11: 559-562 (2001).

* cited by examiner

*Primary Examiner*—Zinna N. Davis
(74) *Attorney, Agent, or Firm*—Knobbe Martens Olson & Bear LLP

(57) ABSTRACT

Novel compounds are disclosed that have the following chemical structures, and prodrug esters and acid-addition salts thereof, that are useful as Interleukin-1 and Tumor Necrosis Factor-α modulators, and thus are useful in the treatment of various diseases.

-continued

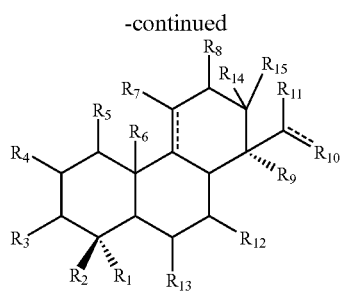

wherein the R groups are defined as follows: if any $R_3$–$R_5$, $R_7$, $R_8$, $R_{11}$–$R_{13}$ is not hydrogen, $R_2$ or $R_6$ or $R_9$ is not methyl, or $R_{10}$ is not $CH_2$, then $R_1$ is selected from the group consisting of hydrogen, a halogen, COOH, $C_1$–$C_{12}$ carboxylic acids, $C_1$–$C_{12}$ acyl halides, $C_1$–$C_{12}$ acyl residues, $C_1$–$C_{12}$ esters, $C_1$–$C_{12}$ secondary amides, $(C_1$–$C_{12})(C_1$–$C_{12})$ tertiary amides, $(C_1$–$C_{12})(C_1$–$C_{12})$ cyclic amides, $(C_1$–$C_{12})$ amines, $C_1$–$C_{12}$ alcohols, $(C_1$–$C_{12})(C_1$–$C_{12})$ ethers, $C_1$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls. If all $R_3$–$R_5$, $R_7$, $R_8$, $R_{11}$–$R_{13}$ are hydrogen, $R_2$, $R_6$, and $R_9$ are each methyl, and $R_{10}$ is $CH_2$, then $R_1$ is selected from hydrogen, a halogen, $C_1$–$C_{12}$ carboxylic acids, $C_1$–$C_{12}$ acyl halides, $C_1$–$C_{12}$ acyl residues, $C_2$–$C_{12}$ esters, $C_2$–$C_{12}$ secondary amides, $(C_1$–$C_{12})$ $(C_1$–$C_{12})$ tertiary amides, $C_2$–$C_{12}$ alcohols, $(C_1$–$C_{12})$ $(C_1$–$C_{12})$ ethers other than methyl-acetyl ether, $C_2$–$C_{12}$ alkyls, $C_1$–$C_{12}$ substituted alkyls, $C_2$–$C_{12}$ alkenyls, $C_2$–$C_{12}$ substituted alkenyls, and $C_2$–$C_{12}$ aryls. $R_2$ and $R_9$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, $C_1$–$C_{12}$ acyl, $C_1$–$C_{12}$ alcohol, and $C_5$–$C_{12}$ aryl. $R_3$–$R_5$, $R_7$, $R_8$, and $R_{11}$–$R_{13}$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, and $C_5$–$C_{12}$ aryl. $R_6$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, and $C_2$–$C_{12}$ alkynyl. $R_{10}$ is selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_{12}$ alcohol, and $C_5$–$C_{12}$ aryl. Pharmaceutical compositions comprising, and uses of, therapeutically effective amounts of the aove compounds and their prodrug esters, and a pharmaceutically acceptable carrier, are also disclosed, and are useful as, for example, anti-inflammatory analgesics, in treating immune disorders, as anti-cancer and anti-tumor agents, and in the treatment of cardiovascular disease, skin redness, and viral infection. Completely synthetic and semi-synthetic methods of making these compounds and their analogs, are also disclosed.

28 Claims, 37 Drawing Sheets

| | | | |
|---|---|---|---|
| NPI 1302 | *(structure)* | | |
| TTL1 | *(structure)* | $C_{20}H_{30}O_2$<br>Mol. Wt.: 302.45 | 2.9 mg |
| TTL2 | *(structure)* | $C_{19}H_{30}O_3$<br>Mol. Wt.: 306.44 | 2.5 mg |
| TTL3 | *(structure)* | $C_{21}H_{32}O_2$<br>Mol. Wt.: 316.48 | 1.8 mg |
| TTL4 | *(structure)* | $C_{20}H_{32}O_3$<br>Mol. Wt.: 320.47 | 2.1 mg |
| TTL5 | *(structure)* | $C_{20}H_{30}O_2$<br>Mol. Wt.: 302.45<br>1:1 mixture of diastereomers at C* | 1.2 mg |

Figure 17

Scheme 1

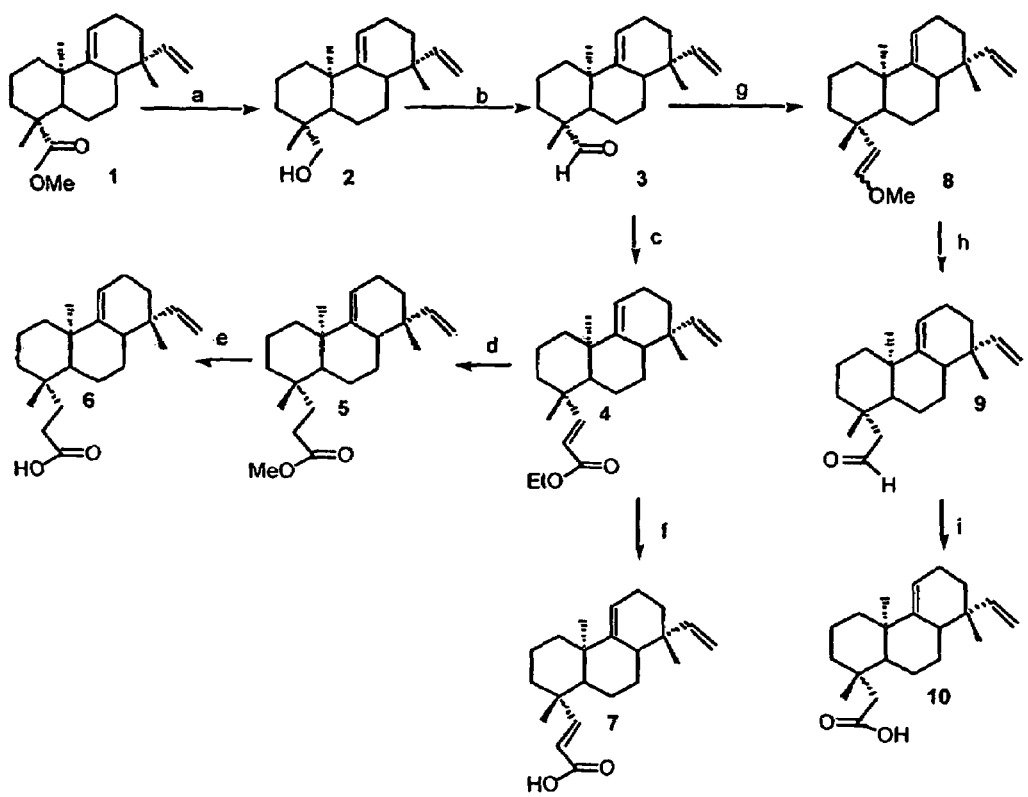

Reagents and conditions: (a) DIBAL (4 equiv), -78 °C to rt, 2h, CH$_2$Cl$_2$, 86%; (b) Dess Martin [O] (1.3 equiv), CH$_2$Cl$_2$, rt, 2.5 h, 74%; (c) NaH (1.6 equiv), triethyl phosphonoacetate (2.2 equiv), THF, 0°C to rt, 70%; (d) Mg (12 equiv), methanol (7 ml), rt, 12h, 87% (e) LiOH (10 equiv), THF/H$_2$0, reflux, 12 h, 71% (f) LiOH (10 equiv), THF/H$_2$0, reflux, 12 h, 76%; (g) MeOCH$_2$PPh$_3$Br (5.2 equiv), *t*BuOK (4.8 equiv), THF, 25 °C, 1 h, 99%; (h) TsOH (1 equiv), acetone, 0 °C, 6 h, 54%; (i) NaH$_2$PO$_4$ (5 equiv), NaClO$_2$ (5 equiv), *t*BuOH/H$_2$O, 2 h, 96%.

Figure 33

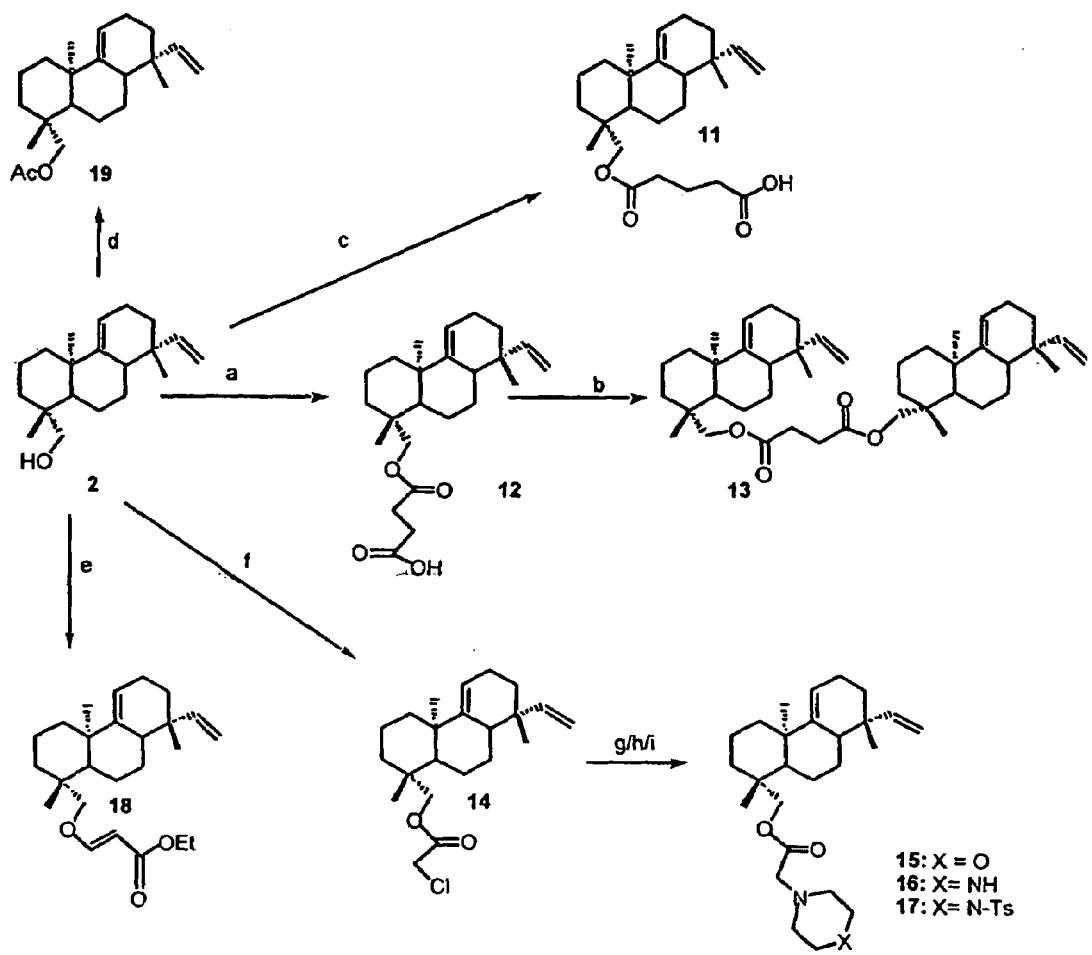

Reagents and conditions: (a) succinic anhydride (1.16 equiv), DMAP (cat.), DCM, rt, 8h, 78% (b) DCC (1.01 equiv), DMAP (cat.), DCM, rt, 70% (c) ) Maleic anhydride (1.2 equiv), DMAP (cat.), DCM, rt, 10h, 71%; (d) acetic anhydride (2.5 equiv), pyridine (5 equiv), $CH_2Cl_2$, 2 h, 84%; (e) 4-methyl morpholine (2.50 equiv), ethyl propiolate (1.44 equiv), $CH_2Cl_2$, 0 °C to rt, 15h, 64%; (f) chloroacetyl chloride (1.53 mmol), DMAP (cat.), $CH_2Cl_2$, 0 °C to rt, 2h, 82%; (g) morpholine (2.5 equiv), DCM, 50 °C, 12h, 71%; (h) Piperazine (2.50 equiv), DCM, 50 °C, 10h, 77%; (i) tosyl chloride (1.38 equiv), $Et_3N$, DCM, rt, overnight, 69%.

Figure 34

Reagents and conditions: (a) ethylene diamine (24 equiv), dry MeOH, rt to 0 °C, NaBH$_4$ (2.5 equiv), 16h, 90%; (b) ethylene diamine (27 equiv), dry MeOH, rt to 0 °C, NaBH$_4$ (2.5 equiv), 16h, 86%; (c) LiBr (2 equiv), DMF, reflux, 2 days, 52%; (d) TMS-diazomethane (excess), methanol/benzene, 20 mi, 25 °C, 82%; (e) DIBAL-H (4.0 equiv), CH$_2$Cl$_2$, -78 °C, 1 h, 94%.

Scheme 5

Reagents and conditions: (a) Ph$_3$P=CO$_2$Me (3 equiv), CH$_2$Cl$_2$, 25 °C, 10 h, 84%; (b) LiOH, THF/H$_2$O, 60 °C, 15 h, 95%; (c) Mg (cat), MeOH, HCl, 25 °C, 15 h, 54%; (d) LiOH, THF/H$_2$O, 60 °C, 15 h, 81%;

INTERLEUKIN-1 AND TUMOR NECROSIS FACTOR-α MODULATORS, SYNTHESIS OF SAID MODULATORS AND THEIR ENANTIOMERS AND METHODS OF USING SAID MODULATORS

RELATED APPLICATIONS

The present application is related to, and claims priority from, the following co-pending provision applications: U.S. Application Ser. No. 60/332,031, filed on Nov. 21, 2001; U.S. Application Ser. No. 60/302,850, filed on Jul. 2, 2001; U.S. Application Ser. No. 60/279,381, filed on Mar. 28, 2001; and U.S. Application Ser. No. 60/279,952, filed on Mar. 29, 2001. The present application is also a continuation-part of, and claims priority from, the following non-provisional applications: U.S. application Ser. No. 10/068,333, filed Feb. 4, 2002, now U.S. Pat. No. 6,881,857 and Ser. No. 09/570,202, filed May 12, 2000, now U.S. Pat. No. 6,365,768. Through both of these non-provisional applications, the present applications also claims priority to the following provisional applications: U.S. Application Ser. No. 60/134,295, filed May 14, 1999, and U.S. Application Ser. No. 60/186,853, filed Mar. 3, 2000.

FIELD OF THE INVENTION

The invention relates to chemical compounds and pharmaceutical compositions, including novel chemical compounds and pharmaceutical compositions thereof, useful in the treatment of various diseases and disease states. The invention also relates to methods of synthesizing natural products and novel, structurally-related chemical compounds. More particularly, the present invention relates to novel analogs of and processes for the preparation of compounds and pharmaceutical compositions thereof useful in the treatment of, for example, inflammation, cancer, cachexia, cardiovascular disease, diabetes, otitis media, sinusitis and transplant rejection.

BACKGROUND OF THE INVENTION

*Acanthopanax koreanum* Nakai (Araliaceae), which is found indigenously in Cheju Island, The Republic of Korea, has been used traditionally as a remedy for, for example, neuralgia, paralysis, and lumbago. Various useful components, including acanthoic acid, a compound having the chemical structure of Formula (I), have been isolated from the root bark of this tree. Furthermore, certain analogs of the compound of Formula (I), for example, wherein the COOH group is replaced by a methanolic group, by a methyl-acetyl ether, by a methyl group, and by a methyl-ester have each also been isolated from the root bark of *Acanthopanax koreanum* Nakai (Araliaceae). See Kim, Y. H. and Chung, B. S., *J. Nat. Pro.*, 51, 1080–83 (1988). (The proper chemical names of these analogs are provided in this reference.) This reference and all the other patents and printed publication cited herein are, in their entirety, incorporated by reference herein.

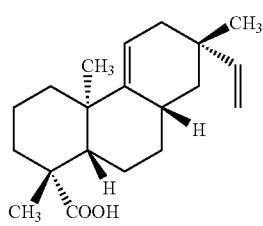

(I)

The compound of Formula (I), also known as acanthoic acid, has been reported to have certain pharmacological effects, including, for example, analgesic and anti-inflammatory activity. The compound of Formula (I) also exhibits very low toxicity; 1000 mg/kg is the minimum lethal dose (MLD) when administered to a rat. See Lee, Y. S., "Pharmacological Study for (–)-Pimara-9(11),15-Diene-19-oic Acid, A Component of *Acanthopanax koreanum* Nakai," Doctorate Thesis, Dept. of Pharmacy, Seoul National University, Korea (1990). The compound of Formula (I) and/or its naturally-occurring analogs, may exhibit these known pharmacological effects by inhibiting leukocyte migration and prostaglandin $E_2(PGE_2)$ synthesis, and is a suspected effector of both Interleukin-1 (IL-1) and Tumor Necrosis Factor-α (TNF-α) production. Additionally, a process for the preparation of acanthoic acid, and use of the acanthoic acid for treatment of immune disease is described in International Patent Publication WO 95/34300 (Dec. 21, 1995).

Also, the compound of Formula (IA), kauranoic acid, and the corresponding methyl-ester analog of the compound of Formula (IA), as well as methanolic reduction analogs of the compound of Formula (IA) have been isolated from the root bark of *Acanthopanax koreanum* Nakai (Araliaceae). See Kim, Y. H. and Chung, B. S., *J. Nat. Pro.*, 51, 1080 (1988). (The proper chemical name of kauranoic acid, (–)-kaur-16-en-19-oic acid, and of the known analogs of kauranoic acid are provided in this reference.)

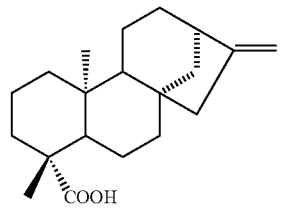

(IA)

Tumor Necrosis Factor-α (herein "TNF-α" or "TNF") and/or Interleukin-1 (herein "IL-1") are involved in various biochemical pathways and, thus modulators of TNF-α and/or IL-1 activity or production, especially novel modulators of TNF-α and/or IL-1 activity or novel compounds that influence the production of either IL-1 or TNF-α, or both, are highly desired. Such compounds and classes of compounds would be valuable in maintaining the human immune system and in treating diseases such as for example, tuberculous pleurisy, rheumatoid pleurisy, and diseases not conventionally considered to be immune disorders, such as cancer, cardiovascular disease, skin redness, viral infection, diabetes, and transplant rejection.

Although numerous approaches to regulate the production of Tumor Necrosis Factor-α and the interleukins are known, novel approaches, compounds, and pharmaceutical formulations to regulate the production of Tumor Necrosis Factor-α and interleukins are highly desirable and have been long sought by those of skill in the art.

SUMMARY OF THE INVENTION

Accordingly, it is an object of the present invention to provide processes for the synthetic and semi-synthetic preparation of the compounds of Formulae (I) and (IA) and their structural analogs, including novel analogs, of the compounds of Formulae (I) and (IA).

The compounds of the present invention include, for example, compounds having the chemical structure of Formula (II) and compounds having the chemical structure of Formula (IIA). Regarding compounds having the chemical structure of Formula (II), the invention includes:

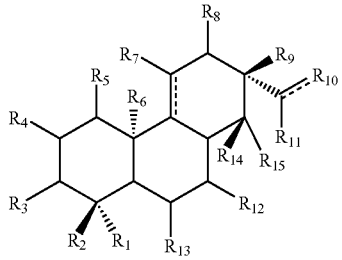

(II)

and their stereo-isomers wherein the R groups are defined as follows: If any $R_3$–$R_5$, $R_7$, $R_8$, $R_{11}$–$R_{13}$ is not hydrogen, $R_2$ or $R_6$ or $R_9$ is not methyl, or $R_{10}$ is not $CH_2$, then $R_1$ is selected from the group consisting of hydrogen, a halogen, COOH, $C_1$–$C_{12}$ carboxylic acids, $C_1$–$C_{12}$ acyl halides, $C_1$–$C_{12}$ acyl residues, $C_1$–$C_{12}$ esters, $C_1$–$C_{12}$ secondary amides, $(C_1$–$C_{12})(C_1$–$C_{12})$ tertiary amides, $C_1$–$C_{12}$ alcohols, $(C_1$–$C_{12})(C_1$–$C_{12})$ ethers, $C_1$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls; however, if all $R_3$–$R_5$, $R_7$, $R_8$, $R_{11}$–$R_{13}$ are hydrogen, $R_2$, $R_6$, and $R_9$ are each methyl, and $R_{10}$ is $CH_2$, then $R_1$ is selected from hydrogen, a halogen, $C_1$–$C_{12}$ carboxylic acids, $C_1$–$C_{12}$ acyl halides, $C_1$–$C_{12}$ acyl residues, $C_2$–$C_{12}$ esters, $C_2$–$C_{12}$ secondary amides, $(C_1$–$C_{12})(C_1$–$C_{12})$ tertiary amides, $C_2$–$C_{12}$ alcohols, $(C_1$–$C_{12})(C_1$–$C_{12})$ ethers other than methyl-acetyl ether, $C_2$–$C_{12}$ alkyls, $C_1$–$C_{12}$ substituted alkyls, $C_2$–$C_{12}$ alkenyls, $C_2$–$C_{12}$ substituted alkenyls, and $C_2$–$C_{12}$ aryls.

$R_2$ and $R_9$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, $C_1$–$C_{12}$ acyl, $C_1$–$C_{12}$ alcohol, and $C_5$–$C_{12}$ aryl.

$R_3$–$R_5$, $R_7$, $R_8$, and $R_{11}$–$R_{13}$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, and $C_5$–$C_{12}$ aryl. In particularly preferred embodiments, $R_{11}$ is a $C_1$–$C_6$ alkyl, or $C_1$–$C_6$ substituted alkyl, and all other R groups are hydrogen.

$R_6$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, and $C_2$–$C_{12}$ alkynyl.

$R_{10}$ is selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_{12}$ alcohol, and $C_5$–$C_{12}$ aryl.

$R_{14}$ and $R_{15}$ are separately selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_6$ alcohol, and $C_5$–$C_6$ aryl, and preferably, both $R_1$ and $R_2$ are not simultaneously methyl.

Regarding compounds having the chemical structure of Formula (IIA), the invention includes:

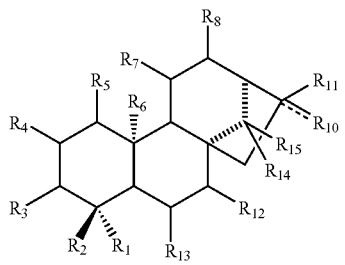

(IIA)

and their stereoisomers wherein, if any $R_3$–$R_5$, $R_7$, $R_8$, $R_{11}$–$R_{13}$ is not hydrogen, $R_2$ or $R_6$ is not methyl, $R_{10}$ is not $CH_2$, or if it is not true that $R_{10}$ is $CH_2OH$ and $R_{11}$ is OH, then $R_1$ is selected from the group consisting of hydrogen, a halogen, COOH, $C_1$–$C_{12}$ carboxylic acids, $C_1$–$C_{12}$ acyl halides, $C_1$–$C_{12}$ acyl residues, $C_1$–$C_{12}$ esters, $C_1$–$C_{12}$ secondary amides, $(C_1$–$C_{12})(C_1$–$C_{12})$ tertiary amides, $C_1$–$C_{12}$ alcohols, $(C_1$–$C_{12})(C_1$–$C_{12})$ ethers, $C_1$–$C_{12}$ alkyls, $C_1$–$C_{12}$ substituted alkyls, $C_2$–$C_{12}$ alkenyls, $C_2$–$C_{12}$ substituted alkenyls; but if all $R_3$–$R_5$, $R_7$, $R_8$, $R_{11}$–$R_{13}$ are hydrogen, $R_2$ and $R_6$ are each methyl, and $R_{10}$ is $CH_2$ or $CH_2OH$, then $R_1$ is selected from hydrogen, a halogen, $C_1$–$C_{12}$ carboxylic acids, $C_1$–$C_{12}$ acyl halides, $C_1$–$C_{12}$ acyl residues, $C_2$–$C_{12}$ esters, $C_1$–$C_{12}$ secondary amides, $(C_1$–$C_{12})(C_1$–$C_{12})$ tertiary amides, $C_2$–$C_{12}$ alcohols, $(C_1$–$C_{12})(C_1$–$C_{12})$ ethers, $C_2$–$C_{12}$ alkyls, $C_2$–$C_{12}$ substituted alkyls, $C_2$–$C_{12}$ alkenyl, and $C_2$–$C_{12}$ substituted alkenyl;

$R_2$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, $C_1$–$C_{12}$ acyl, $C_1$–$C_{12}$ alcohol, and $C_5$–$C_{12}$ aryl;

$R_3$, $R_4$, $R_5$, $R_7$, $R_8$, and $R_{11}$–$R_{13}$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, and $C_5$–$C_{12}$ aryl. In particularly preferred embodiments, $R_{11}$ is a $C_1$–$C_6$ alkyl, or $C_1$–$C_6$ substituted alkyl, and all other R groups are hydrogen;

$R_6$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, and $C_2$–$C_{12}$ alkynyl;

$R_{10}$ is selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_{12}$ alcohol, and $C_5$–$C_{12}$ aryl; and $R_{14}$ and $R_{15}$ may be stereo-specific, and are separately selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_6$ alcohol, and $C_5$–$C_6$ aryl, and preferably, both $R_1$ and $R_2$ are not simultaneously methyl.

It is a further object of the invention to provide compounds having the chemical structure of Formula (IIB), and to provide processes for the synthetic and semi-synthetic preparation of compounds having the chemical structure of Formula (IIB). Regarding said compounds having the chemical structure of Formula (IIB), for example, the compounds herein designated TTL1, TTL2, TTL3, TTL4, and their analogs and derivatives, the invention includes:

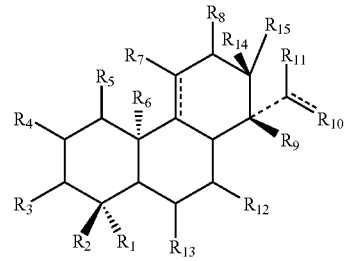

(IIB)

and their stereoisomers wherein the R groups are defined as follows: $R_1$ is selected from the group consisting of hydrogen, a halogen, COOH, $C_1$–$C_{12}$ carboxylic acids, $C_1$–$C_{12}$ acyl halides, $C_1$–$C_{12}$ acyl residues, $C_1$–$C_{12}$ esters, $C_1$–$C_{12}$ secondary amides, $(C_1$–$C_{12})(C_1$–$C_{12})$ tertiary amides, $C_1$–$C_{12}$ alcohols $(C_1$–$C_{12})(C_1$–$C_{12})$ ethers, $C_1$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls. Under these conditions, $R_1$ is preferably selected from COOH, $C_1$–$C_{12}$ carboxylic acids, $C_1$–$C_{12}$ acyl halides, $C_1$–$C_{12}$ acyl residues, and $C_1$–$C_{12}$ esters, and is most preferably selected from COOH and the $C_1$–$C_6$ esters.

$R_2$ and $R_9$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, $C_1$–$C_{12}$ acyl, $C_1$–$C_{12}$ alcohol, and $C_5$–$C_{12}$ aryl.

$R_3$–$R_5$, $R_7$, $R_8$, and $R_{11}$–$R_{13}$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, $C_5$–$C_{12}$ aryl. In particularly preferred embodiments, $R_{11}$ is a $C_1$–$C_6$ alkyl, or $C_1$–$C_6$ substituted alkyl, and all other R groups are hydrogen.

$R_6$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, and $C_2$–$C_{12}$ alkynyl.

$R_{10}$ is selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_{12}$ alcohol, and $C_5$–$C_{12}$ aryl.

$R_{14}$ and $R_{15}$ are stereo-specific and are separately selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_6$ alcohol, and $C_1$–$C_6$ aryl, and preferably, both $R_1$ and $R_2$ are not simultaneously methyl.

It also will be appreciated that the various R groups, most particularly $R_3$, $R_4$, $R_5$, $R_7$, $R_8$, and $R_{11}$–$R_{13}$, may be chosen such that cyclic system are formed. For example, both $R_{13}$ and $R_{12}$ may be ethylene moieties and may include a covalent C—C linkage between their respective terminal carbons, generating an additional six-membered ring in the compound of Formula (IIB). As a further example, biscyclic rings may be formed by choosing appropriate chemical species for the various R groups, most particularly $R_3$, $R_4$, $R_5$, $R_7$, $R_8$, and $R_{11}$–$R_{13}$ of Formula (IIB).

The compounds of the invention include the prodrug esters of the compounds of Formulae (II), (IIA), and (IIB), and the acid-addition salts of the compounds of Formulae (II), (IIA), and (IIB), and pharmaceutical compositions comprising a therapeutically effective amount of the described compounds, including their prodrug esters and their acid-addition salts, optionally in conjunction with a pharmaceutically acceptable carrier. Such compositions are useful as, for example, anti-inflammatory analgesics, in the treatment of immune and auto-immune disorders, as anti-cancer or anti-tumor agents, and are useful in the treatment of cardiovascular disease, skin redness, viral infection, diabetes, otitis media, sinusitis and/or transplant rejection. Particularly, a pharmaceutical composition comprising a therapeutically effective amount of a compound of Formulae (II), (IIA), or (IIB), or a pro-drug ester and acid addition salt of a compound of Formulae (II), (IIA), or (IIB), may be used as an anti-cancer, anti-tumor agent, anti-viral agent, and may be useful in the treatment of cardiovascular disease, skin redness, viral infection, diabetes, otitis media, sinusitis and/or transplant rejection.

The invention also provides novel methods of synthesizing the above described compounds and their analogs comprising the step of performing a Diels-Alder reaction reacting a diene having two or more rings with a dienophile compound to yield a resultant compound have three of more rings; and yielding a desired synthetic compound. The Diels-Alder reaction, along with the selection of the diene and the dienophile affords flexibility in synthesizing a variety of compounds of the invention, and allows for the use of combinatorial chemistry libraries of compounds of the invention, for use biological assays, including clinical trials.

BRIEF DESCRIPTION OF THE FIGURES

Certain preferred embodiments of the invention are illustrated in the Figures. The Figures merely illustrate certain preferred embodiments of the invention and/or certain preferred methods of making and/or of using the invention. The Figures are not intended to limit the scope of the invention described and claimed herein.

FIG. 17 depicts a summary of the syntheses of certain compounds of the invention, and the physical properties of these compounds. Compounds TTL1, TTl2, TTL3, and TTL4 are defined as depicted in this Figure.

FIG. 33 depicts a schematic synthetic scheme (Scheme 1) of the synthesis of TTL3 analogs and certain compounds of the invention.

FIG. 34 depicts a schematic synthetic scheme (Scheme 2) of the synthesis of TTL3 analogs and certain compounds of the invention.

DETAILED DESCRIPTION OF THE PREFERRED EMBODIMENT

Figure 1:
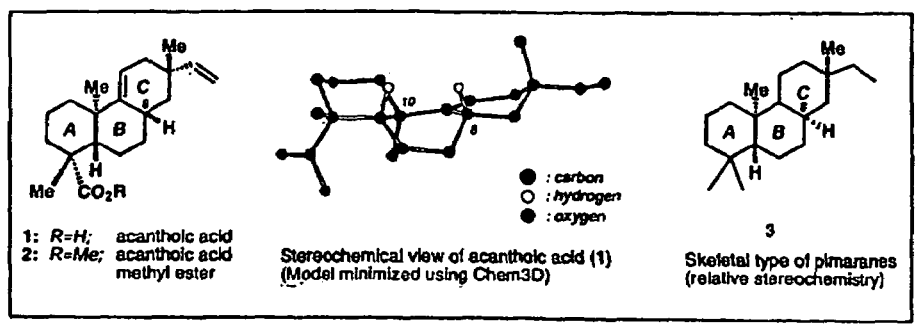
FIG. 1 depicts the structure of acanthoic acid and acanthoic acid methyl ester, a stereo chemical view of acanthoic acid, and a skeletal-type view of certain compounds of the invention.

Certain compounds of the invention have the chemical689—structure shown in Formula (II).

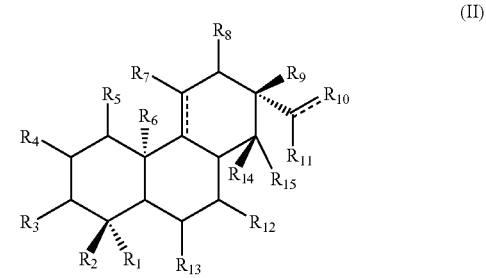

(II)

The R-groups of the compound of Formula (II) may be selected in the following manner. In the event that (1) any R$_3$–R$_5$, R$_7$, R$_8$, R$_{11}$–R$_{13}$ is not hydrogen, (2) R$_2$, R$_6$ or R$_9$ is not methyl, or (3) R$_{10}$ is not CH$_2$, R$_1$ is selected from the group consisting of hydrogen, COOH, C$_1$–C$_{12}$ carboxylic acids, C$_1$–C$_{12}$ acyl halides, C$_1$–C$_{12}$ acyl residues, C$_1$–C$_{12}$ esters, C$_1$–C$_{12}$ secondary amides, (C$_1$–C$_{12}$)(C$_1$–C$_{12}$) tertiary amides, C$_1$–C$_{12}$ alcohols, (C$_1$–C$_{12}$)(C$_1$–C$_{12}$) ethers, C$_1$–C$_{12}$ alkyls, C$_1$–C$_{12}$ substituted alkyls, C$_2$–C$_{12}$ alkenyls, C$_2$–C$_{12}$ substituted alkenyls, and C$_5$–C$_{12}$ aryls. Under these conditions, R$_1$ is preferably selected from COOH, C$_1$–C$_{12}$ carboxylic acids, C$_1$–C$_{12}$ acyl halides, C$_1$–C$_{12}$ acyl residues, and C$_1$–C$_{12}$ esters, and is most preferably selected from COOH and the C$_1$–C$_6$ esters.

However, in the event that (1) all R$_3$–R$_5$, R$_7$, R$_8$, R$_{11}$–R$_{13}$ are hydrogen, (2) R$_2$, R$_6$, and R$_9$ are each methyl, and (3) R$_{10}$, is CH$_2$, R$_1$ is selected from R$_1$ is selected from hydrogen, a halogen C$_1$–C$_{12}$ carboxylic acids, C$_1$–C$_{12}$ acyl halides, C$_1$–C$_{12}$ acyl residues, C$_2$–C$_{12}$ esters, C$_2$–C$_{12}$ secondary amides, (C$_1$–C$_{12}$)(C$_1$–C$_{12}$) tertiary amides, C$_2$–C$_{12}$ alcohols, (C$_1$–C$_{12}$)(C$_1$–C$_{12}$)ethers other than methyl-acetyl ether, C$_2$–C$_{12}$ alkyls, C$_1$–C$_{12}$ substituted alkyls, C$_2$–C$_{12}$ alkenyls, C$_2$–C$_{12}$ substituted alkenyls, and C$_2$–C$_{12}$ aryls. Under these conditions, R$_1$ is preferably selected from C$_1$–C$_{12}$ carboxylic acids, C$_1$–C$_{12}$ acyl halides, C$_1$–C$_{12}$ acyl residues, and C$_2$–C$_{12}$ esters, and is most preferably a C$_4$–C$_8$ ester.

$R_2$ and $R_9$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, $C_1$–$C_{12}$ acyl, $C_1$–$C_{12}$ alcohol, and $C_5$–$C_{12}$ aryl. Preferably, $R_2$ and $R_9$ are each separately selected from the alkyl and alkenyl residues. Most preferably, $R_2$ and $R_9$ are each methyl residues, although one of $R_2$ and $R_9$ may be methyl and the other not methyl in preferred embodiments of the compound of Formula (II).

$R_3$, $R_4$, $R_5$, $R_7$, $R_8$, and $R_{11}$–$R_{13}$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, and $C_5$–$C_{12}$ aryl. Preferably, $R_3$, $R_4$, $R_5$, $R_7$, $R_8$, and $R_1$–$R_{13}$ are each hydrogen or a $C_1$–$C_6$ alkyl, and most preferably $R_3$, $R_4$, $R_5$, $R_7$, $R_8$, and $R_{11}$–$R_{13}$ are each hydrogen. Nevertheless, any one or several of $R_3$, $R_4$, $R_5$, $R_7$, $R_8$, and $R_{11}$–$R_{13}$ may be hydrogen, while the others may be not hydrogen, in preferred embodiments of the compound of Formula (II).

$R_6$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, and $C_2$–$C_{12}$ alkynyl. Preferably, $R_6$ is selected from hydrogen, a halogen, $C_1$–$C_6$ alkyl. More preferably, $R_6$ is a $C_1$–$C_6$ alkyl, and most preferably, $R_6$ is methyl.

$R_{10}$ is selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_{12}$ alcohol, and $C_5$–$C_{12}$ aryl. The bond linking $R_{10}$ to the remainder of the compound of Formula (II) is preferably a C—C double bond, but may be a C—C single bond, a C—H single bond, or a heteroatomic single bond. Preferably, $R_{10}$ is $CH_2$ or $CH_2R'$ wherein R' is a $C_1$–$C_6$ alkyl, or a $C_1$–$C_6$ substituted alkyl. Most preferably, $R_{10}$ is $CH_2$.

$R_{14}$ and $R_{10}$ are separately selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_6$ alcohol, and $C_5$–$C_6$ aryl, with hydrogen and $C_1$–$C_6$ alkyl, $C_1$–$C_6$ substituted alkyl most preferred, and preferably, both $R_1$ and $R_2$ are not simultaneously methyl.

It also will be appreciated that the various R groups, most particularly $R_3$, $R_4$, $R_5$, $R_7$, $R_8$, and $R_{11}$–$R_{13}$, may be chosen such that cyclic system are formed. For example, both $R_{13}$ and $R_{12}$ may be ethylene moieties and may include a covalent C—C linkage between their respective terminal carbons, generating an additional six-membered ring in the compound of Formula (II). As a further example, bis-cyclic rings may be formed by choosing appropriate chemical species for the various R groups, most particularly $R_3$, $R_4$, $R_5$, $R_7$, $R_8$, and $R_{11}$–$R_{13}$, of Formula (II).

Certain preferred compounds of the present invention have the structure shown in Formula (IIA).

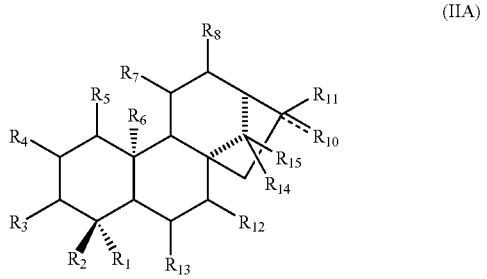

(IIA)

The R-groups of the compound of Formula (IIA) may be selected in the following manner. In the event that if any $R_3$–$R_5$, $R_7$, $R_8$, $R_{11}$–$R_{13}$ is not hydrogen, $R_2$ or $R_6$ is not methyl, $R_{10}$, is not $CH_2$, or if it is not true that $R_{10}$, is $CH_2OH$ and $R_{11}$ is OH, $R_1$ is selected from the group consisting of hydrogen, a halogen, COOH, $C_1$–$C_{12}$ carboxylic acids, $C_1$–$C_{12}$ acyl halides, $C_1$–$C_{12}$ acyl residues, $C_1$–$C_{12}$ esters, $C_1$–$C_{12}$ secondary amides, $(C_1$–$C_{12})(C_1$–$C_{12})$ tertiary amides, $C_1$–$C_{12}$ alcohols, $(C_1$–$C_{12})(C_1$–$C_{12})$ ethers, $C_1$–$C_{12}$ alkyls, $C_1$–$C_{12}$ substituted alkyls, $C_2$–$C_{12}$ alkenyls, $C_2$–$C_{12}$ substituted alkenyls. Under these conditions, $R_1$ is preferably selected from COOH, $C_1$–$C_{12}$ carboxylic acids, $C_1$–$C_{12}$ acyl halides, $C_1$–$C_{12}$ acyl residues, and $C_1$–$C_{12}$ esters, and is most preferably selected from COOH and the $C_1$–$C_6$ esters.

In the event that all $R_3$–$R_5$, $R_7$, $R_8$, $R_{11}$–$R_{13}$ are hydrogen, $R_2$ and $R_6$ are each methyl, and $R_{10}$ is $CH_2$ or $CH_2OH$, $R_1$ is selected from hydrogen, a halogen, $C_1$–$C_{12}$ carboxylic acids, $C_1$–$C_{12}$ acyl halides, $C_1$–$C_{12}$ acyl residues, $C_2$–$C_{12}$ esters, $C_1$–$C_{12}$ secondary amides, $(C_1$–$C_{12})(C_1$–$C_{12})$ tertiary amides, $C_2$–$C_{12}$ alcohol, $(C_1$–$C_{12})(C_1$–$C_{12})$ ethers, $C_2$–$C_{12}$ alkyls, $C_2$–$C_{12}$ substituted alkyls, $C_2$–$C_{12}$ alkenyl, and $C_2$–$C_{12}$ substituted alkenyl. Under these conditions, $R_1$ is preferably selected from $C_1$–$C_{12}$ carboxylic acids, $C_1$–$C_{12}$ acyl halides, $C_1$–$C_{12}$ acyl residues, and $C_2$–$C_{12}$ esters, and is most preferably a $C_4$–$C_8$ ester.

$R_2$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, $C_1$–$C_{12}$ acyl, $C_1$–$C_{12}$ alcohol, and $C_5$–$C_{12}$ aryl. Preferably, $R_2$ and $R_9$ are each separately selected from the alkyl and alkenyl residues. Most preferably, $R_2$ and $R_9$ are each methyl residues, although one of $R_2$ and $R_9$ may be methyl and the other not methyl in preferred embodiments of the compound of Formula (IIA).

$R_3$, $R_4$, $R_5$, $R_7$, $R_8$, and $R_{11}$–$R_{13}$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, and $C_5$–$C_{12}$ aryl. Preferably, $R_3$, $R_4$, $R_5$, $R_7$, $R_8$, and $R_{11}$–$R_{13}$ are each hydrogen or a $C_1$–$C_6$ alkyl, and most preferably $R_3$, $R_4$, $R_5$, $R_7$, $R_8$, and $R_{11}$–$R_{13}$ are each hydrogen. Nevertheless, any one or several of $R_3$, $R_4$, $R_5$, $R_7$, $R_8$, and $R_{11}$–$R_{13}$ may be hydrogen, while the others may be not hydrogen, in preferred embodiments of the compound of Formula (IIA).

$R_6$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, and $C_2$–$C_{12}$ alkynyl. Preferably, $R_6$ is selected from hydrogen, a halogen, $C_1$–$C_6$ alkyl. More preferably, $R_6$ is a $C_1$–$C_6$ alkyl, and most preferably, $R_6$ is methyl.

$R_{10}$ is selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_{12}$ alcohol, and $C_5$–$C_{12}$ aryl. The bond linking $R_{10}$ to the remainder of the compound of Formula (IIA) is preferably a C—C double bond, but may be a C—C single bond, a C—H single bond, or a heteroatomic single bond. Preferably, $R_{10}$ is $CH_2$ or $CH_2R'$ wherein R' is a $C_1$–$C_6$ alkyl, or a $C_1$–$C_6$ substituted alkyl. Most preferably, $R_{10}$ is $CH_2$, and preferably, both $R_1$ and $R_2$ are not simultaneously methyl.

It also will be appreciated that the various R groups, most particularly $R_3$, $R_4$, $R_5$, $R_7$, $R_8$, and $R_{11}$–$R_{13}$, may be chosen such that cyclic system are formed. For example, both $R_{13}$ and $R_{12}$ may be ethylene moieties and may include a covalent C—C linkage between their respective terminal carbons, generating an additional six-membered ring in the compound of Formula (IIA). As a further example, bis-cyclic rings may be formed by choosing appropriate chemical species for the various R groups, most particularly $R_3$, $R_4$, $R_5$, $R_7$, $R_8$, and $R_{11}$–$R_{13}$ of Formula (IIA).

Certain preferred compounds of the present invention, including compounds herein designated TTL1, TTL2, TTL3, and TTL4 have the chemical structure described in Formula (IIB).

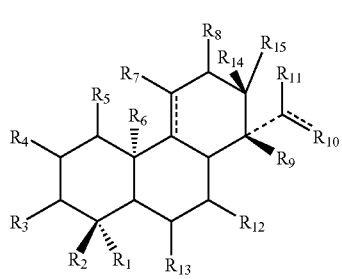

(IIB)

The R-groups of the compound of Formula (IIB) may be selected in the following manner: $R_1$ is selected from the group consisting of hydrogen, a halogen, COOH, $C_1$–$C_{12}$ carboxylic acids, $C_1$–$C_{12}$ acyl halides, $C_1$–$C_{12}$ acyl residues, $C_1$–$C_{12}$ esters, $C_1$–$C_{12}$ secondary amides, ($C_1$–$C_{12}$)($C_1$–$C_{12}$) tertiary amides, $C_1$–$C_{12}$ alcohols, ($C_1$–$C_{12}$)($C_1$–$C_{12}$) ethers, $C_1$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls. Under these conditions, $R_1$ is preferably selected from COOH, $C_1$–$C_{12}$ carboxylic acids, $C_1$–$C_{12}$ acyl halides, $C_1$–$C_{12}$ acyl residues, and $C_1$–$C_{12}$ esters, and is most preferably selected from COOH and the $C_1$–$C_6$ esters.

$R_2$ and $R_9$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, $C_1$–$C_{12}$ acyl, $C_1$–$C_{12}$ alcohol, and $C_5$–$C_{12}$ aryl. Preferably, $R_2$ and $R_9$ are each separately selected from the alkyl and alkenyl residues. Most preferably, $R_2$ and $R_9$ are each methyl residues, although one of $R_2$ and $R_9$ may be methyl and the other not methyl in preferred embodiments of the compound of Formula (IIB).

$R_3$, $R_4$, $R_5$, $R_7$, $R_8$, and $R_{11}$–$R_{13}$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, and $C_5$–$C_{12}$ aryl. Preferably, $R_3$, $R_4$, $R_5$, $R_7$, $R_8$, and $R_{11}$–$R_{13}$ are each hydrogen or a $C_1$–$C_6$ alkyl, and most preferably $R_3$, $R_4$, $R_5$, $R_7$, $R_8$, and $R_{11}$–$R_{13}$ are each hydrogen. Nevertheless, any one or several of $R_3$, $R_4$, $R_5$, $R_7$, $R_8$, and $R_{11}$–$R_{13}$ may be hydrogen, while the others may be not hydrogen, in preferred embodiments of the compound of Formula (IIB).

$R_6$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, and $C_2$–$C_{12}$ alkynyl. Preferably, $R_6$ is selected from hydrogen, a halogen, $C_1$–$C_6$ alkyl. More preferably, $R_6$ is a $C_1$–$C_6$ alkyl, and most preferably, $R_6$ is methyl.

$R_{10}$ is selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_{12}$ alcohol, and $C_5$–$C_{12}$ aryl. The bond linking $R_{10}$ to the remainder of the compound of Formula (II) is preferably a C=C double bond, but may be a C—C single bond, a C—H single bond, or a heteroatomic single bond. Preferably, $R_{10}$ is $CH_2$ or $CH_2R'$ wherein R' is a $C_1$–$C_6$ alkyl, or a $C_1$–$C_6$ substituted alkyl. Most preferably, $R_{10}$ is $CH_2$, and preferably, both $R_1$ and $R_2$ are not simultaneously methyl.

It also will be appreciated that the various R groups, most particularly $R_3$, $R_4$, $R_5$, $R_7$, $R_8$, and $R_{11}$–$R_{13}$, may be chosen such that cyclic system are formed. For example, both $R_{13}$ and $R_{12}$ may be ethylene moieties and may include a covalent C—C linkage between their respective terminal carbons, generating an additional six-membered ring in the compound of Formula (IIB). As a further example, biscyclic rings may be formed by choosing appropriate chemical species for the various R groups, most particularly $R_3$, $R_4$, $R_5$, $R_7$, $R_8$, and $R_{11}$–$R_{13}$ of Formula (IIB).

Definitions

As used herein, the term "alkyl" means any unbranched or branched, saturated hydrocarbon, with $C_1$–$C_6$ unbranched, saturated, unsubstituted hydrocarbons being preferred, and with methyl, ethyl, iosbutyl, and tert-butyl being most preferred. Among the substituted, saturated hydrocarbons, $C_1$–$C_6$ mono- and di- and pre-halogen substituted saturated hydrocarbons and amino-substituted hydrocarbons are preferred, with perfluromethyl, perchloromethyl, perfluoro-tert-butyl, and perchloro-tert-butyl being the most preferred. The term "substituted alkyl" means any unbranched or branched, substituted saturated hydrocarbon, with unbranched $C_1$–$C_6$ alkyl secondary amines, substituted C1–C6 secondary alkyl amines, and unbranched $C_1$–$C_6$ alkyl tertiary amines being within the definition of "substituted alkyl," but not preferred. The term "substituted alkyl" means any unbranched or branched, substituted saturated hydrocarbon. Cyclic compounds, both cyclic hydrocarbons and cyclic compounds having heteroatoms, are within the meaning of "alkyl."

As used herein, the term "substituted" means any substitution of a hydrogen atom with a functional group.

As used herein, the term "functional group" has its common definition, and refers to chemical moieties preferably selected from the group consisting of a halogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl, cyano, and nitro. Functional groups may also be selected from the group consisting of —$SR_S$, —$OR_O$, —$NR_{n1}R_{n2}$, —$N^+R_{n1}R_{n2}R_{n3}$, —N=N—$R_{n1}$, —$P^+R_{n1}R_{n2}R_{n3}$, —$COR_C$, —C(=$NOR_O$)$R_C$, —$CSR_C$, —$OCOR_C$, —$OCONR_{n1}R_{n2}$, —$OCO_2R_C$, —$CONR_{n1}R_{n2}$, —C(=N)$NR_{n1}R_{n2}$, —$CO_2R_O$, —$SO_2NR_{n1}R_{n2}$, —$SO_3R_O$, —$SO_2R_O$, —PO($OR_O$)$_2$, —$NR_{n1}CSNR_{n2}R_{n3}$. Substituents of these functional groups $R_{n1}$, $R_{n2}$, $R_{n3}$, $R_O$ and $R_S$ are preferably each separately selected from the group consisting of a hydrogen atom, $C_1$–$C_{20}$ alkyl, substituted $C_1$–$C_{20}$ alkyl, cyloalkyl, substituted cycloalkyl, aryl, substituted aryl, benzyl, heteroaryl, substituted heteroaryl and may constitute parts of an aliphatic or aromatic heterocycle. $R_C$ are preferably selected from the group consisting of a hydrogen atom, $C_1$–$C_{20}$ alkyl, substituted $C_1$–$C_{20}$ alkyl, perhalogenated alkyl, cyloalkyl, substituted cycloalkyl, aryl, substituted aryl, benzyl, heteroaryl, substituted heteroaryl and cyano.

As used herein, the terms "halogen" and "halogen atom" refer to any one of the radio-stable atoms of column 17 of the Periodic Table of the Elements, preferably fluorine, chlorine, bromine, or iodine, with fluorine and chlorine being particularly preferred.

As used herein, the term "alkenyl" means any unbranched or branched, substituted or unsubstituted, unsaturated hydrocarbon, with $C_1$–$C_6$ unbranched, mono-unsaturated and di-unsaturated, unsubstituted hydrocarbons being preferred, and mono-unsaturated, di-halogen substituted hydrocarbons being most preferred. The term "substituted alkenyl" means any unbranched or branched, substituted unsaturated hydrocarbon, substituted with one or more functional groups, with unbranched $C_2$–$C_6$ alkenyl secondary amines, substituted $C_2$–$C_6$ secondary alkenyl amines, and unbranched $C_2$–$C_6$ alkenyl tertiary amines being within the definition of "substituted alkyl." The term "substituted alkenyl" means any unbranched or branched, substituted unsaturated hydrocarbon. Cyclic compounds, both unsaturated cyclic hydrocarbons and cyclic compounds having heteroatoms, are within the meaning of "alkenyl."

As used herein, the term "alcohol" means any unbranched or branched saturated or unsaturated alcohol, with $C_1$–$C_6$ unbranched, saturated, unsubstituted alcohols being preferred, and with methyl, ethyl, isobutyl, and tert-butyl alcohol being most preferred. Among the substituted, saturated alcohols, $C_1$–$C_6$ mono- and di-substituted saturated alcohols are preferred. The term "alcohol" includes substituted alkyl alcohols, and substituted alkenyl alcohols.

As used herein, the term "aryl" encompasses the terms "substituted aryl," "heteroaryl," and "substituted heteroaryl" which refer to aromatic hydrocarbon rings, preferably having five or six atoms comprising the ring. The terms "heteroaryl" and "substituted heteroaryl" refer to aromatic hydrocarbon rings in which at least one heteroatom, for example, oxygen, sulfur, or nitrogen atom, is in the ring along with at least one carbon atom. "Aryl," most generally, and "substituted aryl," "heteroaryl," and "substituted heteroaryl" more particularly, refer to aromatic hydrocarbon rings, preferably having five or six atoms, and most preferably having six atoms comprising the ring. The term "substituted aryl" includes mono and poly-substituted aryls, substituted with, for example, alkyl, aryl, alkoxy, azide, amine, and amino groups. "Heteroaryl" and "substituted heteroaryl," if used separately, specifically refer to aromatic hydrocarbon rings in which at least one heteroatom, for example, oxygen, sulfur, or nitrogen atom, is in the ring along with at least one carbon atom.

The terms "ether" and "alkoxy" refer to any unbranched, or branched, substituted or unsubstituted, saturated or unsaturated ether, with $C_1$–$C_6$ unbranched, saturated, unsubstituted ethers being preferred, with dimethyl, diethyl, methyl-isobutyl, and methyl-tert-butyl ethers being most preferred. The terms "ether" and "alkoxy," most generally, and "cycloalkoxy" and cyclic ether" more particularly, refer to any non-aromatic hydrocarbon ring, preferably having five to twelve atoms comprising the ring.

The term "ester" refer to any unbranched, or branched, substituted or unsubstituted, saturated or unsaturated ester, with $C_1$–$C_6$ unbranched, saturated, unsubstituted esters being preferred, with methyl ester, and isobutyl ester being most preferred.

The term "pro-drug ester," especially when referring to a pro-drug ester of the compound of Formula (I), refers to a chemical derivative of the compound that is rapidly transformed in vivo to yield the compound, for example, by hydrolysis in blood. The term "pro-drug ester" refers to derivatives of the compound of the present invention formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14–21 (1987) (providing examples of esters useful as prodrugs for compounds containing carboxyl groups).

The term "pharmaceutically acceptable salt," especially when referring to a pharmaceutically acceptable salt of the compound of Formula (I), refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example $C_1$–$C_7$ alkylamine, cyclohexylamine, triethanolamine, ethylenediamine or tris-(hydroxymethyl)-aminomethane. With respect to compounds of the invention that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid. Preferred pharmaceutical compositions of the present invention include pharmaceutically acceptable salts and pro-drug esters of the compound of Formulae (II), (IIA), and (IIB).

The terms "purified," "substantially purified," and "isolated" as used herein refer to the compound of the invention being free of other, dissimilar compounds with which the compound of the invention is normally associated in its natural state, so that the compound of the invention comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample.

The terms "anti-cancer," "anti-tumor" and "tumor-growth-inhibiting," when modifying the term "compound," and the terms "inhibiting" and "reducing", when modifying the terms "compound" and/or the term "tumor," mean that the presence of the subject compound is correlated with at least the slowing of the rate of growth of the tumor or cancerous mass. More preferably, the terms "anti-cancer," "anti-tumor," "tumor-growth-inhibiting," "inhibiting," and "reducing" refer to a correlation between the presence of the subject compound and at least the temporary cessation of tumor growth or growth of the cancerous mass. The terms "anti-cancer," "anti-tumor," "tumor-growth-inhibiting," "inhibiting," and "reducing" also refer to, particularly in the most preferred embodiment of the invention, a correlation between the presence of the subject compound and at least the temporary reduction in the mass of the tumor. These terms refer to cancer and various malignancies in animals, specifically in mammals, and most specifically in humans.

The term "skin redness" means any skin redness, especially a chronic skin redness having a neurogenic origin, consistent with, but not limited by, its meaning in EP 7744250, which is hereby incorporated by reference herein in its entirety.

The term "viral infection" means any infection of a viral origin including rhinovirus, and preferably, but not exclusively, refers to human immunodeficiency virus (HIV), human cytomegalovirus, hepatitis A, hepatitis B, and hepatitis C viruses.

The term "cardiovascular disease" refers to the various diseases of the heart and vascular systems, including but not limited to congestive heart failure, cardiac dysfunction, reperfusion injury, and various known peripheral circulatory abnormalities. "Cardiovascular disease" refers to such diseases in animals, specifically in mammals, and most specifically in humans.

As used herein, the term "diabetes" refers to the various diseases related to elevated insulin levels, Insulin Resistance, or Diabetes, including Type 1 Diabetes, Type 2 Diabetes, and various related condition, including, but not limited to Stein-Leventhal Syndrome or Polycystic Ovary Syndrome (PCOS).

As used herein, the term "transplant rejection" refers to the conditions, and related symptoms known as allograft rejection, xenograft rejection, and autograft rejection, and in preferred embodiments of the invention, refers to human—human allograft rejection.

As used herein, the terms "modulator" or "modulation" refer to the capacity of a compound or course of treatment to alter the presence or production of a modulated compound, especially TNF-α or IL-1, in an individual. Most preferably, "modulator" or "modulation" refer to the capacity of a compound or course of treatment to reduce the presence or production of a modulated compound.

As used herein, the terms TTL1, TTL2, TTL3, TTL4 and TTL5 refer to the specific chemical entities identified in, among other figures, FIG. 17.

All other chemical, medical, pharmacological, or otherwise technical terms used herein are to be understood as they would be understood by persons of ordinary skill in the art.

Interleukin-1 (IL-1)

Interleukin-1 (IL-1) is a regulatory factor which participates in a wide range of mammalian immune and inflammatory mechanisms and other defensive mechanism, especially mechanisms in the human body. See, e.g., Dinarello, D. A., *FASEB J.*, 2, 108 (1988). IL-1, first discovered as produced by activated macrophages, is secreted by various cells, for example, fibroblasts, keratinocytes, T cells, B cells, and astrocytes of the brain, and has been reported to have various functions including: stimulating the proliferation of CD4+ T cells, see Mizel, S. B., *Immunol. Rev.*, 63, 51 (1982); stimulating the cell-killing effect of thymic $T_C$ cells through its binding to a T cell receptor, TCR, see McConkey, D. J., et al., *J. Biol. Chem.*, 265, 3009(1990); inducing the production of various materials participating in the inflammatory mechanisms, for example, $PGE_2$, phospholipase $A_2$ ($PLA_2$) and collagenase, see Dejana, E., et al., *Bolid*, 69, 695–699 (1987)); inducing the production of acute-phase proteins in liver, see Andus, T., et al., *Eur. J. Immunol.*, 123, 2928 (1988)); raising blood pressure in the vascular system, see Okusawa, S., et al., *J. Clin. Invest.*, 81, 1162 (1988)); and inducing the production of other cytokines, for example, IL-6 and TNF-α, see Dinarello, C. A., et al., *J. Immunol.*, 139, 1902(1987). IL-1 modulation is also known to effect rheumatoid arthritis, see Nouri, A. M., et al., *Clin. Exp. Immunol.*, 58, 402(1984); transplant rejection, see Mauri and Teppo, *Transplantation*, 45, 143 (1988); and septicemia, see Cannon, J. G., et al., *Lymphokine Res.*, 7, 457 (1988), and IL-1 may induce fever and pain when administered in large doses. See Smith, J., et al., *Am. Soc. Clin. Oncol.*, 9, 710 (1990)).

The occurrence of septicemia, arthritis, inflammations, and related conditions in animal models can be decreased by inhibiting IL-1 binding to its receptors by employing naturally occurring IL-1 receptor inhibitors (IL-1 Ra), see Dinarello, C. A. and Thompson, R. C., *Immunol. Today*, 12, 404 (1991), and certain methods for inhibiting the activity of IL-1 by employing particular antibodies have been proposed, see Giovine, D. F. S. and Duff, G. W., *Immunol. Today*. 11, 13 (1990). In case of IL-6, proliferation of myelocytes in a patient suffering from myeloma which is caused by an excessive secretion of IL-6 has been suppressed by employing antibodies against IL-6 or IL-6 receptor, see Suzuki, H., *Eur. J. Immuno.*, 22, 1989(1992)). The disease condition treatable according to the invention, via TNF-α and IL-1 modulation induced by the compounds of the invention, include but are not necessarily limited to the disease conditions herein described.

Tumor Necrosis Factor-α (TNF-α)

Human TNF-α was first purified in 1985. See Aggarwal, B. B.; Kohr, W. J. "Human tumor necrosis factor. Production, purification and characterization". *J. Biol. Chem.* 1985, 260, 2345–2354. Soon after, the molecular cloning of the TNF cDNA and the cloning of the human TNF locus were accomplished. See Pennica, D.; Nedwin, G. E.; Hayflick, J. S. et al "Human necrosis factor: precursor structure, expression and homology to lymphotoxin". *Nature* 1984, 312, 724–729. Wang, A. M.; Creasy, A. A.; Ladner, M. B. "Molecular cloning of the complementary DNA for human Tumor Necrosis Factor". *Nature* 1985, 313, 803–806. TNF-α is a trimeric 17-KDa polypeptide mainly produced by macrophages. This peptide is initially expressed as a 26-KDa transmembrane protein from which the 17-KDa subunit is cleaved and released following proteolytic cleavage by an enzyme known as TACE. This work clarified the immense and multifaceted biological implications of TNF-α and spurred the development of therapeutic approaches targeting its overproduction.

Tumor necrosis factor-α (TNF-α), is typically produced by various cells, for example, activated macrophages and fibroblasts. TNF-α has been reported to induce IL-1 production, see Dinarello, D. A., *FASEB J.*, 2, 108 (1988), kill the fibrosarcoma L929 cells, see Espevik and Nissen-Meyer, *J. Immunol. Methods*, 95, 99 (1986); to stimulate the proliferation of fibroblasts, see Sugarman, B. J., et al., *Science*, 230, 943(1985); to induce the production of $PGE_2$ and arachidonic acid, both of which may be involved in inflammatory responses, see Suttys, et al., *Eur. J. Biochem.*, 195, 465 (1991); and to induce the production of IL-6 or other growth factors, see Van Hinsbergh, et al., *Blood*, 72, 1467 (1988)). TNF-α has also been also reported to participate, either directly or indirectly, in various diseases such as infectious diseases carried by *trypanosoma* strains of the genus *Plasmodium*., see Cerami, A., et al., *Immunol. Today*, 9, 28 (1988)); autoimmune diseases such as systemic lupus erythematosus (SLE) and arthritis, see Fiers, W., *FEBS*, 285, 199 (1991); Acquired Immune Deficiency Syndrome (AIDS), see Mintz, M., et al., *Am. J. Dis. Child.*, 143, 771 (1989); septicemia, see Tracey, K. J., et al., *Curr. Opin. Immunol.*, 1, 454 (1989); and certain types of infections, see Balkwill, F. R., *Cytokines in Cancer Therapy*, Oxford University Press (1989).

TNF-α and Inflammatory Response

Infection and tissue injury induce a cascade of biochemical changes that trigger the onset of perplexing reactions of the immune system, collectively referred to as inflammatory response. The evolution of this response is based, at least in part, on local vasodilation or enhancing vascular permeability and activation of the vascular endothelium, which allows white blood cells to efficiently circulate and migrate to the damaged site, thereby increasing their chances to bind to and destroy any antigens. The vascular endothelium is thought to then be activated or inflamed. Generally, inflammation is a welcomed immune response to a variety of unexpected stimuli, and as such it exhibits rapid onset and short duration (acute inflammation). Its persistent or uncontrolled activity (chronic inflammation) has, however, detrimental effects to the body and results in the pathogenesis of several immune diseases, such as: septic shock, rheumatoid arthritis, inflammatory bowel diseases and congestive heart failure. See "Tumor Necrosis Factors. The molecules and their emerging role in medicine" B. Beutler, Ed., Raven Press, N.Y. 1992, pages 1–590.

The unfolding of an effective immune response typically requires the recruitment of a variety of cells and the orchestration of a series of biological events. This complex intercellular coordination and interaction is mediated by a group of locally secreted low molecular weight proteins that are collectively called cytokines. These proteins bind to specific receptors on the cell surface and trigger signal-transduction pathways that ultimately alter gene expression in the target cells, thereby regulating an efficient inflammatory response.

Cytokines may exhibit properties of pleiotropism (a given protein exerts different effects on different cells), redundancy (two or more cytokines mediate similar functions), synergism (the combined effect of two cytokines is greater than the additive effect of each individual protein) and antagonism (the effect of one cytokine inhibiting the effect of another). To this end, some of the cytokines are pro-inflammatory (induce inflammation), while some others are anti-inflammatory (inhibit inflammation). The class of pro-inflammatory cytokines includes: interleukin-1 (IL-1), interleukin-6 (IL-6) and tumor necrosis factor-alpha (TNF-$\alpha$). See "Tumor Necrosis Factors. The molecules and their emerging role in medicine" B. Beutler, Ed., Raven Press, N.Y. 1992, pages 1–590. These cytokines are secreted by macrophages shortly after the initiation of the inflammatory response and induce coagulation, increase the vascular permeability and activate the expression of adhesion molecules on vascular endothelial cells (for example, TNF-$\alpha$ stimulates expression of E-selection, that binds to and recruits neutrophils to the site of damage). Subsequently, and during a more systemic immune response, these cytokines act on several organs of the body, including bone marrow and liver to ensure the increased production of white blood cells and the synthesis of appropriate hormones and acute-phase proteins. In addition, they act on the hypothalamus and induce fever, which helps to inhibit the growth of pathogens and enhances the overall immune reaction.

TNF-$\alpha$ and the Pathogenesis of Various Diseases and Conditions

As with any other cytokine, TNF-$\alpha$ is neither completely beneficial nor completely destructive to the host. Rather, balance of its production and regulation is maintained to ensure that the host can effectively react to invading microorganisms without compromising host well-being in the process. Being a mediator of inflammation, TNF-$\alpha$ helps the body in its fight against bacterial infections and tissue injuries by boosting an appropriate immune response. However, its overproduction leads to chronic inflammation, has detrimental effects to the body and plays a major role in the pathogenesis of several diseasessome of which are summarized below.

Bacterial septic shock. This disease typically develops following infection by certain gram-negative bacteria, such as *E. coli, Enterobacter aerogenes* and *Neisseria meningitidis*. These bacteria bear on their cell walls certain lipopolysaccharides (endotoxins) that stimulate macrophages to overproduce IL-1 and TNF-$\alpha$, which in turn cause the septic shock. The symptoms of this condition, which are often fatal, include a drop in blood pressure, fever, diarrhea and widespread blood clotting. In the United States alone, this condition afflicts about 500,000 persons per year and causes more than 70,000 deaths. The annual cost for treating this disease is an estimated $ 5–10 billion.

Rheumatoid Arthritis. This is the most common human autoimmune disease, affecting about 1% of the Western population and is a major source of disability, which in its severe form leads to death. See Szekanecz, Z.; Kosh, A. E.; Kunkel, S. L.; Strieter, R. M. "Cytokines in rheumatoid arthritis. Potential targets for pharmacological applications". *Clinical Pharmacol.* 1998, 12, 377–390. Camussi, G.; Lupin, E. "The future role of anti-tumor necrosis factor products in the treatment of rheumatoid arthritis". *Drugs* 1998, 55, 613–620. This condition is characterized by inflammation and cellular proliferation of the synovium, which results in the invasion of the adjacent cartilage matrix, its subsequent erosion and ultimately bone destruction. Although the origins of this inflammatory response are poorly understood, an increased expression of TNF-$\alpha$ and IL-1 have been found around the area of cartilage erosion. More recently, the pathogenic role of TNF-$\alpha$ in this disorder has been extensively studied and experimentally verified. Furthermore, clinical data suggest that neutralization of TNF-$\alpha$ may be a therapeutic approach to reduce the erosive process. To date, however, current therapy, while providing temporary relief does not alter the fundamental mechanisms of progress or process of the disease.

Inflammatory bowel diseases and related conditions. This class of diseases which include Crohn's disease and ulcerative colitis are debilitating disorders, characterized by chronic inflammation of intestinal mucosa and lamina propria. Although the events that trigger their onset are unknown, they are associated with significant leukocyte infiltrate and local production of soluble mediators. TNF-$\alpha$ is therefore considered to be a key mediator in the pathogenesis of these conditions, either by a direct cytotoxic action or as an orchestrator of the inflammatory cascade. See, for example, Armstrong, A. M.; Gardiner, K. R.; Kirk, S. J.; Halliday, M. J.; Rowlands, B. J. "Tumour necrosis factor and inflammatory bowel disease". *Brit. J. Surgery* 1997, 84, 1051–1058. Data based on accepted animal models also supports the rationale for a therapeutic study in human IBD, aimed at reducing the effect of TNF. See Van Deventer, S. J. H. "Tumour necrosis factor and Crohn's disease" *Gut*, 1997, 40, 443.

Congestive heart failure. Activation of cytokines, and especially TNF-$\alpha$, occurs in patients with chronic heart failure and acute myocardial infarction. See Ferrari, R. "Tumor necrosis factor in CHF: a double facet cytokine". *Cardiovascular Res.* 1998, 37, 554–559. Moreover, TNF-$\alpha$ has been demonstrated to trigger the apoptotic process in cardiac myocytes both directly (by binding to and genetically reprogramming these cells) and indirectly (through local NO production, which also leads to cell death).

HIV replication. Replication of HIV is activated by the inducible transcription factor NF-$\kappa$B, which in turn is induced by TNF-$\alpha$. HIV expression can be induced by TNF in macrophage lines and T-cell clones chronically infected with the virus. Infusion of recombinant TNF in a small number of patients with AIDS-related Kaposi's sarcoma appeared to cause an increase in the HIV p24 antigen level, a marker of viral replicative activity. See "Therapeutic modulation of cytokines" CRC Press, Inc., N.Y. 1996, pages 221–236. These results provide a mechanistic basis for considering the use of a TNF blocker to reduce infectious HIV burden.

Other TNF mediated pathologies. There is an ever-increasing list of conditions in which there is some evidence that TNF is involved. "Therapeutic modulation of cytokines" CRC Press, Inc., N.Y. 1996, pages 221–236. In some cases, such as transplantation, graft-vs-host disease, and ischemia/reperfusion injury the potential mechanism of pathogenesis implicates the pro-inflammatory activity of TNF-α to a variety of tissue cells. Others, such as the suppression of insulin responsiveness in non-insulin-dependent diabetes, relate to more selective actions of TNF-α that appear to fall outside the standard pro-inflammatory model. TNF-α has been detected locally in patients afflicted with otitis media (inner ear infection, with or without effusion), see for example, Willett, D. N., Rezaee, R. P., Billy, J. M., Tighe, M. A., and DeMaria, T. F., *Ann. Rhinol Laryngol*, 107 (1998); Maxwell, K., Leonard, G., and Kreutzer, D. L., *Arch Otolarygol Head Neck Surg*, vol. 123, p. 984 (September 1997), and with sinusitis, see for example Nonoyana, T., Harada, T., Shinogi, J., Yoshimura, E., Sakakura, Y., *Auris Nasus Larynx*, 27(1), 51–58 (January 2000); Buehring I., Friedrich B., Schaff, J., Schmidt H., Ahrens P., Zielen S., *CLin Exp Immul*, 109(3), 468–472, September 1997).

Methods of Use

In further embodiments, the present invention include the use of the disclosed compounds and pharmaceutical compositions including the disclosed compounds, in the treatment of diseases, detailed above, that include inflammation, cancer, cachexia, otitis media, sinusitis and transplant rejection, and the reduction or cessation of fatigue associated with cancer and/or its treatment.

Specific examples of or other such treatable diseases, which may be specifically associated with the eye, nose, and/or ear include thyroid-related diseases (Hunt et al., *Clin Endocrinol*, 55(4):491–9 (2001)), such as Graves' ophthalmopathy (Villanueva et al., *Thyroid*, 10(9):791–8 (2000); Jones et al., *Thyroid*, 10(8):701–7 (2000); Wakelkamp et al., *Clin. Exp. Immunol.*, 121(3) 453–7 (2000); Song et al., *Horm. Metabl. Res.*, 32(7): 277–82 (2000)), Hashimoto's thyroiditis (Paolieri et al., *Ann. NY Acad. Sci.*, 876:221–8 (1999)), thryoid-associated ophthalmopathy (TAO) (Pappa et al., *Clin. Exp. Immunol.*, 109(2):362–9 (1997)) and nodular goiter (Nygaard et al., *Horm. Metabl. Res.*, 32(7):283–7 (2000)); herpetic stromal keratitis (Keadle et al., *Invest. Ophthalmol. Vis. Sci.*, 41(1):96–102 (2000)) and microbial keratitis and peripheral ulcerative keratitis (Dana et al., *Cornea*, 19(5):625–43 (2000); Behcet's disease (Sfikakis et al., *Lancet.*, 358(9278):295–6 (2001)); Goossens et al., *Ann. Rheum. Dis*, 60(6):637 (2001)); Robertson et al., *Rheumatology*, 40(4):473–4 (2001)); Hassard et al., *Gastroenterology*, 120(4):995–9 (2001); Sakane et al., *Expert Opin. Investig. Drugs*, 9(9):1993–2005 (2000)); uveitis (Lemaitre et al., *Invest. Ophthalmol. Vis. Sci.*, 42(9):2022–30 (2001)); Shao et al., *Invest. Ophthalmol. Vis. Sci.*, 42(9): 2016–21 (2001); Baatz et al., *Exp. Eye Res.*, 73(1): 101–9 (2001)); Sjogren's syndrome (Magnusson et al., *Scand J. Immunol.*, 54(1–2): 55–61 (2001); Koski et al., *Clin. Exp. Rheumatol.*, 19(2): 131–7 (2001); Fox, R., *Expert Opin. Investig. Drugs*, 9(9): 2007–16 (2000); Nakamura et al., *Lab Invest*, 80(9):1421–7 (2000); Guggenbuhl et al., *Joint Bone Spine*, 67(4):290–5 (2000)); tuberculosis (Saita et al., 68(10):5991–7 (2000)); inflammatory diseases, such as cochlear inflammation (Ichimiya et al., *Int. J. Pediatr. Otorhinolaryngol.*, 56(1): 45–51 (2000)) and inflammatory eye disease (Smith et al., *Arthritis Rheum.*, 45(3):252–7 (2001)); vitreoretinal proliferative disease (Limb et al., *Invest. Ophthalmol. Vis. Sci.*, 42(7): 1586–91 (2001); El-Ghrably et al., *Br. J. Ophthalmol.*, 85(4): 461–70 (2001); rabies virus ocular disease (Camelo et al., *J. Virol.*, 75(7):3427–34 (2001)); Vogt-Koyanagi-Harada's disease (Kitaichi et al., *Microbiol. Immunol.*, 44(12):107507 (2000)); retinopathy (Yossuck et al., *Mol. Genet. Metab.*, 72(2):164–7 (2001)); vernal keratoconjunctivitis (Leonardi et al., *Invest. Ophthalmol. Vis. Sci.*, 41(13):4175–81 (2000)); retinal laser photocoagulation (Er et al., *Ophthalmic Surg Lasers*, 31(6):479–83 (2000)); acute retinal necrosis syndrome (Sato et al., *Nippon Ganka Gakkai Zasshi*, 104(5):354–62 (2000)); systemic vasculitis (McKibbin et al., *Br. J. Ophthalmol.*, 84(4):395–8 (2000)); sarcoid myopathy (Peris et al, *Clin. Rheumatol.*, 18(6): 488–91 (1999)); recurrent aphthous stomatitis (RAS) (Freysdottir et al., *Clin. Exp. Immunol.*, 118(3):451–7 (1999)); neovascular glaucoma (Chen et al., *Invest. Ophthalmol. Vis. Sci.*, 40(11):2627–32 (1999)); bacterial eye infections, such as *Staphylococcus aureus* endophthalmitis (Giese et al., *Invest. Ophthalmol. Vis. Sci.*, 39(13):2785–90 (1998)) and *Pseudomonas aeruginosa* corneal infection (Kernacki et al., *Infect. Immun.*, 66(1):376–9 (1998)); ocular allergic diseases (Hingorani et al., *J. Allergy Clin. Immunol.*, 102(5):821–30 (1998)), such as allergic conjunctiva (Macleod et al., *Clin. Exp. Allergy*, 27(11):1328–34 (1997)); sarcoidosis (Maniwa et al., *Intern. Med*, 37(9):757–61 (1998)); retinal detachment (Bakunowicz-Lazarczk et al., *Klin. Oczna*, 99(2):87–9 (1997)); optic neuritis (Boiko et al., *J. Neurovirol.*, 6 (Suppl 2):S152–5 (2000); Kivisakk et al., *Neurology*, 50(1):217–23 (1998)); ocular rosacea (Barton et al., *Ophthalmology*, 104(11):1868–74 (1997)), multiple sclerosis (Cooper et al., *Med. Hypotheses*, 49(4):307–11 (1997)) and systemic sclerosis (Hebbar et al., *Arthritis Rheum.*, 38(3):406–12 (1995)); hereditary retinal degeneration (de Kozak et al., *Ocul. Immunol. Inflamm.*, 5(2):85–94 (1997)); retinal dystrophy (Cotinet et al., *Glia.*, 20(1):59–69 (1997)); trachoma (Conway et al., *Infect. Immun.*, 65(3): 1003–6 (1997)); autoimmune diseases, inluding autoimmune dacryoadenitis (Takahashi et al., *Clin. Exp. Immunol.*, 109(3):555–61 (1997)), autoimmune uveoretinitis (Thillaye-Goldenberg et al., *J. Neuroimmunol*, 110(1–2):31–44 (2000)) and AIDS (Lin et al., *Curr. Eye Res.*, 16(10):1064–8 (1997)) and autoimmune sialoadenitis (Mustafa et al., *Clin. Exp. Immunol.*, 112(3):389–96 (1998)); scieritis (Di Girolamoet al., *Am. J. Pathol.*, 150(2):653–66 (1997)); rheumatic diseases, such as systemic lupus erythematosus, rheumatoid arthritis (al-Janadi et al., *J. Clin. Immunol.*, 13(1):58–67 (1993), as mentioned above, rheumatic heart disease (Miller et al., *J. Rheumatol.*, 1989) and rheumatoid vasculitis (Flipo et al., *Ann. Rheum. Dis.*, 56(1):41–4 (1997)); optic neuropathy (Madigan et al., *Neurol. Res.*, 18(3):233–6 (1996)); ocular toxoplasmosis (Davidson et al., *Antimicrob. Agents Chemother.*, 40(6):1352–9 (1996)); vitroretinal disorders (Esser et al., *Ger. J. Ophthalmol.*, 4(5): 269–74 (1995)); neovascular eye diseases (Spranger et al., *Med. Klin.*, 90(3): 134–7 (1995); endocrine orbitopathy (Heufelder et al., *Med Klin.*, 88(4):181–4 (1993)); granulocyte-macrophage colony stimulating factor GM-CSF disease (Lang et al., *Growth Factors*, 6(2):131–8 (1992)); non-neoplastic diseases (Billington, *Drug Des. Discov.*, 8(1):3–35 (1991)); Wegener's granulomatosis (Mayet et al., *J. Immunol. Methods*, 143(1): 57–68 (1991)); keratoconus (Fabre et al., *Curr. Eye Res.*, 10(7):585–92 (1991)); intraocular tumors (Wong et al., *Cornea*, 10(2):131–5 (1991)) such as intraocular melanomas (Ma et al., *Invest. Ophthalmol. Vis. Sci.*, 39(7):1067–75 (1998)), retinoblastoma (Detrick et al., *Invest. Ophthalmol. Vis. Sci.*, 32(6):1714–22 (1991)) and colorectal carcinoma (Kemeny et al., *Cancer*, 66(4):659–63 (1990)); nasal polyp disease (Saji et al., *Auris Nasus Larynx*, 27(3):247–52

(2000)); cholesteatoma (Amar et al., *J. Laryngol Otol.*, 110(6):534–9 (1996); thrombotic thrombocytopenic purpura and hemolytic-uremic syndrome (Mauro et al., *Am. J. Hematol.*, 66(1):12–22 (2001)); Still's disease (Cavagna et al., *Clin. Exp. Rheumatol.*, 19(3):329–32 (2001)); tonsillar hypertrophy and recurrent tonsillitis (Agren et al., *ORL J. Otorhinolaryngol Relat. Spec.*, 60(1):35–41 (1998)), psoriasis (Mizutani et al., *J. Dermatol. Sci.*, 14(2):145–53 (1997)); mononucleosis (Andersson et al., *Clin. Exp. Immunol.*, 92(1):7–13 (1993)); autoimmune encephalomyelitis (Weissert, *J. Immunol.*, 166(12):7588–99 (2001)), chronic proliferative dermatitis (HogenEsch et al., *J. Immunol.*, 162(7): 3890–6 (1999)); retinal vein occlusion (Conway et al., *Int. Ophthalm.*, 19(4):249–52 (1995)); Irvine-Gass Syndrome; and age-related macular degeneration (Abe et al., *Tohoku J. Exp. Med.*, 189(3):179–89 (1999)). Other specific examples of inflammation-associated diseases that may be treated according to the invention include autoimmune diseases that affect the eyes, nose, throat or ear, such as the autoimmune disease that affects upper and lower respiratory tracts, Wegener's granulomatosis (Hewins et al., *Curr. Opin. Rheumatol.*, 12(1):3–10 (2000); Yi et al., *Semin. Diagn. Pathol.*, 18(1): 34–46 (2001)), and the autoimmune disease that affects sight, smell and taste, Sjogrens syndrome (Carsons, S., *Am J. Manag. Care*, 7(14): S433–43 (2001); Lash et al., *Nurse Pract.*, 26(8):50 (2001)). More specifically, inflammatory diseases that affect joints such as the systemic inflammatory rheumatic disease involving spinal and sacroiliac joints, ankylosing spondylitis (Toussirto et al., *Expert Opin. Investig. Drugs*, 10(1):21–9 (2001)), the inflammatory joint diseases, spondyloarthropathies (Braun et al., *Curr. Opin. Rheumatol*, 8(4):275–87 (1996); Gladman, D D, *Am. J. Med Sci.*, 316(4):234–8 (1998))), the joint and spine-affected arthritis, psoriatic arthritis (Gladman et al., *Expert Opin. Investig. Drugs*, 9(7):1511–22 (2000); Scarpa et al., *Curr. Opin. Rheumatol.*, 12(4):274–80 (2000)) and joint disorders such as temporomandibular joint disorder (Stack et al., *Am. Fam. Physician*, 46(1):143–50 (1992)) are included.

Further examples of diseases that may be treated according to the invention include diseases associated with the oral airway such as molar extractions, chemotherapy related mucosal injury (Spijkervet et al., *Curr. Opin. Oncol.*, 10 (Suppl. 1):S23–7 (1998); Khan et al., *J. Natl. Cancer Inst. Monogr.*, 29:31–6 (2001)), non-infections lung injury following bone marrow transplant, such as respiratory distress syndrome (Hite et al., *Drugs*, 61(7):897–907 (2001)) and bronchiolitis obliterans pneumonia (Nagai et al., *Curr. Opin. Pulm. Med.*, 2(5):419–23 (1996); Epler, G R, *Semin. Respir. Infect.*, 10(2):65–77 (1995)).

TNF-α and IL-1 Modulation as Therapeutic Approaches

Prior to the isolation of TNF-α, the employed therapeutic approaches to the above diseases were targeting the reduction of chronic inflammation and were based on steroidal and non-steroidal anti-inflammatory treatment. However, our recent understanding of TNF-α has led to the development of alternative strategies based on its selective inhibition. These general strategies are summarized below.

Steroidal treatment. This treatment, which includes the use of corticosteriods, causes the reduction in the number and the activity of the immune-system cells, the mechanism of action of the corticosteroids involves crossing of the plasma membrane and binding on receptors in the cytosol. The resulting complexes are then transported to the cell nucleus where they bind to specific regulatory DNA sequences, thereby down-regulating the cytokine production. Although currently employed, this strategy has several disadvantages since it is not specific for TNF-α but also down-regulates several other cytokines that may play important roles in an effective immune reaction. Moreover, use of steroids is also implicated with the development of cancer (for example prostate cancer).

Non-steroidal anti-inflammatory treatment. This strategy includes use of compounds such as aspirin that indirectly reduce inflammation. This is usually accomplished by inhibiting the cyclooxygenase pathway by which prostaglandins and thromboxanes are produced. This action reduces the vascular permeability and provides temporary relief. To this end, this strategy does not regulate the production of cytokines and has little or no effect in diseases associated with chronic inflammation.

Engineered monoclonal anti-TNF antibodies. This strategy involves a selection of monoclonal antibodies that are capable of binding to and neutralizing TNF-α. Although the preliminary clinical studies have shown some positive results, this approach is still in its infancy and not generally accepted. One of the problems to be addressed is that the monoclonal antibodies are of murine origin and in humans they elicit anti-immunoglobulin immune responses which limit their clinical use. Recombinant engineering techniques are being pursued to create "humanized" versions of the rodent antibodies that will maintain activity against TNF-a and will be accepted more easily by the human immune system.

Use of soluble TNF-α receptors. The use of soluble receptors against TNF-α is a new therapeutic approach. Although these receptors are created to bind and neutralize TNF-α, they also enhance its activity by prolonging its lifespan in blood circulation. Furthermore, the long term immunological response to this type of treatment is being evaluated.

Gene therapy. The goal of this approach is to decrease inflammation not by decreasing the expression of TNF-α but by increasing the local production of anti-inflammatory cytokines. The treatment consists of direct injection of cDNA expression vectors encoding for anti-inflammatory cytokines to the inflamed area, which could antagonize the effect of TNF. The efficacy of this method is currently under investigation in preclinical studies and its long term effects on the immune response remain unknown.

Other disease states and conditions. Additionally, TNF-α and/or IL-1 have been more recently identified as participating in modulating angiogenic vascular endothelial growth factor (VEGF), see E. M. Paleolog et al., *Arthritis & Rheumatism*, 41, 1258 (1998), and may participate in tuberculous pleurisy, rheumatoid pleurisy, and other immune disorders, see T. Söderblom, *Eur. Respir. J.*, 9, 1652 (1996). TNF-α has also been reported to effect expression of certain cancer cell genes for multidrug resistance-associated protein (MRP) and lung resistance protein (LRP), see V. Stein, *J. Nat. Canc. Inst.*, 89, 807 (1997), and to participate in chronic and congestive heart failure, and related cardiovascular disease, see for example R. Ferrari, *Cardiovascular Res.*, 37, 554 (1998); C. Ceconi et al., *Prog. Cardiovascular Dis.*, 41, 25 (1998), and to either directly or indirectly mediate viral infection, see D. K. Biswas, et al., *J. Acquired Immune Defic Syndr. Hum Retrovirol.*, 18, 426–34 (1998) (HIV-1 replication); R. LeNauor, et al., *Res. Virol.*, 145, 199–207 (1994) (same); T. Harrer, et al., *J. Acquir. Immune Defic. Syndr.*, 6, 865–71 (1993) (same); E. Fietz, et al., *Transplantation*, 58 (6), 675–80 (1994) (human cytomegalovirus (CMV) regulation); D. F. Zhang, et al., *Chin. Med. J.*, 106, 335–38 (1993) (HCV and HBV infection). Furthermore, antagonists of TNF-α have also been shown useful in the treatment of skin redness of a neurogenic origin. See European Patent EPO-774250-B1 (to De Lacharriere et al.).

TNF-α has also been identified as expressed at heightened levels in humans diagnosed as obese or exhibiting insulin resistance, and is thus, a modulator of diabetes. See Hotamisligil, G., Arner, P., Atkuinson, R., Speigelman, B. (1995), "Increased adipose tissue expression of tumor necrosis factor-α (TNF-α) in human obesity and insulin resistance. *J. Clin. Invest.* 95:2409–2415. TNF-α has also been identified as an important modulator of transplant rejection. See Imagawa, D., Millis, J., Olthoff, K., Derus, L., Chia, D., Sugich, L., Ozawa, M., Dempsey, R., Iwaki, Y., Levy, P., Terasaki, P., Busuttil, R. (1990) "The role of tumor necrosis factor in allograft rejection" *Transplantation*, vol. 50, No. 2, 219–225.

Pharmaceutical Compositions

The present invention includes pharmaceutical compositions useful in the treatment of various diseases and disease states. Such disclosed pharmaceutical compositions may comprise a pharmaceutically acceptable carrier or diluent, well known in the pharmaceutical art and described, for example, in Remington's Pharmaceutical Sciences, Mack Publishing Co. (A. R. Gennaro edit. 1985) and a pharmaceutically effective amount of a chemical compound. Such compositions may further comprise preservatives, stabilizers, dyes, flavoring agents, antioxidants and suspending agents. Further disclosed herein are various pharmaceutical compositions well known in the pharmaceutical art for uses that include intraocular, intranasal, and intraauricular delivery. Pharmaceutical formulations for intraocular delivery include aqueous ophthalmic solutions of the active compounds in water-soluble form, such as eyedrops, or in gellan gum (Shedden et al., *Clin. Ther.*, 23(3):440–50 (2001)) or hydrogels (Mayer et al., *Ophthalmologica*, 210(2):101–3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29–45 (1994)), lipid-soluble formulations (Alm et al., *Prog. Clin. Biol. Res.*, 312:447–58 (1989)), and microspheres (Mordenti, *Toxicol. Sci.*, 52(1):101–6 (1999)); and ocular inserts. Suitable pharmaceutical formulations for intraocular delivery are most often and preferably formulated to be sterile, isotonic and buffered for stability and comfort. Pharmaceutical compositions for intranasal delivery include drops and sprays often prepared to simulate in many respects nasal secretions to ensure maintenance of normal ciliary action. As disclosed in Remington's Pharmaceutical Sciences (Mack Publishing, 18$^{th}$ Edition), and well-known to those skilled in the art, suitable nasal formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

Methods of Administration

The present invention includes methods for administering the disclosed chemical compounds and the disclosed pharmaceutical compositions. Such disclosed methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the invention into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

These observations highlight the importance and desirability of identifying novel strategies and/or novel compounds and classes of compounds that selectively influence the production of TNF-α and/or IL-1. Small molecules that selectively inhibit these cytokines are therefore particularly medicinally and biologically important in, for example, maintaining an active immune system and in treating inflammation based diseases.

Preferred Methods of Synthesis of the Present Invention

Certain embodiments of the invention include novel methods of making the compounds having the chemical structure of Formulae (II), (IIA), or (IIB), as well as novel methods of making known analogs of the known the compounds having the chemical structure of Formulae (II), (IIA), or (IIB), for example, the compounds of Formulae (I) and (IA).

The compounds of the present invention, and specifically, the compounds having the chemical structure of Formula (II), (IIA), or (IIB), may be prepared either synthetically or semi-synthetically. If prepared synthetically, commonly available starting materials may be used, including, but not limited to bicyclic compounds having reactive halide moieties. The at-least-three-ringed compounds of the present invention may be synthesized according to various ring closure reactions. Such reactions include, but are not limited to the Diels-Alder reaction, and the Dieckmann Condensation reaction. The Diels-Alder reaction preferably involves the reaction of a diene and an a substituted alkenyl moiety, such that the third ring of the desired compound is formed. The Dieckmann Condensation reaction may be preferably followed by the reduction of the resulting cycloketone moiety. Compounds of the present invention may be purified and isolated, following such synthetic methods and other well-known synthetic methods, by use of procedures, such a chromatography or HPLC, as well known to those skilled in the art.

Alternatively, according to the present invention, the compounds having the chemical structure of Formulae (I) and (IA), and certain specific analogs and derivatives thereof, may be extracted and isolated, at least in the form of a crude extract comprising acanthoic acid, from the root bark of *Acanthopanax koreanum* Nakai. Such an extract may preferably be produced according to the following method:

Approximately one kilogram of dried root bark of *A. koreanum* Nakai is obtained, chipped, and covered with between 1 L to 3 L, and preferably 2 L, of a suitable solvent, most preferably methanol. This mixture is maintained at a temperature ranging from 20° to 60°, and may be maintained at room temperature, for at least 10 hours, and preferably for 12 hours. The mixture is then filtered to remove and retain the filtrate. This procedure is repeated, preferably at least two additional times, and the combined filtrates are concentrated under a reduced pressure to obtain an extract.

Approximately 100 grams of the extract is partitioned with 200 mL to 400 mL, preferably 300 mL, of an aqueous solution, preferably water and 200 mL to 400 mL, preferably 300 mL, of an organic solution, preferably diethyl ether. The organic fraction is separated therefrom and then concentrated under a reduced pressure to obtain a further extract. Said further extract is purified, preferably by column chromatography and even more preferably by use of a silica gel column, using a mixture of suitable organic solvents, preferably hexane and ethyl acetate as an eluent to obtain isolated acanthoic acid.

This isolated compound of Formulae (I) and (IA) may then by synthetically modified to yield certain compounds of the present invention, specifically the compounds having the chemical structure of Formula (II) or (IIA). For example, ester $R_1$ analogs of acanthoic acid may be formed according to acid-catalyzed nucleophilic addition of an alkyl alcohol to the carboxylic acid moiety of acanthoic acid. Ether $R_1$ analogs of acanthoic acid may be formed from either primary alkyl halides or alcohols according to the Williamson Ether synthesis, or via the reduction of a primary alcohol moiety. Alkyl, alkenyl, and alcoholic $R_{10}$ analogs of acanthoic acid may be formed via catalytic hydrogenation of the alkenyl group, or via electrophilic addition of, preferably, HCl or HBr or other suitable alkyl halides. Substitution analogs at the other R positions of acanthoic acid may be formed by displacement reactions involving alkyl halides, provided suitable reactive groups and related protecting groups are employed to encourage the desired reaction. According to these reaction and other well-known synthetic reactions, the production of the full range of the compounds of the present invention, given the description of those compounds provided herein, is within the skill of those of the art.

Fully-synthetic approaches for the preparation of the compounds of the invention, including compounds of general Formulae (I), (IA), (II), (IIA), and (IIB) are described herein. This synthesis includes one or more retrosynthetic analyses of acanthoic acid and its analogs, syntheses of radioactively labeled acanthoic acid and its analogs, syntheses of dimers and conjugates of the compounds of general Formulae (I), (IA), (II), (IIA), and (IIB). Those of skill in the art will also appreciate that these approaches are also fully applicable to the preparation of kauranoic acid and its analogs.

The Compound of Formula (I) and its Naturally-Occuring Analogs

The root bark of *Acanthopanax koreanum* Nakai (Araliaceae), which is found indigenously in Cheju Island, The Republic of Korea, has been used traditionally as a tonic and sedative, as well as a remedy for the treatment of rheumatism and diabetes. During their investigation of this folk medicine, Chung and coworkers identified from its pharmacologically active extracts two novel tricyclic diterpenes: acanthoic acid (Compound 1) and its methyl ester (Compound 2), as depicted in FIG. 1. See Kim, Y. H.; Chung, B. S.; Sankawa, U. "Pimaradiene diterpenes from *Acanthopax Koreanum*". *J Nat. Prod.* 1988, 51, 1080–1083. Acanthoic acid is a pimarane (3). However, in sharp contrast to the other members of the pimaranes family, 1 is distinguished by an unusual stereochemical relationship between the C8 and C10 centers that provides a unique mode of connectivity of the BC ring system.

Prior to this invention, no complete chemical synthesis existed for production of the chemical having the structure of Formula (I) or its analogs. Importantly, the chemical structure of Formula (I), 1, (FIG. 1) possesses a biological profile as an anti-inflammatory agent. More specifically, in vitro studies with activated (inflammed) monocytes/macrophages revealed that treatment with 1 (approximately 0.1 to approximately 1.0 microgram/ml for 48 hours) leads to an approximately 90% inhibition of the TNF-α and IL-1 production. This inhibition was concentration dependent and cytokine-specific, since under the same conditions the production of IL-6 or IFN-γ (interferon-gamma) were not affected. The in vivo effects of acanthoic acid were evaluated in mice suffering from silicosis (chronic lung inflammation) and cirrhosis (liver inflammation and hepatic fibrosis). Histologic analysis revealed that treatment with compound 1 led to a substantial reduction of fibrotic granulomas and a remarkable recovery of the cirrotic liver cells. These dramatic results can be attributed, at least partially, to inhibition of pro-inflammatory cytokines, such as TNF-α and IL-1, mediated by 1. Compound 1 also shows very little toxicity in mice and only upon orally administering a high concentration (LD>300 mg/100 g of body weight). See Kang, H.-S.; Kim, Y.-H.; Lee, C.-S.; Lee, J.-J.; Choi, I.; Pyun, K.-H., *Cellular Immunol.* 1996, 170, 212–221. Kang, H.-S.; Song, H. K.; Lee, J.-J.; Pyun, K.-H.; Choi, I., *Mediators Inflamm.* 1998, 7, 257–259.

The chemical structure of Formula (I) thus has potent anti-inflammatory and anti-fibrotic effects and reduces the expression of TNF-α and IL-1. Acanthoic acid is thus used as a chemical prototype for the development of the novel compounds of the invention.

Retrosynthetic Analyses of the Compounds of Formulae (I), (II) and (IIB)

Figure 2:
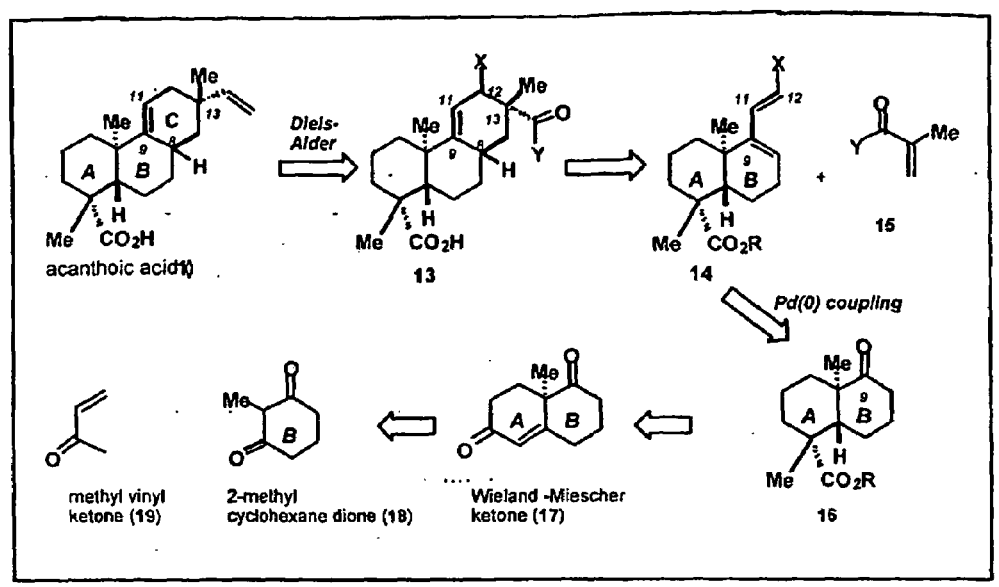
FIG. 2 depicts the retrosynthetic analysis and strategic bond associations of certain compounds of the invention.

The compounds of Formulae (I), (II) and (IIB), and preferably the compound of Formula (I) and compounds of Formulae (IIB) designated TTL1, TTL2, TTL3, and TTL4 herein, the may be synthesized according to an aspect of the invention. The bond disconnections of the compounds of Formulae (I) are shown in FIG. 2. The novel structural arrangement of the BC rings and the presence of the quaternary C13 center constitute an unusual motif and lead to a novel strategy that is one aspect of the invention. This motif is fixed, in one step, into the desired stereochemistry by employing a Diels-Alder methodology. A diene, for example, 14, and a dienophile, such as 15 (Y: oxazolidinone-based auxiliary), were identified as the appropriate starting materials for an endo selective Diels-Alder reaction. To further ensure the desired regiochemical outcome of this cycloaddition, diene 14 was functionalized transiently with a heteroatom (for example, X=OTBS or SPh), which will be subsequently removed from the product 13. The generally observed endo preference of this reaction was used to predict the stereochemical relationship between the C12 and C13 centers as shown in product 13, while the diastereofacial seletivity of the process will be controlled either by a chiral auxiliary at the carbonyl center of the dienophile or by using a chiral catalyst. See Xiang, A. X.; Watson, D. A.; Ling. T.; Theodorakis, E. A. "Total Synthesis of Clerocidin via a Novel, Enantioselective Homoallenylboration Methodology". *J. Org. Chem.* 1998, 63, 6774–6775.

Diene 14 may be formed by a palladium (0) catalyzed construction of the C8–C11 bond, revealing ketone 16 as its synthetic progenitor. This ketone was formed from the known Wieland-Miescher ketone (17), which in turn was readily available by condensation of methyl vinyl ketone (19) with 2-methyl 1,3-cyclohexane dione (18) (FIG. 2).

Figure 5:
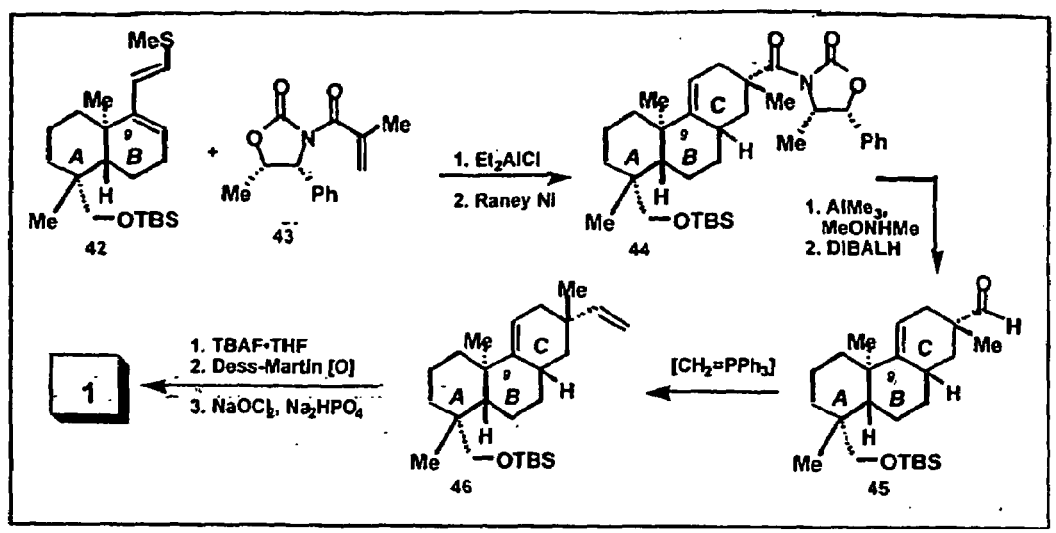
FIG. 5 depicts a synthetic scheme (Scheme 2) by which the synthesis of acanthoic acid and certain compounds of the invention may be completed.
Figure 6:
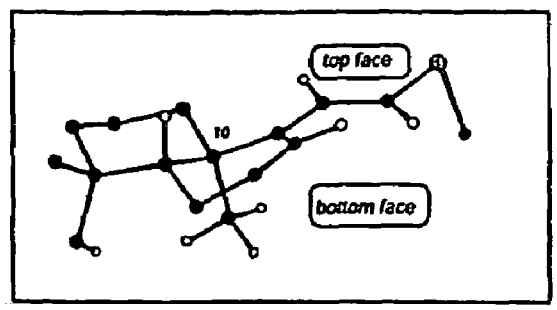
FIG. 6 depicts the minimized, three-dimensional model of diene 42, as described in the detailed description of the invention.
Figure 7:
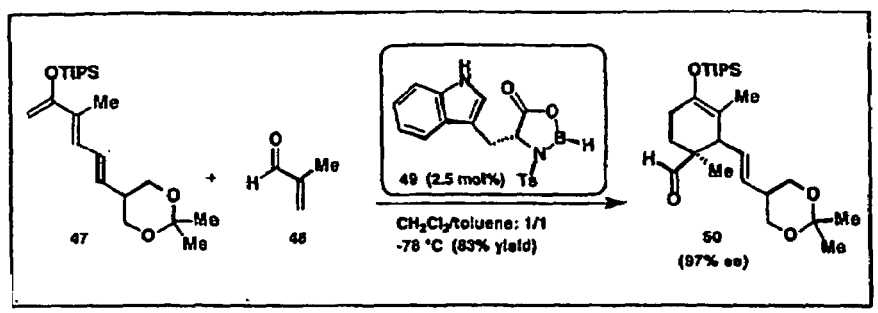
FIG. 7 depicts a synthetic scheme (Scheme 3) for the development and application of catalyst 49, as described in the detailed description of the preferred embodiment of the invention, an asymmetric Diels-Alder reaction.

In one aspect of the invention, it is recognized that the functionalities and relative stereochemistry of the AB ring system of acanthoic acid (1) are akin to those in the structure of podocapric acid (20). See "The total synthesis of natural products." ApSimon, Ed.; John Wiley & Sons, Inc., 1973, Volume 8, pages 1–243. Among the several synthetic strategies toward 20, highlights of the ones may be are relevant to our proposed synthesis of 1 are shown in FIG. 5. According to the invention, these approaches allowed the prediction of the stereochemical outcome of the synthesis of The compounds of Formulae (I), (II) and the contrary stereochemical of the compounds of Formulae (IIB), and the compounds of Formulae (IIB) that are designated TTL1, TTL2, TTL3, and TTL4 herein.

Complete Syntheses of the Compounds of Formulae (I), (II) and (IIB)

Figure 3:
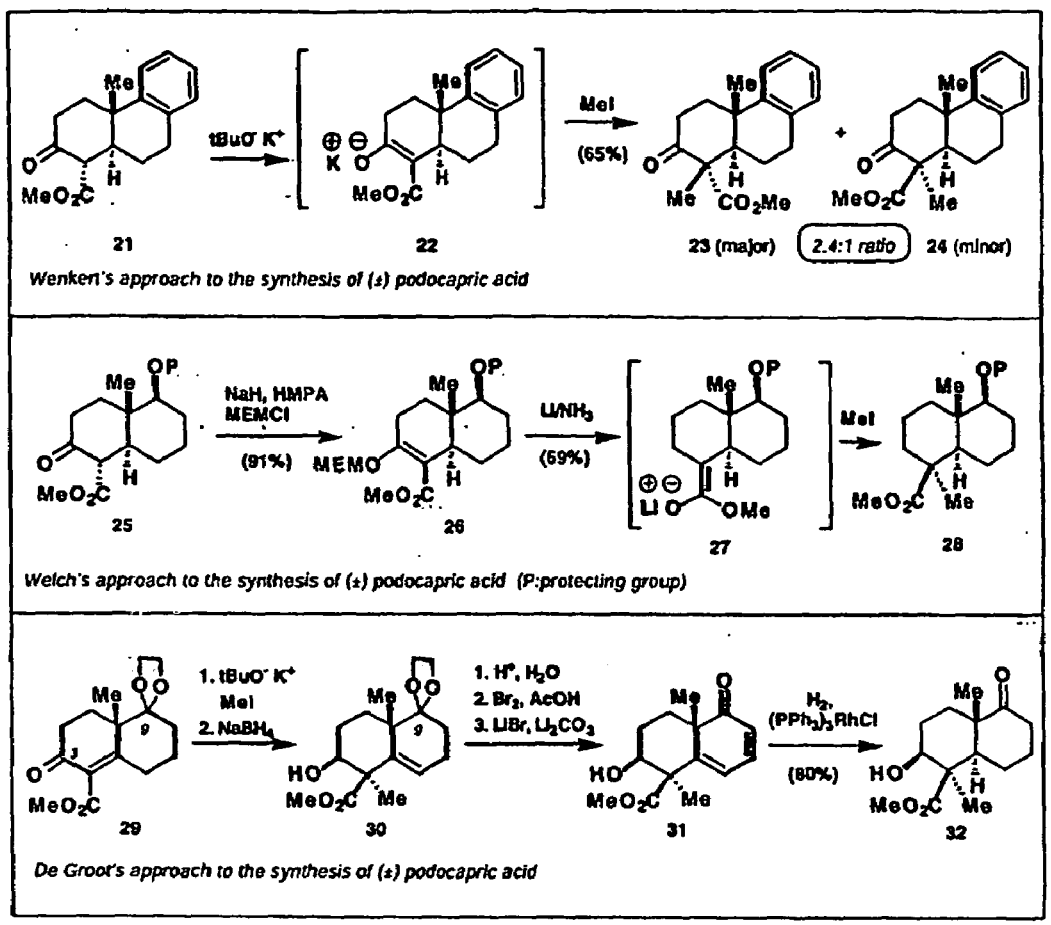
FIG. 3 depicts selected approaches to the construction of the AB ring of certain compounds of the invention including: Wenkert's approach to the synthesis of (±) podocapric acid; Welch's approach to the synthesis of (±) podocapric acid; and DeGrot's approach to the synthesis of (±) podocapric acid.

The initial step of the synthesis of acanthoic acid (1), and of all compounds of Formulae (I), (II) and (IIB), involves the reaction of a Wieland-Miesher ketone (17). This compound was readily available from compounds 18 and 19 as a single enantiomer by a Michael addition/Robinson annulation sequence using catalytic amounts of (R)-proline. Selective protection of the more basic C9 carbonyl group of 17, followed by a reductive alkylation of enone 34 with methyl cyanoformate gave rise to ketoseter 36. Transformation of 36 to 39 was based on previous studies, see Welch, S. C.; Hagan, C. P. "A new stereoselective method for developing ring A of podocapric acid compounds" *Synthetic Commun.* 1972, 2, 221–225, as depicted in FIG. 3. Reduction of the ester functionality of 39, followed by silylation of the resulting alcohol and acid-catalyzed deprotection of the ketal unit then afforded ketone 40. Conversion of 40 to the desired diene 42 was accomplished by a two step sequence involving transformation of 40 to its corresponding enol triflate derivative, followed by palladium catalyzed coupling with vinyl stannane 41. See Farine, V.; Hauck, S. I.; Firestone, R. A. "Synthesis of cephems bearing olefinic sulfoxide side chains as potential b-lactamase inhibitors" *Bioorg. & Medicinal Chem. Lett.* 1996, 6, 1613–1618.

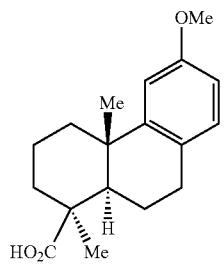

podocapric acid (20)

The steps that were used in the completion of the synthesis of acanthoic acid (1), and are used in the completion of the syntheses of compounds of Formulae (I), (II) and (IIB) are depicted in FIG. 5, as Scheme 2. A Diels-Alder cycloaddition between diene 42 and dienophile 43, followed by reductive desulfurization with Raney Ni produces the tricyclic system 44 with the desired stereochemistry. Transformation of 44 to the Weinreb amide, followed by reduction with DIBALH generated aldehyde 45, which upon Wittig reaction gave rise to olefin 46. Fluoride-induced desilylation of 46, followed by a two steps oxidation of the resulting alcohol to the carboxylic acid produced acanthoic acid (1), and may be used to produce the compounds of Formulae (I), (II) and (IIB) by appropriate substitution of the intermediates.

One important step to the synthesis of compounds of Formulae (I) and (IA), and the compounds of Formulae (II), (IIA) and (IIB), is the Diels-Alder reaction. This reaction, and the use and selection of one or more appropriately substituted dienes and/or dienophiles permits the selective synthesis of compounds of Formula (II) or the selective synthesis of compounds of Formula (IIB). For example, the following preferred dienophiles may be used in place of the dienophiles, for example, compound 43 and pimarane (103), as depicted herein in, for example, FIGS. 5, 7, 8, 21, and 23, as Reaction Schemes 2, 3, 4, 5, and 6, to selectively yield compounds of Formulae (II) and (IIB). Exemplary dienophiles include those of Formulae (III):

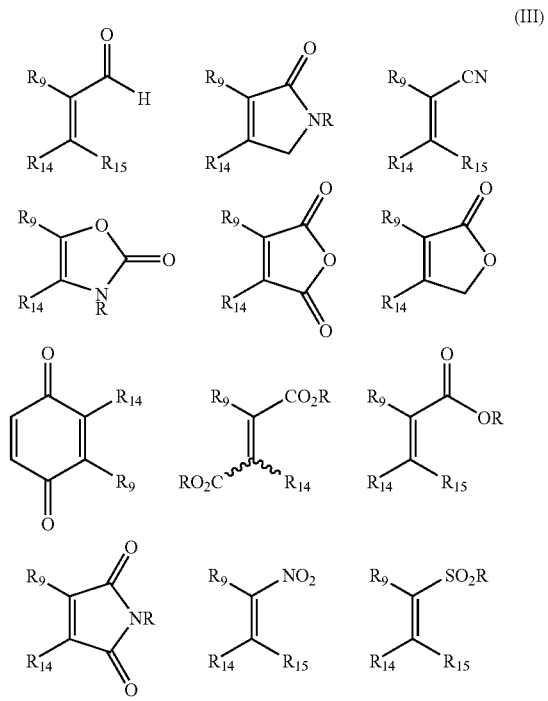

(III)

wherein the numbered R-groups ($R_9$, $R_{14}$, and $R_{15}$) are as designated above for the compounds of Formula (IIB), and the unnumbered R groups may be any of $R_1$ through $R_{15}$ as designated above for the compounds of Formula (IIB).

Furthermore, the electronic conformation of the diene, for example compound (42) and compound (112), as depicted herein in, for example, FIGS. 5, 7, 8, 21, and 23, as Reaction Schemes 2, 3, 4, 5, and 6, respectively, may be altered by the covalent linkage of electron-donating or electron-withdrawing group, for example, pHS, to the diene. As exemplified herein, such a covalently linked electron-donating or electron-withdrawing group effects the orientation of the incoming dieneophile.

Thus, according to one aspect of the invention, the chiral nature of diene 42 allows it to be used to induce asymmetry during the cycloaddition. Examination of a minimized model of 42 indicates that the angular methyl at ClO influences the facial selectivity of the reaction and allow more efficient approach of the dienophile from the top face of the diene. This approach produced the adduct that leads to compounds of Formulae (IIB). This approach also allowed for the development of a catalytic asymmetric variant of the Diels Alder reaction. The benefits of using chiral catalysts, as opposed to chiral auxiliaries, are obvious and well documented in the recent literature.

One preferred embodiment of the invention is the use of catalyst 49, that was developed and applied by Corey toward an improved asymmetric synthesis of cassiol (Scheme 3). See Corey, E. J.; Imai, N.; Zhang, H.-Y. *J. Am. Chem. Soc.* 1994, 116, 3611. Compound 49 was shown to allow Diels-Alder cycloaddition of an electronically rich diene 47 with methacrolein (48) and produce exclusively the endo adduct in excellent yield and enantiomeric excess (83% yield, 97% ee).

Figure 8:
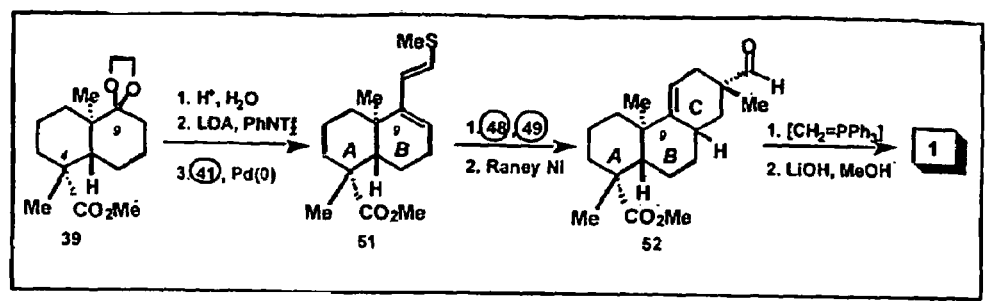
FIG. 8 depicts a synthetic scheme (Scheme 4) for the synthesis of the compound of Formula (I) and certain compounds of the invention based on an asymmetric Diels-Alder methodology.

Application of the above methodology to our synthesis is depicted in FIG. 8, as Scheme 4. Use of catalyst 49 provided additional versatility and significantly shorten the total amount of steps required for completion of the total synthesis of 1.

Synthesis of Radiolabeled Compounds of Formula (I)

Figure 4:
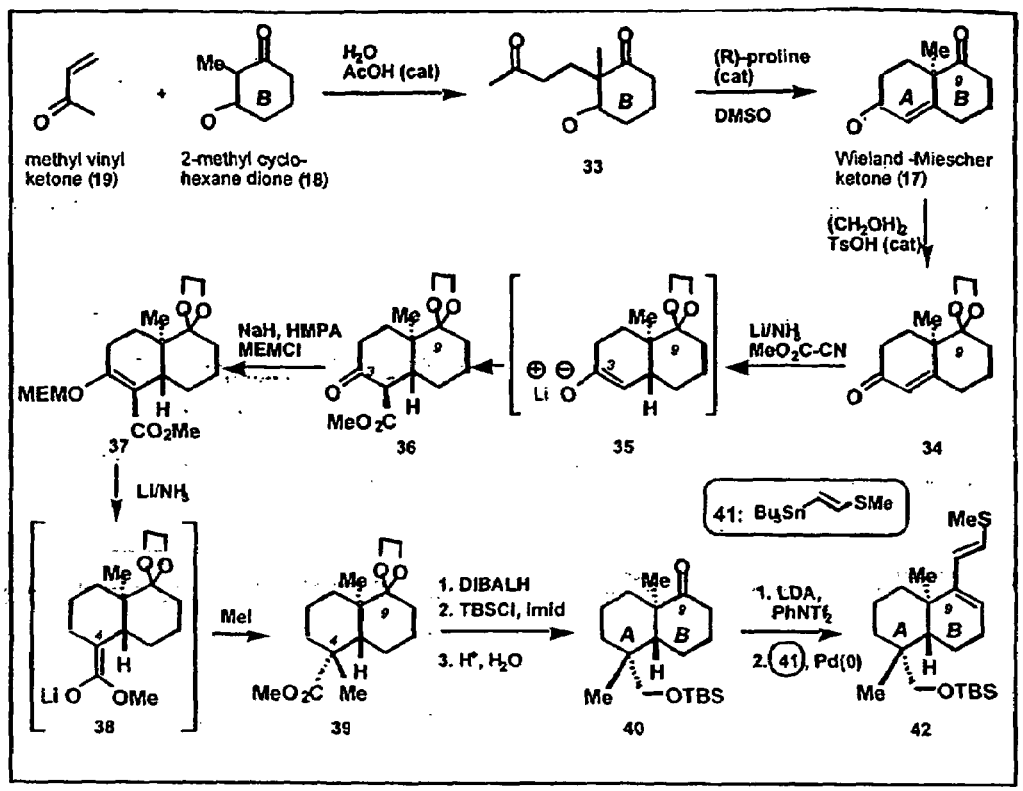
FIG. 4 depicts a schematic synthetic scheme (Scheme 1) of the synthesis of the AB ring system of acanthoic acid and certain compounds of the invention.

A radiolabeled sample of a compound of Formulae (I), (II), (IIA) or (IIB) may be synthesized and is useful in pharmacological and pharmacokinetic studies, For example, a C14-labeled methylene carbon is incorporated on the compound of Formulae (I) using aldehyde 52 as a starting material (as depicted in FIG. 4, Scheme 4). The C14-labeled yield, required for the Wittig chemistry, is prepared in two steps from C14-labeled iodomethane and triphenyl-phosphine, followed by treatment with a base, such as NaHMDS. Base-induced deprotection of the methylester produces radiolabeled a compound of Formulae (I), (II), (IIA) or (IIB).

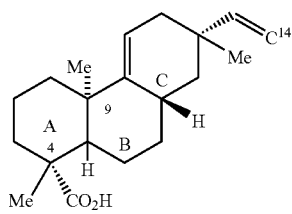

1*: $^{14}$C labeled acanthoic acid

Objectives of the Syntheses of the Compounds of Formula (II), (IIA) and (IIB)

One aspect of the invention is the identification of novel anti-inflammatory drugs having the structure of the compounds of Formula (II), (IIA) and (IIB). Biological screening of synthetic intermediates and rationally designed compounds of Formula (II) provide information and guide the design requirements.

The design and synthesis of analogs of the compounds of Formula (II) is based on the following objectives: (a) defining the minimum structural and functional requirements the compounds of Formula (II) that are responsible for the TNF-α and IL-1 modulating activity (minimum pharmacophore); (b) improving the TNF-α and IL-1 modulating activity of the compounds of Formula (II) by altering the structure, particularly the R-groups of the minimum pharmacophore (for example, SAR studies and molecular recognition experiments); (c) examining the mode of action of the compounds of Formula (II) by photoaffinity labeling studies; (d) modifying and improving the solubility and membrane permeability of the compounds of Formula (II);

(e) synthesizing and study dimers or conjugates of the compounds of Formula (II); selective delivery units and (f) redesigning and refining the target structure by evaluating the obtained biological data.

Figure 9:
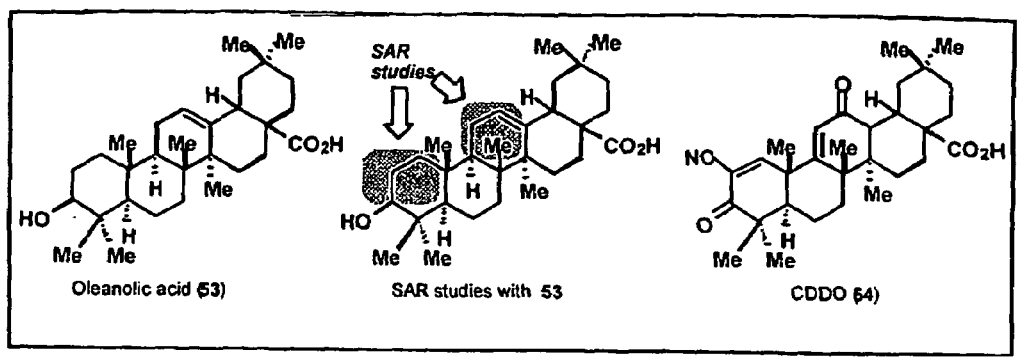
FIG. 9 depicts the structure activity relationship and the focus of structure activity relationship studies of oleanolic acid and its derivatives and certain compounds of the FIG. 10 depicts sites identified for the structural alteration and structure activity relationship studies of Compound 1.

Of particular significance to the rational design of novel the compounds of Formulae (II), (IIA) and (IIB) are the recent reports that modification of the A and C rings of oleanolic acid (53), as depicted in FIG. 9, lead to enhanced antiproliferative and antiinflammatory activity. See Honda, T.; Rounds, B. V.; Gribble, G. W.; Suh, N.; Wang, Y.; Sporn, M. B. "Design and synthesis of 2-cyano-3,12-dioxolean-1, 9-dien-28-oic acid, a novel and highly active inhibitor of nitric oxide production in mouse macrophages" *Biorg. & Medic. Chem. Lett.* 1998, 8, 2711–2714. Suh, N. et al "A novel synthetic oleanane triterpenoid, 2-cyano-3,12-dioxoolean-1,9-dien-28-oic acid, with potent differentiating, antiproliferative and anti-inflammatory activity" *Cancer Res.* 1999, 59, 336–341. More specifically, SAR studies with commercially available 53 and semisynthetic derivatives thereof have led to the recognition that that: (a) attachment of electron-withdrawing groups, such as nitrile, at the C2 position increases the biological potency of 53 (FIG. 9); (b) an α,β unsaturated ketone functionality at the C ring is a strong enhancer of potency. The combination of these observations lead to the semisynthesis of a designed triterpenoid 54 (FIG. 9), shown to be 500-fold more active than any other known triterpenoid in suppressing the inflammatory enzymes iNOS (inducible nitric oxide synthase) and COX-2 (cyclooxygenase-2) (FIG. 9).

Synthesis of the Compounds of Formulae (II), (IIA) and (IIB)

Figure 10:
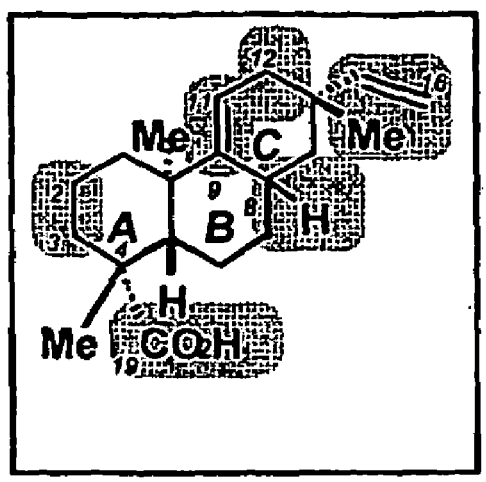
Figure 11:
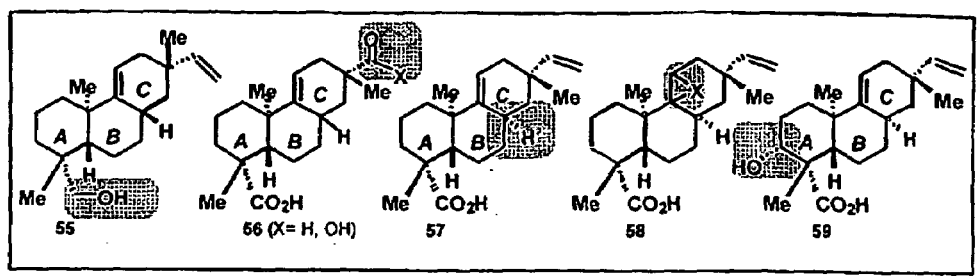
FIG. 11 depicts preferred, representative examples of analogs of Compound 1 for use in structure activity relationship studies and chemical biological studies.

The thirteen-step synthesis of the compounds of Formulae (II), (IIA) and (IIB) (as shown in FIGS. 4 and 8, Schemes 1 and 4, respectively) is efficient and as such, it allows the preparation of a variety of analogs useful in SAR studies. The biological significance of the unusual tricyclic scaffold of the compounds of Formulae (II), (IIA) and (IIB) (the C8 epimer is constructed using the appropriate Diels-Alder catalyst). The sites that are easily altered via the synthetic approach of the invention, or by standard modifications of our synthetic intermediates are shown in the FIG. 10, and representative examples of the compounds of Formula (II) are shown in FIG. 11.

The desired chemical scaffold of the compounds of Formula (II), (IIA) and (IIB) may also be incorporated into solid support such as, for example, a Wang resin. This permits the facile construction of combinatorial libraries of the compounds of Formula (II), (IIA) and (IIB). Furthermore, according to the invention, preferred TNF-α and IL-1 modulators may be more rapidly identified and screen that currently possible.

Figure 12:
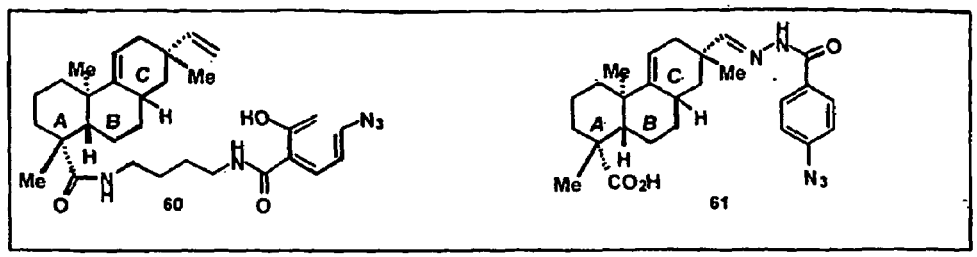
FIG. 12 depicts certain preferred, representative derivatives of Compound 1 for photo affinity labeling studies.
Figure 13:
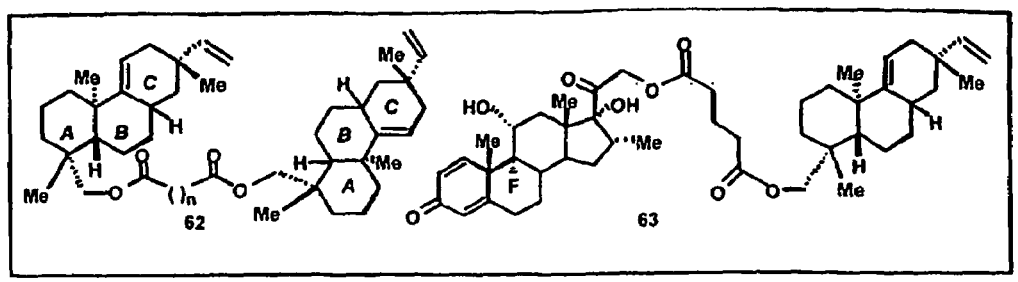
FIG. 13 depicts certain preferred, representative examples of dimers and/or conjugates of Compound 1.

Photoaffinity labeling studies. The backbone of the compounds of Formula (II), (IIA) and (IIB) is also preferably labeled with a reactive cross-linker, that is useful in photoaffinity labeling studies. These studies assist in the identification of the in vivo target of the compounds of Formula (II), (IIA) and (IIB) and provide fundamental insights into the mode of action of acanthoic acid and on the activation of TNF-α. The C19 carboxylic acid or the C15 aldehyde (precursor of 1) are useful in cross-linking experiments with the appropriate photosensitive reagents (see 60 and 61, FIG. 12).

Synthesis of Dimers and Conjugates of the Compounds of Formula (II), (IIA) and (IIB)

Dimeric forms the compounds of Formula (II), (IIA) and (IIB), such as for example 62 (n=1), have been isolated from natural sources and, furthermore, the dexamethasone-acanthoic acid conjugate 63 provides biologically interesting results toward a drug targeting a steroid receptor with potential implications in cancer research. See Chamy, M. C.; Piovano, M.; Garbarino, J. A.; Miranda, C.; Vicente, G. *Phytochemistry* 1990, 9, 2943–2946. While no biological studies of this class of compounds has been performed, according to the invention, dimeric analogs of Formula (II), (IIA) and (IIB) are evaluated. Synthetic acanthoic acid or bioactive analogs of 1 are used as monomeric partners and their coupling is performed using standard techniques, included those described herein.

Experimental Techniques

All reactions were carried out under an argon atmosphere in dry, freshly distilled solvents under anhydrous conditions, unless otherwise noted. Tetrahydrofuran (THF) and diethyl ether (Et$_2$O) were distilled from sodium/benzophenone; dichloromethane (CH$_2$Cl$_2$), hexamethyl phosphoramide (HMPA), and toluene from calcium hydride; and dimethyl formamide (DMF) from calcium chloride. Yields refer to chromatographically and spectroscopically ($^1$H NMR) homogeneous materials, unless otherwise stated. Reagents were purchased at highest commercial quality and used without further purification, unless otherwise stated. Reactions were monitored by thin-layer chromatography carried out on 0.25 mm E. Merck silica gel plates (60F-254) using UV light as visualizing agent and 7% ethanolic phosphomolybdic acid, or p-anisaldehyde solution and heat as developing agents. E. Merck silica gel (60, particle size 0.040–0.063 mm) was used for flash chromatography. Preparative thin-layer chromatography separations were carried out on 0.25 or 0.50 mm E. Merck silica plates (60F-254). NMR spectra were recorded on a Varian 400 and/or 500 Mhz instruments and calibrated using a residual undeuterated solvent as an internal reference. The following abbreviations were used to explain the multiplicities: s=singlet; d=doublet, t=triplet; q=quartet, m=multiplet, b=broad. IR spectra were recorded on a Nicolet Avatar 320 FT-IR spectrometer. Optical rotations were recorded on a Perkin Elmer 241 polarimeter. High resolution mass spectra (HRMS) were recorded on a VG 7070 HS mass spectrometer under chemical ionization (CI) conditions or on a VG ZAB-ZSE mass spectrometer under fast atom bombardment (FAB) conditions.

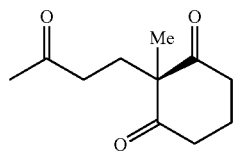

2

Triketone 2. A solution of diketone 1 (50 g, 0.40 mol) in ethyl acetate (500 ml) was treated with triethylamine (72 ml, 0.52 mol) and methyl vinyl ketone (36 ml, 0.44 mol). The reaction mixture was refluxed at 70° C. for 10 h and then cooled to 25° C. The solvent was removed under pressure and the resulting crude material was chromatographed directly (10–40% ether in hexanes) to yield triketone 2 (61 g, 0.31 mol, 78%). 2: colorless oil; R$_f$=0.25 (silica, 50% ether in hexanes); $^1$H NMR (400 MHz, CDCl$_3$) δ 2.75–2.59 (m, 4H), 2.34 (t, 2H, J=7.2 Hz), 2.10 (s, 3H), 2.07–2.05 (m, 3H), 1.98–1.94 (m, 1H), 1.24 (s, 3H).

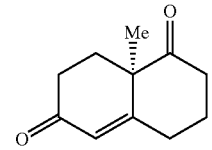

3

Wieland-Miescher ketone (3) A solution of triketone 2 (61 g, 0.31 mol) in dimethyl sulfoxide (400 ml) was treated with finely grounded D-proline (1.7 g, 0.01 mol). (As noted below, see Examples 18 through 21, triketone 2 in dimethyl sulfoxide (400 ml) may also be treated with finely grounded L-proline to yield the enantiomer of the Wieland-Miescher ketone (3)). The solution was stirred at 25° C. for 4 days and then stirred at 40° C. for 1 more day. The resulting purple colored solution was cooled to 25 C, diluted with water (300 ml) and brine (100 ml), and poured into a separatory funnel. The mixture was extracted with ethyl ether (3×800 ml). The organic layers were concentrated (without drying) and subjected to chromatography (10–40% ether in hexanes) to give 59 g of a crude reddish-violet oil. The material was again subjected to chromatography (10–40% ether in hexanes) and concentrated to yield 57 g of a yellow oil. The oil was dissolved in ethyl ether (400 ml) and kept at 4° C. for 30 min, after which time a layer of hexanes (100 ml) was added on top of the ether. The two-layered solution was seeded with a few crystals and placed into a freezer (−28° C.) overnight. The resulting crystals were collected by filtration, rinsed with ice-cold hexanes (2×100 ml), and dried under pressure. Concentration of the mother liquor afforded another crop, and combining the crystals afforded the Wieland-Miescher ketone (3) (43 g, 0.24 mol, 78%). 3: tan crystals; R$_f$=0.25 (silica, 50% ether in hexanes); [α]$^{25}_D$: −80.0 (c=1, C$_6$H$_6$); $^1$H NMR (400 MHz, CDCl$_3$) δ 5.85 (s, 1H), 2.72–2.66 (m, 2H), 2.51–2.42 (m, 4H), 2.14–2.10 (m, 3H), 1.71–1.68 (m, 1H), 1.44 (s, 3H); $^{13}$C NMR (100 MHz, CDCl$_3$) δ 210.7, 198.0, 165.6, 125.7, 50.6, 37.7, 33.7, 31.8, 29.7, 23.4, 23.0.

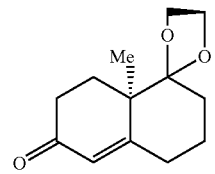

4

Acetal 4. A solution of ketone 3 (43 g, 0.24 mol) in benzene (700 ml) was treated with p-toluenesulfonic acid (4.6 g, 0.024 mol) and ethylene glycol (15 ml, 0.27 mol). The reaction was refluxed with a Dean-Stark apparatus and condenser at 120 C. Once water stopped collecting in the Dean-Stark apparatus, the reaction was complete (approx. 4 h). Leaving the reaction for longer periods of time tended to darken the reaction mixture and lower the overall yield. The reaction was cooled to 25° C., quenched with triethylamine (5 ml, 0.036 mol), and poured into a separatory funnel containing water (300 ml) and saturated sodium bicarbonate (200 ml). The resulting mixture was then extracted with ether (3×800 ml). The organic layers were combined, dried over MgSO$_4$, concentrated, and subjected to chromatography (10–40% ether in hexanes) to afford acetal 4 (48 g, 0.22 mol, 90%). 4: yellow oil; R$_f$=0.30 (silica, 50% ether in hexanes); [α]$^{25}_D$: −77 (c=1, C$_6$H$_6$); IR (film) υ$_{max}$ 2943, 2790, 1667, 1450, 1325, 1250; $^1$H NMR (400 MHz, CDCl$_3$) d 5.80 (s, 1H), 3.98–3.93 (m, 4H), 2.43–2.35 (m, 3H), 2.34–2.20 (m, 3H), 1.94–1.82 (m, 1H), 1.78–1.60 (m, 3H), 1.34 (s, 3H); $^{13}$C NMR (100 MHz, CDCl$_3$) δ 198.9, 167.5, 125.5, 112.2, 65.4, 65.1, 45.1, 34.0, 31.5, 30.1, 26.9, 21.8, 20.6.

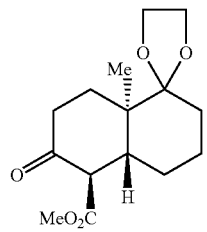

5

Ketoester 5. A solution of lithium (0.72 g, 0.10 mol) in liquid ammonia (400 ml) at −78 C was treated dropwise with a solution of acetal 4 (10 g, 0.045 mol) and tert-butyl alcohol (3.7 ml, 0.045 mol) in ether (40 ml). The resulting blue mixture was allowed to warm and stir at reflux (−33° C.) for 15 min and then cooled to −78° C. again. Sufficient isoprene (approx. 8 ml) was added dropwise to discharge the residual blue color of the reaction mixture. The reaction was then warmed in a water bath (50° C.) and the ammonia quickly evaporated under a stream of dry nitrogen. The remaining ether was removed under pressure to leave a white foam. After a further 5 min under high vacuum, the nitrogen atmosphere was restored, and the lithium enolate was suspended in dry ether (150 ml) and cooled to −78° C. Methyl cyanoformate (4.0 ml, 0.050 mol) was then added and the reaction stirred for 40 min at −78 C. The reaction was warmed to 0° C. and stirred for 1 h more. Water (300 ml) and ether (200 ml) were added and the mixture poured into a separatory funnel containing saturated sodium chloride (100 ml). After separating the organic layer, the aqueous phase was extracted with ether (2×400 ml). The combined organic layers were dried over MgSO$_4$, concentrated, and subjected to chromatography (10–40% ether in hexanes) to afford ketoester 5 (7.0 g, 0.025 mol, 55%). 5: white powdery precipitate; R$_f$=0.40 (silica, 50% ether in hexanes); [α]$^{25}$$_D$: −2.9 (c=1, C$_6$H$_6$); IR (film) ν$_{max}$ 2943, 1746, 1700; $^1$H NMR (400 MHz, CDCl$_3$) δ 4.00–3.96 (m, 2H), 3.95–3.86 (m, 2H), 3.74 (s, 3H), 3.23 (d, 1H, J=13.2 Hz), 2.50–2.42 (m, 3H), 2.05–1.92 (m, 1H), 1.79–1.50 (m, 5H), 1.32–1.28 (m, 2H), 1.21 (s, 3H); $^{13}$C NMR (100 MHz, CDCl$_3$) δ 205.4, 170.0, 111.9, 65.2, 65.1, 59.9, 52.0, 43.7, 41.6, 37.5, 30.3, 29.8, 26.2, 22.5, 14.0; HRMS, calcd for C$_{15}$H$_{22}$O$_5$ (M+Na$^+$) 305.1359, found 305.1354.

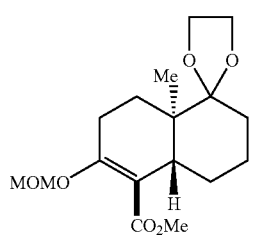

6

Ester 6. A solution of ketoester 5 (7.0 g, 0.025 mol) in HMPA (50 ml) was treated with sodium hydride (0.71 g, 0.030 mol). After stirring for 3 h at 25° C., the resulting yellow-brown reaction mixture was quenched with chloromethyl methyl ether (2.3 ml, 0.030 mol) and the reaction allowed to stir an additional 2 h at 25° C. The resulting white-yellow mixture was then poured into a separatory funnel containing ice-water (100 ml), saturated sodium bicarbonate (50 ml), and ether (200 ml). After the layers were separated, the aqueous layer was extracted with ether (3×200 ml). The combined ethereal extracts were dried over MgSO$_4$, concentrated, and subjected to chromatography (silica, 10–40% ether in hexanes) to yield ester 6 (7.7 g, 0.024 mol, 95%). 6: yellow oil; R$_f$=0.45 (silica, 50% ether in hexanes); [α]$^{25}$$_D$: +26.3 (c=1, C6H6); IR (film) ν$_{max}$ 2951, 1728, 1690, 1430, 1170; $^1$H NMR (400 MHz, CDCl$_3$) δ 4.89 (dd, 2H, J=22.8, 6.4 Hz), 3.93–3.91 (m, 2H), 3.90–3.84 (m, 2H), 3.69 (s, 3H), 3.40 (s, 3H), 2.72–2.68 (m, 1H), 2.24 (bs, 2H), 1.80–1.42 (m, 4H), 1.37–1.15 (m, 2H), 0.960 (s, 3H), 0.95–0.80 (m, 2H); $^{13}$C NMR (100 MHz, CDCl$_3$) δ 167.8, 150.5, 115.8, 112.1, 93.0, 65.2, 65.1, 56.3, 51.3, 40.7, 40.3, 30.3, 26.4, 23.6, 22.9, 22.3, 13.9; HRMS, calcd for C$_{17}$H$_{26}$O$_6$ (M+Na$^+$) 349.1622, found 349.1621.

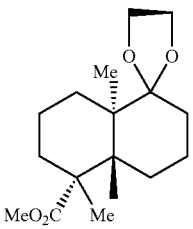

7

Acetal 7. A solution of lithium (1.1 g, 0.17 mol) in liquid ammonia (400 ml) at −78 C was treated dropwise with a solution of ester 6 (7.7 g, 0.024 mol) in 1,2-DME (30 ml). The blue reaction mixture was allowed to warm and stir at reflux (−33° C.) for 20 min. The reaction mixture was then cooled to −78° C. again and rapidly quenched with excess iodomethane (15 ml, 0.24 mol). The resulting white slurry was allowed to stir at reflux (−33° C.) for 1 h, after which time the reaction was warmed in a water bath (50° C.) with stirring for 1 h, allowing the ammonia to evaporate. The reaction mixture was quenched with water (100 ml), sodium bicarbonate (100 ml), and ether (200 ml) and poured into a separatory funnel. After the layers were separated, the aqueous layer was extracted with ether (3×200 ml). The combined ethereal extracts were dried over MgSO$_4$, concentrated, and subjected to chromatography (silica, 10–30% ether in hexanes) to yield acetal 7 (4.1 g, 0.014 mol, 61%). 7: semi-crystalline yellow oil; R$_f$=0.80 (silica, 50% ether in hexanes); [α]$^{25}$$_D$: +16.9 (c=10, C$_6$H$_6$); IR (film) ν$_{max}$ 2934, 1728, 1466, 1379, 1283, 1125, 942; $^1$H NMR (400 MHz, CDCl$_3$) δ 3.95–3.80 (m, 4H), 3.64 (s, 3H), 2.17–2.15 (m, 1H), 1.84–1.37 (m, 1H), 1.16 (s, 3H), 1.05–1.00 (m, 1H), 0.87 (s, 3H); $^{13}$C NMR (100 MHz, CDCl$_3$) δ 177.7, 112.9, 65.2, 64.9, 51.2, 44.0, 43.7, 38.1, 30.7, 30.3, 28.8, 23.4, 19.1, 14.7; HRMS, calcd for C$_{16}$H$_{26}$O$_4$ (M+H$^+$) 283.1904, found 283.1904.

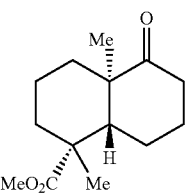

8

Ketone 8. A solution of acetal 7 (4.1 g, 0.014 mol) in THF (50 ml) was treated with 1M HCl dropwise (approx. 15 ml) at 25° C. with stirring. The reaction was monitored by thin layer chromatography and neutralized with sodium bicarbonate (30 ml) once the starting material disappeared. The resulting mixture was poured into a separatory funnel containing water (100 ml) and ether (100 ml). After the layers were separated, the aqueous layer was extracted with ether (3×100 ml). The combined ethereal extracts were dried over MgSO$_4$, concentrated, and subjected to chromatography (silica, 10–20% ether in hexanes) to yield ketone 8 (3.3 g, 0.014 mol, 95%). 8: white crystals; R$_f$=0.70 (silica, 50% ether in hexanes); [α]$^{25}_D$: +3.5 (c=1.0, C$_6$H$_6$); IR (film) ν$_{max}$ 2943, 1728, 1449, 1239, 1143, 1095, 985; $^1$H NMR (400 MHz, CDCl$_3$) δ 3.62 (s, 3H), 2.55–2.45 (m, 1H), 2.92–1.95 (m, 5H), 1.8–1.6 (m, 2H), 1.50–1.30 (m, 4H), 1.14 (s, 3H), 0.98–0.96 (m, 1H), 0.90 (s, 3H); $^{13}$C NMR (100 MHz, CDCl$_3$) δ 214.8, 177.0, 54.4, 51.3, 49.3, 44.2, 37.9, 37.7, 33.1, 28.6, 26.4, 22.8, 18.8, 17.0; HRMS, calcd for C$_{14}$H$_{22}$O$_3$ (M+Na$^+$) 261.1461, found 261.1482.

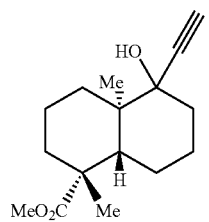

9

Alkyne 9. A solution of ketone 8 (2.0 g, 8.3 mmol) in ether (50 ml) was treated with lithium acetylide (0.40 g, 13 mmol). The reaction was stirred at 25 C for 1 h and then quenched with sodium bicarbonate (20 ml) and water (30 ml). The mixture was poured into a separatory funnel and the layers were separated. The aqueous layer was extracted with ether (3×50 ml). The organic layers were combined, dried with MgSO$_4$, concentrated, and subjected to chromatography (silica, 10–30% ether in hexanes) to afford alkyne 9 (2.0 g, 7.6 mmol, 90%). 9: white solid; R$_f$=0.65 (silica, 50% ether in hexanes); $^1$H NMR (400 MHz, CDCl$_3$) δ 3.64 (s, 3H), 2.56 (s, 1H), 2.18–2.10 (m, 1H), 1.92–1.40 (m, 12H), 1.18 (s, 3H), 1.17–1.01 (m, 1H), 0.81 (s, 3H); $^{13}$C NMR (100 MHz, CDCl$_3$) 177.6, 86.8, 76.5, 75.0, 51.2, 50.5, 43.9, 52.5, 37.9, 35.3, 33.4, 28.8, 23.5, 22.5, 19.1, 11.5; HRMS, calcd for C$_{16}$H$_{24}$O$_3$ (M+H$^+$−H$_2$O) 247.1693, found 247.1697.

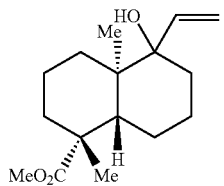

10

Alkene 10. A solution of alkyne 9 (0.50 g, 1.9 mmol) in 1, 4 dioxane (20 ml) and pyridine (2 ml) was treated with Lindlar's catalyst (100 mg). The mixture was hydrogenated under pressure (30 lbs/in$^2$) for 7 min. The reaction mixture was then diluted with ether (10 ml), filtered through a pad of celite, and washed with ether (2×50 ml). The solvent was evaporated under reduced pressure to afford alkene 10 (0.48 g, 1.8 mmol, 95%). 10: colorless oil; $^1$H NMR (400 MHz, CDCl$_3$) δ 6.58 (dd, 1H), 5.39 (d, 1H), 5.14 (d, 1H), 3.64 (s, 3H), 2.20–2.11 (m, 2H), 1.93–1.65 (m, 4H), 1.61 (s, 2H), 1.52–1.25(m, 4H), 1.19(s, 3H), 1.17–0.90(m, 2H), 0.89 (s, 3H).

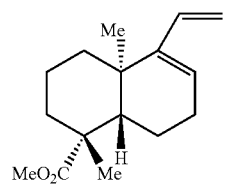

11

Diene 11. A solution of alkene 10 (0.48 g, 1.8 mmol) in benzene (80 ml) and THF (20 ml) was treated with boron trifluoride etherate (1 ml, 7.9 mmol), and the reaction mixture was refluxed at 100 C for 5 h. After cooling, the reaction was quenched with 1N NaOH (1 ml, 26 mmol) and the mixture was poured into a separatory funnel containing water (100 ml) and ether (100 ml). After separating the layers, the aqueous layer was extracted with ether (3×100 ml). The organic layers were combined, dried with MgSO$_4$, concentrated, and subjected to chromatography (silica, 5% ether in hexanes) to afford diene 11 (0.42 g, 1.7 mmol, 95%). 11: colorless oil; R$_f$=0.95 (silica, 50% ether in hexanes); $^1$H NMR (400 MHz, CDCl$_3$) δ 6.26–6.23 (dd, 1H), 5.70 (s, 1H), 5.253 (d, 1H, J=19.2 Hz), 4.91 (d, 1H, J=12.8 Hz), 3.64 (s, 3H), 2.22–2.12 (m, 2H), 2.10–1.94 (m, 2H) 1.92–1.67 (m, 3H), 1.60–1.44 (m, 3H), 1.378 (d, 1H, J=13.6), 1.21 (s, 1H), 1.19–1.00 (m, 2H), 0.86 (s, 3H); $^{13}$C NMR (100 MHz, CDCl$_3$) δ 177.7, 146.7, 136.1, 121.9, 113.3, 53.0, 51.2, 43.9, 38.0, 37.9, 37.4, 28.5, 27.8, 20.5, 19.5, 18.3.

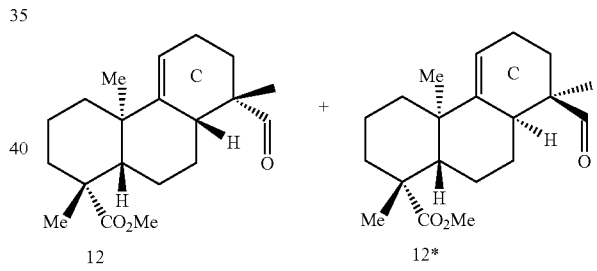

12                       12*

Aldehyde 12. A solution of methacrolein (0.5 ml, 5.2 mmol) and diene 11 (0.1 g, 0.40 mmol) was stirred for 8 h at 25° C. under neat conditions. The excess methacrolein was then removed under reduced pressure. The crude product was subjected to chromatography (silica, 10–20% ether in hexanes) to afford aldehydes 12 and 12* (0.13 g, 0.40 mmol, 100%) as a mixture of diastereomers (3:1–4:1 ratio at C13). 12 and 12*: colorless oil; R$_f$=0.55 (silica, 25% ether in hexanes); 12: IR (film) ν$_{max}$ 3441, 2936, 1726, 1451, 1233, 1152; $^1$H NMR (400 MHz, CDCl$_3$) δ9.70 (s, 1H), 5.58 (m, 1H), 3.62 (s, 3H), 2.38–2.25 (m, 1H), 2.21–2.18 (m, 1H), 2.17–1.98 (m, 4H), 1.96–1.62 (m, 6H), 1.61–1.58 (m, 1H), 1.57–1.43 (m, 2H), 1.40–1.23 (m, 1H), 1.17 (s, 3H), 1.04 (s, 3H), 0.92 (s, 3H); $^{13}$C (100 MHz, CDCl$_3$) δ 207.6, 177.7, 148.3, 188.6, 51.3, 47.8, 47.0, 44.2, 41.2, 39.3, 38.8, 38.1, 29.5, 28.4, 22.9, 22.5, 21.8, 20.6, 20.5, 19.7; 12*: [α]$^D_{25}$: +36.8 (c=0.7, C$_6$H$_6$); IR (film) ν$_{max}$ 3441, 2936, 1726, 1451, 1233, 1152; $^1$H NMR (400 MHz, CDCl$_3$) δ9.64 (s, 1H), 5.42 (m, 1H), 3.66 (s, 3H), 2.29–2.10 (m, 4H), 2.09–1.84 (m, 4H), 1.81–1.77 (m, 2H), 1.75–1.63 (m, 2H), 1.62–1.58 (m, 2H), 1.57–1.45 (m, 1H), 1.43 (s, 1H), 1.13 (s, 3H), 1.03 (s, 3H), 0.87 (s, 3H); $^{13}$C NMR (100 MHz, CDCl$_3$)

δ 207.3, 177.5, 147.4, 114.6, 55.8, 51.3, 47.3, 44.5, 40.7, 40.4, 38.4, 37.5, 31.5, 28.6, 25.0, 24.2, 21.9, 19.9, 19.6, 18.7.

The preferred way to purify the diastereomeric aldehydes is to reduce them with sodium borohydride in MeOH and separate the alcohols. The major compound (top diastereomer) can then be oxidized to the desired aldehyde 12 upon treatment with Dess-Martin periodinane.

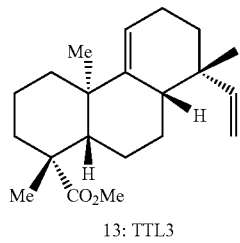

13: TTL3

Alkene 13 (TTL3). A solution of (methyl)-triphenylphosphonium bromide (357 mg, 1.0 mmol) in THF (40 ml) was treated with 1M NaHMDS in THF (0.86 ml, 0.86 mmol). The resulting yellow mixture was allowed to stir at 25° C. for 30 min. After this time, a solution of aldehyde 12 (91 mg, 0.29 mmol) in THF (10 ml) was added to the reaction via cannula. The reaction mixture was stirred at 25° C. for 8 hours and then quenched with sodium bicarbonate (30 ml) and water (20 ml). The mixture was poured into a separatory funnel containing ether (50 ml). After separating the layers, the aqueous layer was extracted with ether (3×50 ml). The organic layers were combined, dried with MgSO$_4$, condensed, and subjected to chromatography (silica, 10% ether in hexanes) to afford alkene 13 (84 mg, 0.28 mmol, 97%). 13: colorless oil; R$_f$=0.75 (silica, 25% ether in hexanes); 13: $^1$H NMR (400 MHz, CDCl$_3$) δ 5.96dd, 1H, J=16.8, 11.6 Hz), 5.50 (m, 1H), 4.98 (m, 2H), 3.62 (s, 3H), 2.20–2.11 (m, 1H), 2.10–1.91 (m, 4H), 1.90–1.70 (m, 4H), 1.69–1.51 (m, 3H), 1.50–1.38 (m, 3H), 1.36–1.24 (m, 1H), 1.17 (s, 3H), 1.04 (s, 3H), 0.90 (s, 3H); $^{13}$C NMR (100 MHz, CDCl$_3$) δ177.9, 149.1, 143.8, 117.9, 111.7, 51.2, 47.7, 44.4, 41.4, 41.2, 38.9, 38.3, 37.7, 34.8, 30.4, 28.4, 24.8, 23.1, 22.3, 22.2, 20.6, 19.8.

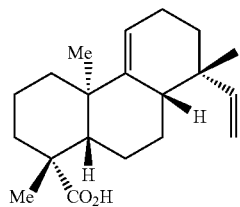

14: TTL1

Acid 14 (TTL1). A solution of alkene 13 (84 mg, 0.28 mmol) in dimethyl sulfoxide (20 ml) was treated with LiBr (121 mg, 1.4 mmol). The reaction mixture was refluxed at 180 C for 2 days. After cooling down, the reaction was diluted with water (30 ml) and extracted with ether (3×50 ml). The organic layers were combined, dried with MgSO$_4$, concentrated, and subjected to chromatography (silica, 30% ether in hexanes) to afford carboxylic acid 14 (TTL1) (78 mg, 0.26 mmol). 14: white solid; R$_f$=0.30 (silica, 30% ether in hexanes); $^1$H NMR (400 MHz, CDCl$_3$) δ 5.96 (dd, 1H, J=14.4, 9.6 Hz), 5.52 (m, 1H), 4.98–4.95 (m, 2H), 2.20–1.72 (m, 10H), 1.64–1.58 (m, 3H), 1.57–1.37 (m, 4H), 1.22 (s, 3H), 1.04 (s, 3H), 0.99 (s, 3H); $^{13}$C NMR (100 MHz, CDCl$_3$) δ 182.9, 149.3, 143.9, 118.1, 111.9, 47.5, 44.2, 41.3, 41.2, 38.9, 38.0, 37.6, 34.8, 28.4, 24.7, 23.0, 22.4, 21.9, 20.3, 19.5.

Preparation of Ph$_3$P=$^{14}$CH$_2$.

Triphenylphosphine (0.16 g, 0.61 mmol) was added in a 15 ml reaction flask and dried overnight under vacuum at 25° C. To this flask was added 2 ml of THF (dried and degassed under vacuum), followed by $^{14}$CH$_3$I (50 mCi, 53 mCi/mmol, 0.9 mmol) dissolved in 1 ml of THF and the mixture was stirred for 24 hours under argon. Potassium hexamethyldisilylamide (2.5 ml, 1.25 mmol, 0.5 M in toluene) was then added and the reddish-yellow mixture was allowed to stir for 3 h at 25° C.

Wittig Reaction with Ph$_3$P=$^{14}$CH$_2$.

The above mixture was cooled at −78° C. and treated with aldehyde 12 (63 mg, 0.2 mmol) in dry THF (1.5 ml). The mixture was allowed to warm slowly to 25° C., stirred for 8 h and quenched with sodium bicarbonate (10 ml) and water (10 ml). The mixture was extracted with ether (3×50 ml) and the organic layers were combined, dried with MgSO$_4$, condensed, and subjected to chromatography over silica gel (silica, 10% ether in hexanes) to afford alkene 13.

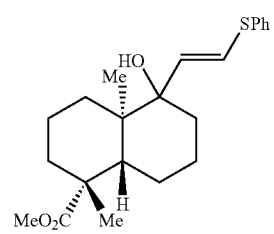

Alcohol 15. A solution of alkyne 9 (1.10 g, 4.2 mmol), thiophenol (1.37 g, 12.4 mmol) and 2,2'-azobisisobutyronitrile (AIBN, 34.5 mg, 0.21 mmol) in xylene (25 ml) was stirred at 110° C. (under argon) for 18 h. The reaction mixture was cooled to 25° C. and quenched with aqueous saturated sodium bicarbonate (50 ml). The organic layer was extracted with ethyl ether (3×50 ml), collected, dried (MgSO$_4$), concentrated and residue was chromatographed (silica, 2–5% ethyl ether in hexane) to afford alchohol 15 (1.35 g, 3.6 mmol, 85.7%); 15: colorless liquid; R$_f$=0.51 (silica, 5% ethyl ether in hexanes); [α]$^{25}_D$: +24.20 (c=1.0, benzene); IR (film) ν$_{max}$ 2946.8, 1724.5, 1472.6, 1438.4, 1153.5, 740.0, 690.9; $^1$H NMR (500 MHz, CDCl$_3$) δ 7.20–7.60 (m, 5H), 5.23 (d, 1H, J=10.5 Hz), 5.12 (d, 1H, J=10.0 Hz), 3.62 (s, 3H), 2.08–2.24 (m, 2H), 1.16–1.92 (m, 9H), 1.09 (s, 3H), 0.86–1.02 (m, 2H), 0.68 (s, 3H); $^{13}$C NMR (100 MHz, CDCl$_3$) δ 177.8, 151.7, 133.9, 133.7, 128.8, 127.9, 118.2, 54.9, 53.5, 51.1, 44.3, 40.4, 38.1, 37.3, 28.7, 27.7, 25.5, 23.5, 19.5, 18.5.

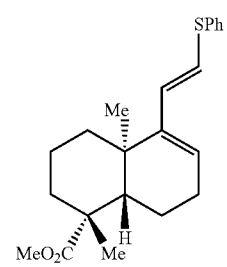

Diene 16. To a solution of alchohol 15 (1.10 g, 2.94 mmol) in hexamethyl phosphoramide (HMPA, 10 ml) was added dropwise phosphorus oxychloride (0.50 g, 3.3 mmol) and the mixture was stirred at 25° C. until clear. Pyridine (0.26 ml, 3.23 mmol) was then added and the mixture was stirred at 150° C. (under argon) for 18 hrs. The reaction mixture was cooled to 25° C. and quenched with aqueous saturated sodium bicarbonate (50 ml). The organic layer was extracted with ethyl ether (3×60 ml), collected, dried (MgSO$_4$) and concentrated and residue was chromatographed (silica, 2–5% ethyl ether in hexane) to afford diene 16 (0.85 g, 2.38 mmol, 81%); 16: colorless liquid; R$_f$=0.60 (silica, 5% ethyl ether in hexanes); [α]$^{25}_D$: −17.30 (c=1.08, benzene); IR (film) ν$_{max}$ 2957.0, 1726.6, 1581.6, 1478.3, 1439.0, 1234.7, 1190.8, 1094.8, 1024.4, 739.1; $^1$H NMR (500 MHz, CDCl$_3$) δ 7.20–7.60 (m, 5H), 6.43 (d, 1H, J=15.0 Hz), 6.36 (d, 1H, J=14.5 Hz), 5.72 (m, 1H), 3.64 (s, 3H), 1.48–2.32 (m, 10H), 1.43 (s, 3H), 1.21 (s, 3H), 1.05 (m, 1H), 0.88 (s, 3H); $^{13}$C NMR (125 MHz, CDCl$_3$) δ177.9, 133.7, 129.1, 128.9, 128.6, 127.5, 126.2, 123.4, 120.9, 52.8, 51.1, 43.7, 37.7, 37.3, 30.2, 28.3, 27.7, 20.1, 19.3, 18.3.

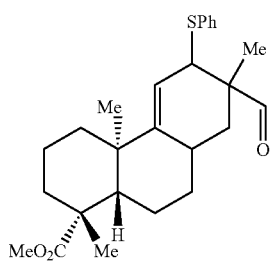

17

Aldehyde 17. To a solution of diene 16 (0.51 g, 1.43 mmol) and methacrolein (0.30 g, 4.30 mmol) in dichloromethane (5 ml) at −20° C. was added under argon dropwise tin (IV) chloride (0.29 ml of 1M solution in dichloromethane, 0.29 mmol). The resulting mixture was warmed to 0° C. within 1 hr and stirred at 0° C. for 18 h. The reaction was quenched with aqueous saturated sodium bicarbonate (15 ml) and the organic layer was extracted with ethyl ether (3×20 ml). The combined organic layers were dried (MgSO$_4$) and concentrated and residue was chromatographed (silica, 10–15% ethyl ether in hexane) to afford aldehyde 17 (0.51 g, 1.19 mmol, 83.7%); 4: colorless liquid; R$_f$=0.48 (silica, 10% ethyl ether in hexanes); [α]$^{25}$ D: +30.0 (c=1.13, benzene); IR (film) ν$_{max}$ 2930.8, 2871.4, 1724.9, 1458.4, 1226.4, 1149.8; $^1$H NMR (500 MHz, CDCl$_3$) δ 9.51 (s, 1H), 7.20–7.60 (m, 5H), 5.57 (m, 1H), 3.65 (s, 3H), 1.20–2.32 (m, 15H), 1.17 (s, 3H), 1.05 (s, 3H), 0.91 (s, 3H); $^{13}$C NMR (125 MHz, CDCl$_3$) δ203.6, 177.9, 153.7, 133.6, 133.5, 128.9, 127.8, 117.1, 51.3, 49.1, 47.7, 44.2, 41.6, 38.7, 38.1, 31.2, 28.3, 27.8, 26.9, 21.7, 20.2, 19.3, 18.6.

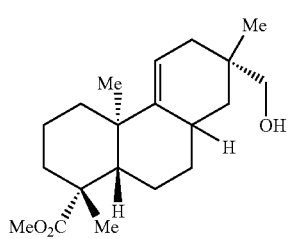

18

Alcohol 18. To a solution of aldehyde 17 (0.50 g, 1.17 mmol) in anhydrous ethanol (5 ml) was added portionwise sodium borohydride (50 mg, 1.32 mmol) and the mixture was stirred for 30 min. Aqueous saturated sodium bicarbonate (10 ml) was then added and the mixture was extracted with ethyl ether (3×20 ml). The organic layer was collected, dried (MgSO$_4$) and concentrated. The residue was redissolved in tetrahydrofuran (5 ml) and treated with excess of Raney Nickel under argon at 65° C. for 10 min. The reaction mixture was filtered, and the filtrate was dried (MgSO$_4$) and concentrated, and the residue was chromatographed (silica, 2–5% ethyl ether in hexane) to afford alcohol 18 as a major compound (0.21 g, 0.65 mmol, overall yield 56.1%. Note: the overall yield for the above two reactions is 91%); 18: colorless liquid; R$_f$=0.39 (silica, 30% ethyl ether in hexanes); [α]$^{25}_D$: −6.70 (c=1.0, benzene); IR (film) ν$_{max}$ 3436.8, 2929.0, 2872.2, 1728.1, 1433.9, 1260.6, 1029.7, 801.6; $^1$H NMR (500 MHz, CDCl$_3$) δ 5.37 (m, 1H), 3.62 (s, 3H), 2.28 (bs, 1H), 2.06–2.20 (m, 2H), 1.20–2.00 (m, 12H), 1.16 (s, 3H), 0.99 (m, 1H), 0.86 (s, 3H), 0.84 (s, 3H); $^{13}$C NMR (125 MHz, CDCl$_3$) δ178.2, 150.4, 116.4, 73.6, 51.2, 47.9, 44.2, 41.9, 38.8, 38.2, 34.3, 33.9, 28.3, 28.2, 27.8, 22.1, 20.3, 20.1, 18.9.

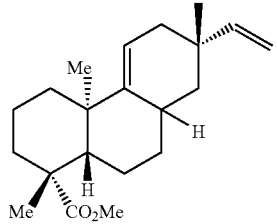

19

Alkene 19. To a solution of alchohol 18 (20.0 mg, 0.062 mmol) in dichloromethane (2 ml) was added Dess-Martin periodinane (35 mg, 0.08 mmol) in portions, and the mixture was stirred at 25° C. for 30 min. The reaction was quenched with aqueous saturated sodium bicarbonate (5 ml) and extracted with ethyl ether (3×10 ml). The organic layer was collected, dried (MgSO$_4$) and concentrated. The residue was redissolved in tetrahydrofuran (0.5 ml) and added under argon to a yellow suspension of (methyl) triphenyl-phosphonium bromide (60 mg, 0.17 mmol) and sodium bis (trimethylsilyl) amide (0.14 ml of 1.0 M in THF) in THF (1.5 ml). After stirring at 25° C. for 18 h the mixture was diluted with aqueous saturated sodium bicarbonate (5 ml) and extracted with ethyl ether (3×10 ml). The organic layer was collected, dried (MgSO$_4$), concentrated and residue was chromatographed (silica, 2–5% ethyl ether in hexane) to afford alkene 19 (16.8 mg, 0.05 mmol, the overall yield for the two-step reactions is 86%); 19: colorless liquid; R$_f$=0.74 (silica, 5% ethyl ether in hexanes); [α]$^{25}_D$: −14.40 (c=0.50, benzene); IR (film) ν$_{max}$ 2929.5, 2873.4, 1726.8, 1637.7, 1460.7, 1376.8, 1225.1, 1150.4, 997.8, 908.7; $^1$H NMR (500 MHz, CDCl$_3$) δ 5.82 (dd, 1H), 5.39 (m, 1H), 4.85–4.94 (dd, 2H), 3.64 (s, 3H), 2.30 (bs, 1H), 2.14 (m, 1H), 2.02 (m, 1H), 1.80–1.98 (m, 2H), 1.68–1.80 (m, 2H), 1.20–1.68 (m, 7H), 1.18 (s, 3H), 0.96–1.08 (m, 2H), 0.95 (s, 3H), 0.88 (s, 3H); $^{13}$C NMR (125 MHz, CDCl$_3$) δ178.3, 150.4, 125.6, 116.6, 109.2, 51.2, 47.9, 44.3, 41.9, 41.8, 38.3, 38.2, 37.4, 34.8, 30.2, 29.6, 28.6, 28.4, 27.8, 22.1, 20.4, 19.0.

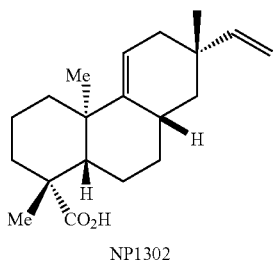

NP1302

Compound of Formula (I). To a solution of alkene 19 (16.8 mg, 0.05 mmol) in N,N-dimethylformamide (2 ml) added lithium bromide (5.0 mg, 0.06 mmol) and the mixture was refluxed at 190° C. for 1 hr. The reaction mixture was then cooled to 25° C., diluted with $H_2O$ (5 ml) and extracted with ethyl acetate (3×10 ml). The organic layer was collected, dried ($MgSO_4$) and concentrated and residue was chromatographed (silica, 15–20% ethyl ether in hexane) to afford Formula (I) (14.9 mg, 0.05 mmol, 92.6%);

Compound of Formula (I) is a colorless liquid; $R_f$=0.20 (silica, 30% ethyl ether in hexanes); $[\alpha]^{25}_D$: −6.0 (c=0.33, benzene); IR (film) $v_{max}$ 3080.6, 2928.9, 2857.6, 1693.6, 1638.2, 1464.7, 1413.8, 1376.4, 1263.1, 1179.3, 1095.9, 1027.5, 999.2, 909.2, 801.7; $^1H$ NMR (500 MHz, $CDCl_3$) δ 5.82 (dd, 1H), 5.40 (m, 1H), 4.85–4.95 (dd, 2H), 2.30 (bs, 1H), 2.16 (m, 1H), 2.02 (m, 1H), 1.80–1.98 (m, 2H), 1.70–1.84 (m, 2H), 1.10–1.70 (m, 7H), 1.24 (s, 3H), 1.00–1.10 (m, 2H), 0.99 (s, 3H), 0.95 (s, 3H); $^{13}C$ NMR (125 MHz, $CDCl_3$) δ 150.3, 149.9, 116.7, 109.2, 47.9, 41.8, 41.7, 38.3, 38.2, 37.4, 34.8, 31.8, 28.6, 28.5, 27.7, 22.6, 22.4, 22.1, 20.3, 18.9.

Methods of Using the Invention

The in vitro and in vivo methods described above as part of the present invention also establish the selectivity of a TNF-α or IL-1 modulator. It is recognized that chemicals can modulate a wide variety of biological processes or be selective. Panels of cells based on the present invention can be used to determine the specificity of the candidate modulator. Selectivity is evident, for example, in the field of chemotherapy, where the selectivity of a chemical to be toxic towards cancerous cells, but not towards non-cancerous cells, is obviously desirable. Selective modulators are preferable because they have fewer side effects in the clinical setting. The selectivity of a candidate modulator can be established in vitro by testing the toxicity and effect of a candidate modulator on a plurality of cell lines that exhibit a variety of cellular pathways and sensitivities. The data obtained from these in vitro toxicity studies may be extended to animal models, including accepted animal model studies and human clinical trials, to determine toxicity, efficacy, and selectivity of the candidate modulator.

The present invention also encompasses the compositions, produced by the methods of the invention, in pharmaceutical compositions comprising a pharmaceutically acceptable carrier prepared for storage and subsequent administration, which have a pharmaceutically effective amount of the products disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

These TNF-α or IL-1 modulator compositions may be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

The pharmaceutically effective amount of the TNF-α or IL-1 modulator composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the invention, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage for the products of the present invention can range broadly depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. A variety of techniques for formulation and administration may be found in Remington's Pharmaceutical Sciences, 18th Ed., Mack Publishing Co., Easton, Pa. (1990). Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Pharmaceutical compositions suitable for use as herein described include compositions wherein the TNF-α or IL-1 modulators are contained in an effective amount to achieve the TNF-α or IL-1 modulatory purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, for example, by means of conventional mixing, dissolving, granulating, dragee-making, levitating, emulsifying, encapsulating, entrapping, or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art (see, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations).

Compounds of the present invention can be evaluated for efficacy and toxicity using known methods. For example, the toxicology of a particular compound of the present invention, or of a subset of the compounds of the present invention sharing certain chemical moieties, can be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds of the present invention in an animal model, such as mice, rats, rabbits, or monkeys, may be determined using known methods. The efficacy of a particular compound of the present invention may be established using several art recognized methods, such as in vitro methods, animal models, or human clinical trials. Art-recognized in vitro models exist for nearly every class of condition, including the conditions abated by the present invention, including cancer, cardiovascular disease, and various immune disfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound of the present invention in humans.

When used as an anti-inflammatory agent, an anti-cancer agent, a tumor-growth-inhibiting compound, or as a means of treating cardiovascular disease, the compounds of Formulae (II), (IIA), and preferably (IIB) can be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intreperitoneally, intravenously, intramuscularly, intradermally, or the like. Similarly, it may be administered topically, rectally, or vaginally, as deemed appropriate by those of skill in the art for bringing the compound of the invention into optimal contact with a tumor, thus inhibiting the growth of the tumor. Local administration at the site of the tumor or other disease condition is also contemplated, either before or after tumor resection, or as part of an art-recognized treatment of the disease condition. Controlled release formulations, depot formulations, and infusion pump delivery are similarly contemplated.

The compounds of Formulae (II) and (IIA), and preferably (IIB), when used as an antitumor agent or as a treatment for any other above-identified disease condition, may be orally or non-orally administered to a human patient in the amount of about 0.0007 mg/day to about 7,000 mg/day of the active ingredient, and more preferably about 0.07 mg/day to about 70 mg/day of the active ingredient at, preferably, one time per day or, less preferably, over two to about ten times per day. Alternatively and also preferably, the compound of the invention may preferably be administered in the stated amounts continuously by, for example, an intravenous drip. Thus, for a patient weighing 70 kilograms, the preferred daily dose of the active anti-tumor ingredient would be about 0.0007 mg/kg/day to about 35 mg/kg/day, and more preferable, 0.007 mg/kg/day to about 0.035 mg/kg/day. Nonetheless, as will be understood by those of skill in the art, in certain situations it may be necessary to administer the anti-tumor compound of the invention in amounts that excess, or even far exceed, the above-stated, preferred dosage range to effectively and aggressively treat particularly advanced or lethal tumors.

To formulate the compound of Formula (II), the compound of Formula (IIA), or the compound of Formula (IIB), as a tumor-growth-inhibiting or anti-viral compound, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound of the invention, particularly when the compound is to be administered orally.

In the case of using the compound of Formula (II), Formula (IIA), and/or Formula (IIB) as a means of treating skin redness, the compound may alternatively be administered topically as a salve or ointment, in conjunction with a pharmaceutically acceptable carrier.

In the case of using the compound of Formula (II), Formula (IIA), and or Formula (IIB) as a biochemical test reagent, as described above, the compound of the invention may be dissolved in an organic solvent or hydrous organic solvent and directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound of the invention for use as a cell cycle inhibitor is generally in the range of about 1 to about 100 µg/ml, the most appropriate use amount varies depending on the type of cultured cell system and the purpose of use, as will be appreciated by persons of ordinary skill in the art. Also, in certain applications it may be necessary or preferred to persons of ordinary skill in the art to use an amount outside the foregoing range.

The present invention also encompasses the compositions of Formula (II), Formula (IIA), and/or Formula (IIB) in a pharmaceutical compositions comprising a pharmaceutically acceptable carrier. Such compositions may be prepared for storage and for subsequent administration. Acceptable carriers or diluents for therapeutic use are well known in the pharmaceutical art, and are described, for example, in Remington's Pharmaceutical Sciences, Mack Publishing Co. (A. R. Gennaro edit. 1985). For example, such compositions may be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions of the invention, as described above, may be used alone or in combination with one another, or in combination with other therapeutic or diagnostic agents. These products can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions of the present invention may be formulated and administered either systemically or locally. A variety of techniques for formulation and administration may be found in Remington's Pharmaceutical Sciences, 18th ed., Mack Publishing Co., Easton, Pa. (1990).

Various references, publications, and patents are cited herein. To the extent permitted by law, each of these references, publications, and patents is hereby incorporated by reference herein in its entirety.

EXAMPLES

The following examples are meant to illustrate specific, preferred embodiments of the invention, and are not meant to limit the scope of protection afforded by the invention. The following examples, specifically Example 1–8, demonstrate that representative compounds of the classes of compounds described herein have been synthesized. Examples 9–17 exhibit, in mammalian cells which present an acceptable preliminary model for human efficacy and safety, treated with increasing doses of the compound of Formula (I), as synthesized in Example 1, and compounds of Formula (IIB), as herein designated TTL1 through TTL4, as synthesized in accordance with the processes of Example 1, and, more particularly, as in Examples 2–5, at concentrations as high as 10 μg/ml showed similar viability compared to untreated controls indicating that the inhibitory effects of the evaluated compounds on TNF-α synthesis were not mediated by a direct cytotoxic effect.

Subsequent studies with certain preferred compounds of the invention demonstrated that TTL1 exhibited approximately ten (10) fold greater activity compared to THE SYNTHETIC COMPOUND OF FORMULA (I) in inhibiting TNF-α and IL-1 synthesis. TTL3 which contains an additional chemical modification exhibited approximately 100 times greater activity than TTL1. It is important to note that similar to the compound of Formula (I), neither TTL1 nor TTL3 significantly inhibited IL-6 synthesis.

Example 1

Stereoselective Synthesis of Compounds of Formulae (I) and (II)

Figure 18:
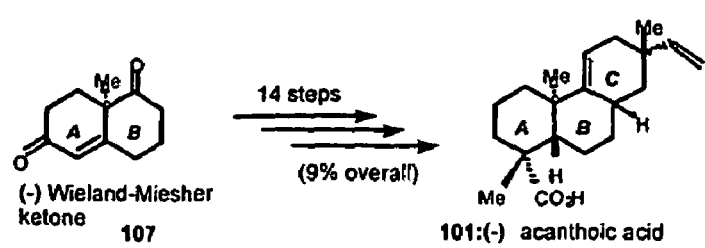
FIG. 18 depicts a summary of the synthesis of Example 1.
Figure 19:
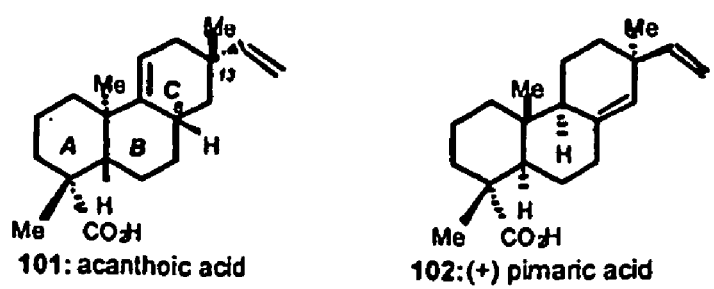
FIG. 19 depicts the structures of (−) acanthoic acid and (+) pimaric acid.

The first stereoselective synthesis of Compound of Formula (I) has been accomplished. Our synthetic plan departs from (−) Wieland-Miesher ketone (107), see FIG. 18, and calls upon a Diels-Alder cycloaddition reaction for the construction of the C ring of 101. The described synthesis confirms the proposed stereochemistry of 101 and represents an efficient entry into an unexplored class of biologically active diterpenes.

The root bark of *Acanthopanax koreanum* Nakai (Araliaceae), a deciduous shrub that grows in The Republic of Korea, has been used traditionally as a tonic, sedative, and as a remedy for rheumatism and diabetes. (*Medicinal Plants of East and Southeast Asia*, Perry, L. M.; Metzger, J. Eds.; MIT Press, Cambridge, Mass. and London, 1980). In their study of the pharmacologically active extracts of this folk medicine, Chung and co-workers have isolated and structurally characterized a novel diterpene, that was subsequently named acanthoic acid (101). ((a) Kim, Y.-H.; Chung, B. S.; Sankawa, U. *J. Nat. Prod.* 1988, 51, 1080–1083; (b) Kang, H.-S.; Kim, Y.-H.; Lee, C.-S.; Lee, J.-J.; Choi, I.; Pyun, K.-H. *Cellular Immunol.* 1996, 170, 212–221; (c) Kang, H.-S.; Song, H. K.; Lee, J.-J.; Pyun, K.-H.; Choi, I. *Mediators Inflamm.* 1998, 7, 257–259).

From the biosynthesis standpoint, 101 belongs to a rather large family of pimaradiene diterpenes, which may be best represented by pimaric acid (102). (Ruzicka, L.; Sternbach, L.; *J. Am. Chem. Soc.* 1948, 70, 2081–2085; Ireland, R. E.; Schiess, P. W. *Tetrahedron Lett.* 1960, 25, 37–43; Wenkert, E.; Buckwalter, B. L. *J. Am. Chem. Soc.* 1972, 94, 4367–4372; Wenkert, E.; Chamberlin, J. W. *J. Am. Chem. Soc.* 1959, 81, 688–693). The structure of the compound of Formula (I) is distinguished by an uncommon connectivity across the rigid tricyclic core, which may be held accountable for its pharmacological profile. Indeed, the recent isolation of this compound has allowed studies into its biological activity and verified its medicinal potential. (Kang, H.-S.; Kim, Y.-H.; Lee, C.-S.; Lee, J.-J.; Choi, I.; Pyun, K.-H. *Cellular Immunol.* 1996, 170, 212–221; Kang, H.-S.; Song, H. K.; Lee, J.-J.; Pyun, K.-H.; Choi, I. *Mediators Inflamm.* 1998, 7, 257–259)). More specifically, acanthoic acid was found to exhibit promising anti-inflammatory and antifibrotic activities that presumably arise by inhibiting the production of the pro-inflammatory cytokines: tumor necrosis factor-alpha (TNF-α) and interleukin-1 (IL-1). See *Tumor Necrosis Factors. The Molecules and their Emerging Role in Medicine*, B. Beutler, Ed.; Raven Press, N.Y. 1992; Aggarwal, B.; Puri, R. *Human Cytokines: Their Role in Disease and Therapy*; Blackwell Science, Inc.: U.S.A., 1995; Thorpe, R.; Mire-Sluis, A. *Cytokines*; Academic Press: San Diego, 1998; Kurzrock, R.; Talpaz, M. *Cytokines: Interleukins and Their Receptors*; Kluwer Academic Publishers: U.S.A., 1995; Szekanecz, Z.; Kosh, A. E.; Kunkel, S. L.; Strieter, R. M. *Clinical Pharmacol.* 1998, 12, 377–390; Camussi, G.; Lupin, E. *Drugs* 1998, 55, 613–620; Newton, R. C.; Decicco, C. P. *J. Med. Chem.* 1999, 42, 2295–2314.

This inhibition was concentration dependent and cytokine-specific since under the same conditions the production of IL-6 or IFN-γ (interferon-gamma) were not affected. In addition, acanthoic acid was found to be active upon oral administration and showed minimal toxicity in experiments performed in mice and rats.

The combination of uncommon structure and promising pharmacological activity displayed by 101 prompted us to extend our synthetic studies, see Xiang, A. X.; Watson, D. A.; Ling. T.; Theodorakis, E. A. *J. Org. Chem.* 1998, 63, 6774–6775; Ling, T.; Xiang, A. X.; Theodorakis, E. A. *Angew. Chem. Int. Ed. Engl.* 1999, 38, 3089–3091, to this family of biologically important metabolites. This example provides a stereoselective total synthesis of (−) acanthoic acid and the compounds of Formula (II) and, as shown in Examples 2–6, provides the basis for the total synthesis of the compounds of Formula (IIB). This Example also confirms the structure and absolute stereochemistry of 101.

Figure 20:
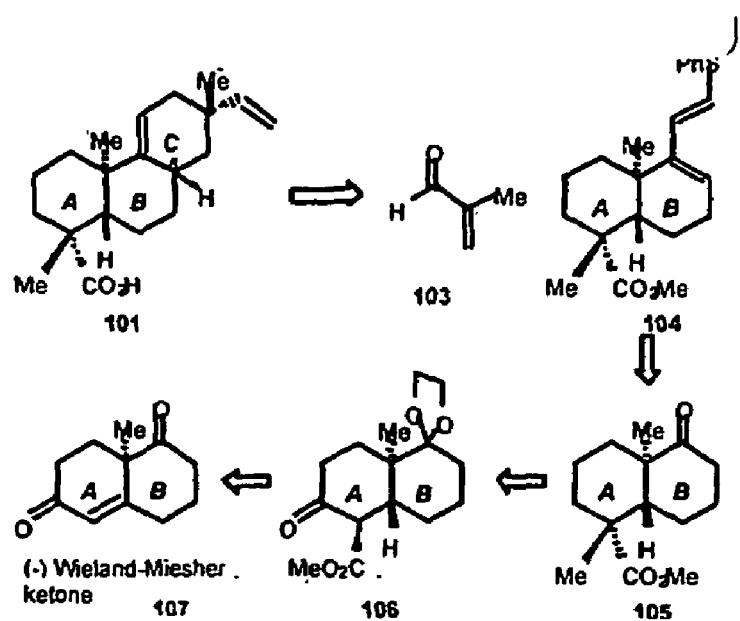
FIG. 20 depicts the retrosynthetic analysis of (−) acanthoic acid of Example 1.
Figure 21:
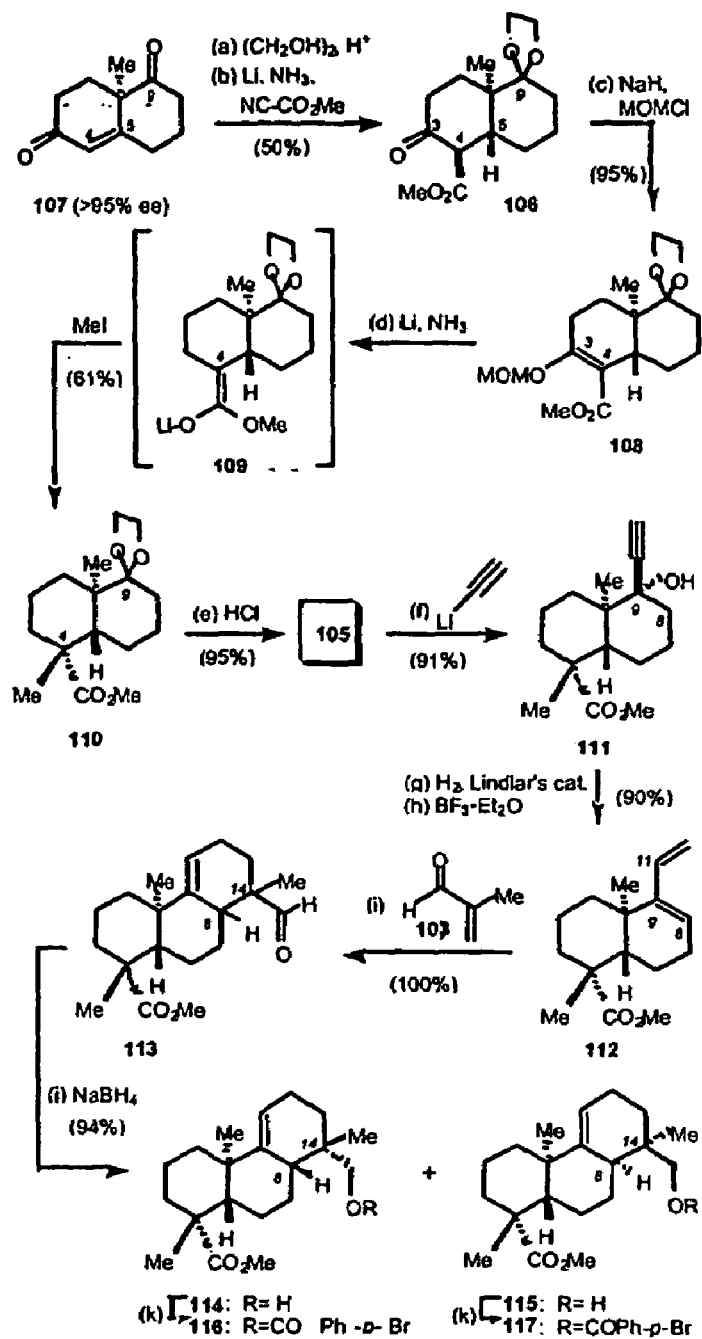
FIG. 21 depicts the synthetic scheme (Scheme 5) of preferred compounds or Formula (IIB) as described in Examples 1–6. The regents, conditions, and percentage yields of each step were as follows: (a) 0.1 equiv PTSA (CH$_2$OH)$_2$, benzene, 80° C., 4 h, 90%; (b) 2.2 equiv Li, liquid NH$_3$, 1.0 equiv tBuOH, −78 to −30° C., 30 minu then isoprene (excess), −78 to 50° C.; 1.1 equiv NC—CO$_2$Me, Et$_2$O, −78 to 0° C., 2 h, 55%; (c) 1.1 equiv NaH, HMPA, 25° C., 3 h; 1.1 equiv MoMCl, 25° C., 2h, 95%; (d) 7.0 equiv Li, liquid NH$_3$, −78 to −30° C., 20 min; CH$_{13}$I (excess), −78 to −30° C., 1 h, 61%; (e) 1N HCl, THF, 25° C., 15 min, 95%; (f) 1.6 equiv Li acetylide, Et$_2$O, 25° C., 1 h, 91%; (g) Lindlar's catalyst (20% per weight), H$_2$, dioxane/pyridine 10/1. 25°, 10 min 95%; (h) 4.4 equiv BF$_3$.Et$_2$O, benzene/THF4/1. 80° C., 5 h, 95%; (i) 13 equiv compound 103, neat, 8 h, 25° C., 100%; (j) 1.4 equiv NaBH$_4$, THF MeOH: 10/1, 30 min, 25° C., 94%; (k) 1.1 equiv p-Br—C$_6$H$_4$COCl, 1.5 equiv pyridine, 0.1 equiv DMAP, CH$_2$Cl$_2$, 25°, 2 h, 95% for compound 116, 97% for compound 117.
Figure 23:
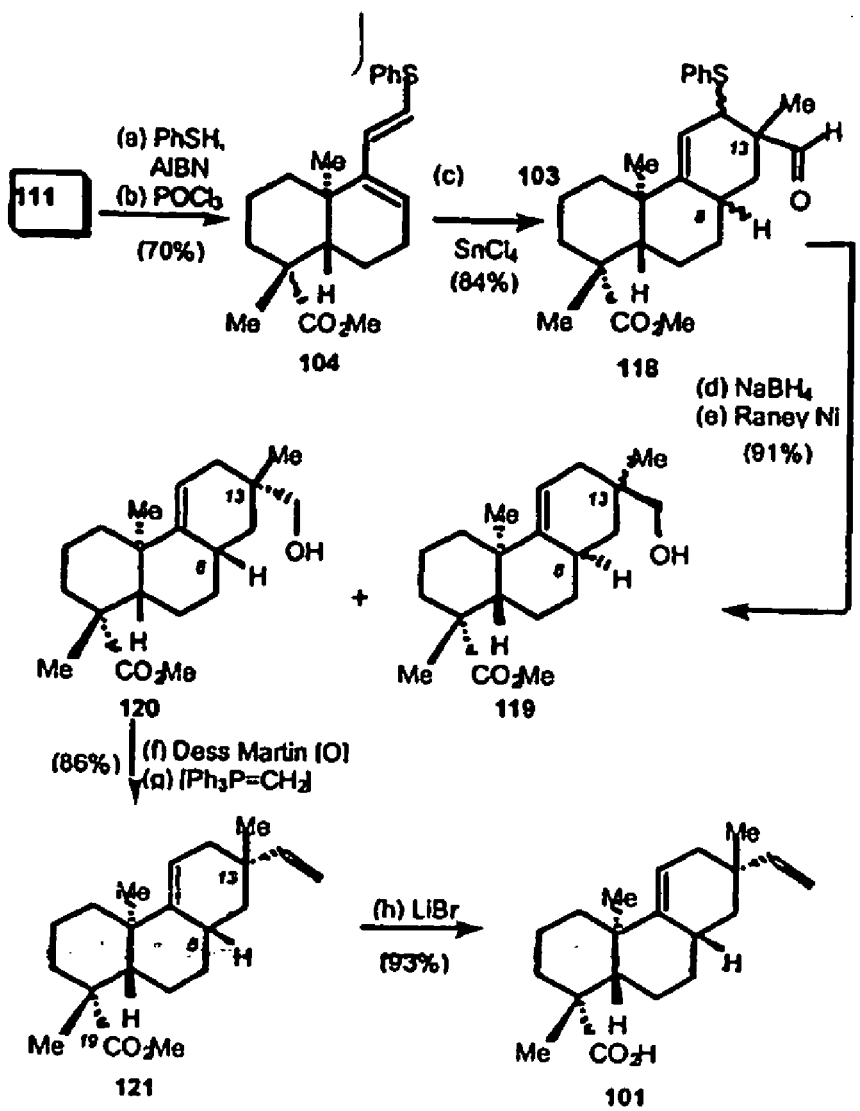
FIG. 23 depicts the synthetic scheme (Scheme 6) of the tricyclic core of (−) acanthoic acid of Example 1. The reagents, conditions, and percentage yields of each step were as follows: (a) 3.0 equiv PhSH, 0.05 equiv AIBN, xylenes, 120° C., 18 h, 86%, (b) 1.1 equiv. POCl$_3$, HMPA, 25° C., 1 h; 1.1 equiv pyridine, 150° C., 18 h 81%; (c) 3.0 equiv compound 103, 0.2 equiv SnCl$_4$ (1 M in CH$_2$Cl$_2$), CH$_2$Cl$_2$, −20 to 0° C., 20 h, 84%; (d) 1.4 equiv NaBH$_4$, EtOH, 25° C., 30 min; (e) RaneyNi (excess), THF, 65° C., 10 min 91% (over two steps); (f) 1.3 equiv Dess-Martin periodinane, CH$_2$Cl$_2$, 25° C., 30 min; (g) 2.7 equiv P$_3$PhCH$_3$Br, 2.2. equiv NaHMDS (1.0 in THF), THF, 25° C., 18 h, 86% (over two steps); (h) 3.0 LiBr, DMF, 160° C., 3 h, 93%.
Figure 24:
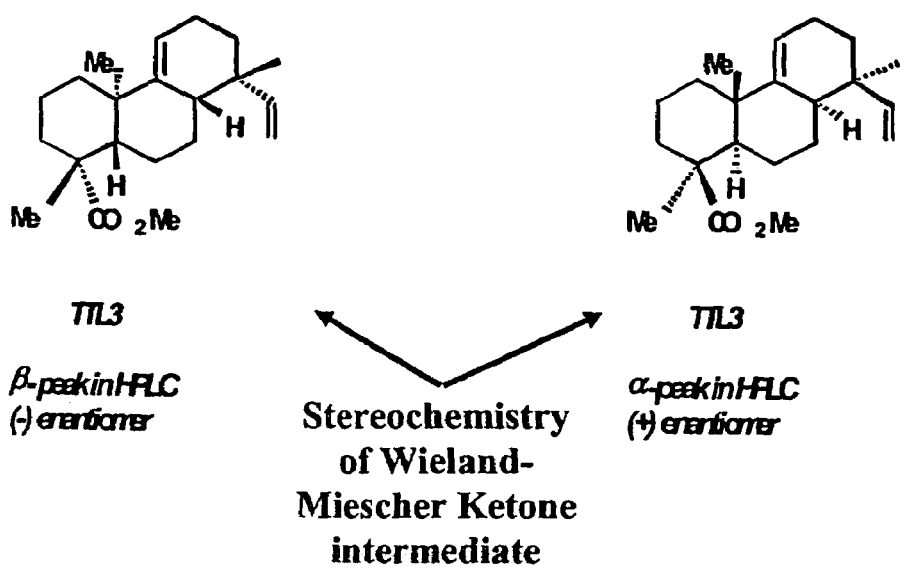
FIG. 24 depicts two enantiomers of the compounds designated TTL herein, exhibiting the ability to locate the moiety designated R$_6$ stereo-selectively.
Figure 25:
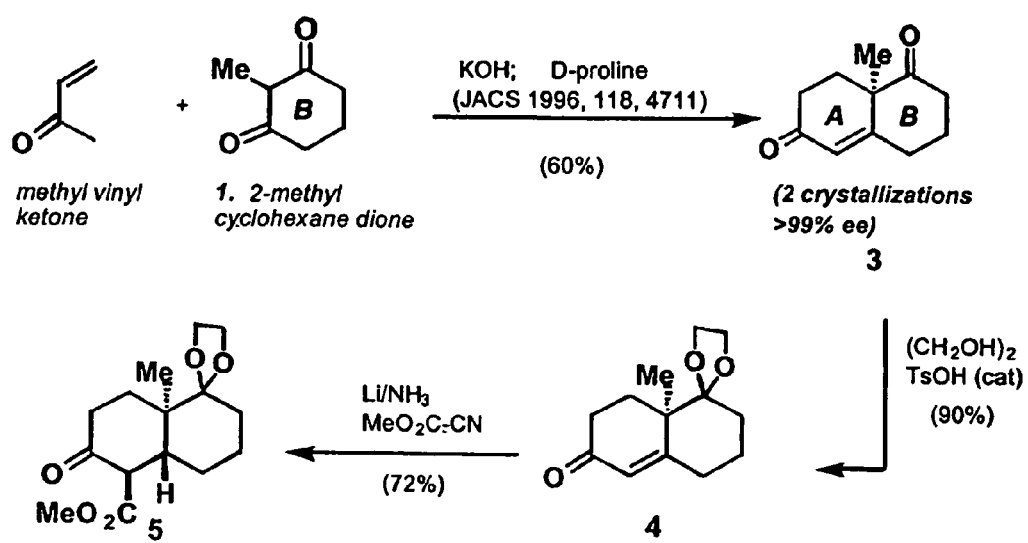
FIG. 25 depicts a method of synthesizing the (−) enantiomer depicted in FIG. 23; the (+) enantiomer depicted in FIG. 23 may be synthesized by using (L)-proline in place of (D)-proline.
Figure 26:
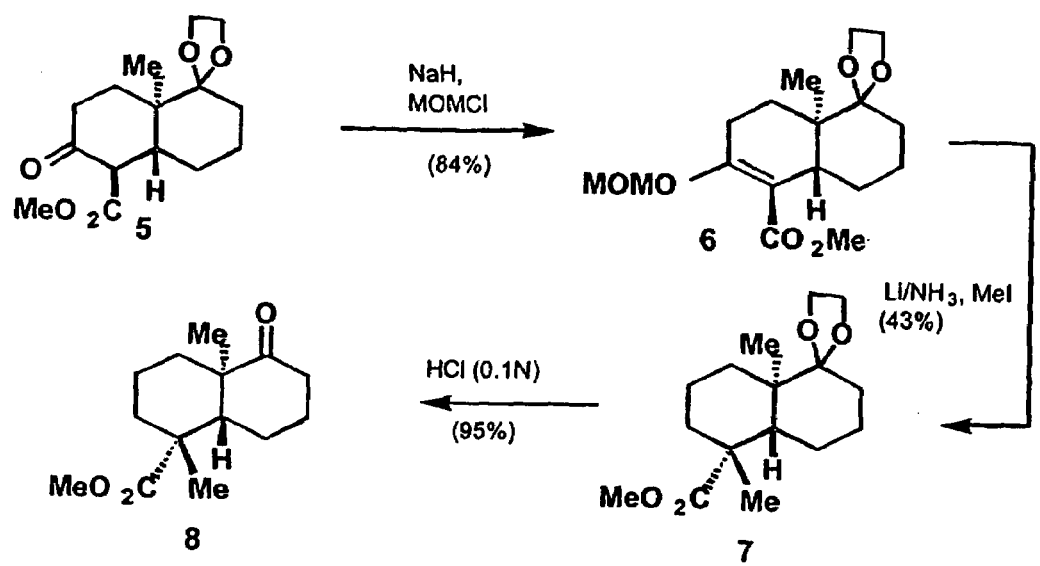
FIG. 26 depicts synthetic steps subsequent to those depicted in FIG. 24.
Figure 27:
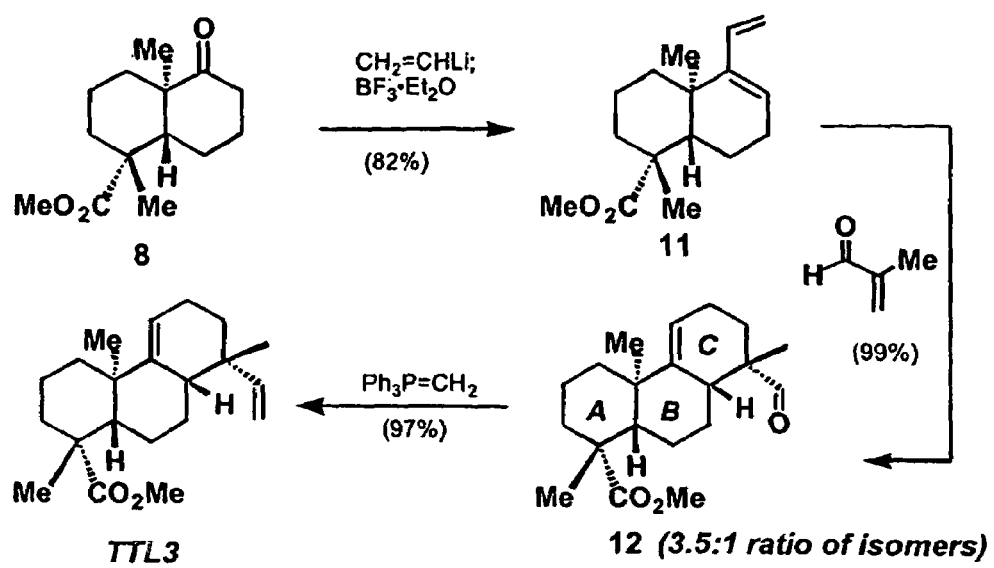
FIG. 27 depicts the use of the synthetic route disclosed to locate the moieties designated R9, R10 and R11, in the compound of Formula IIB and its stereo-isomers in a stereo-specific manner on the ring.
Figure 28:
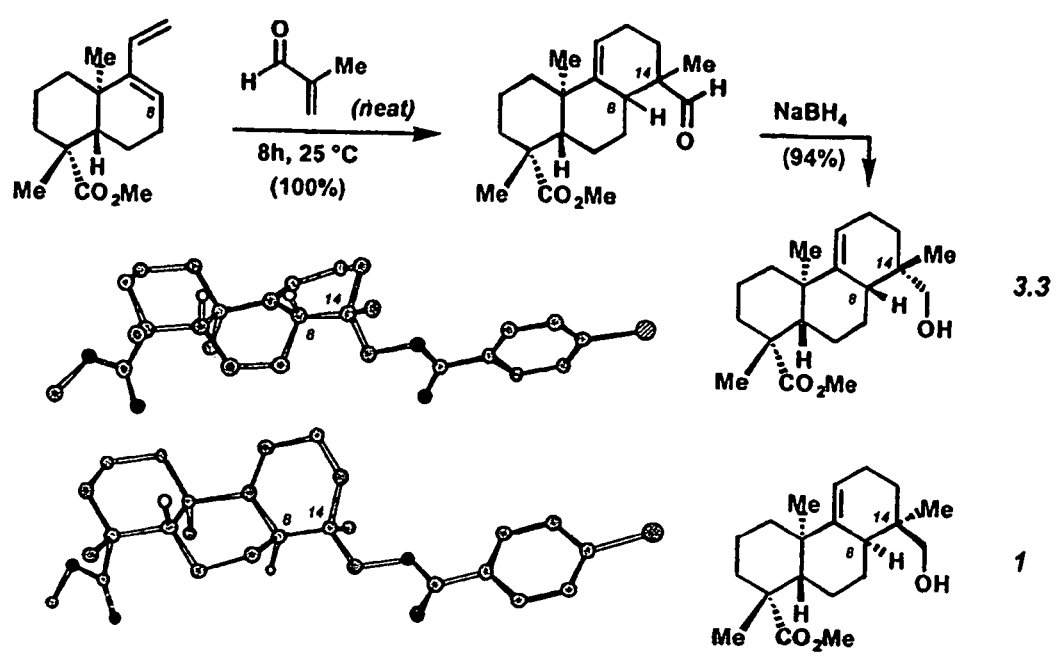
FIG. 28 depicts the synthesis, isolation and purification of the compound of Formula IIB and its stereo-isomers, showing how to purify compounds in which to locate the moieties designated R9, R10 and R11 of in the compounds of Formula IIB and its stereo-isomers, in a stereo-specific manner on the ring.
Figure 29:
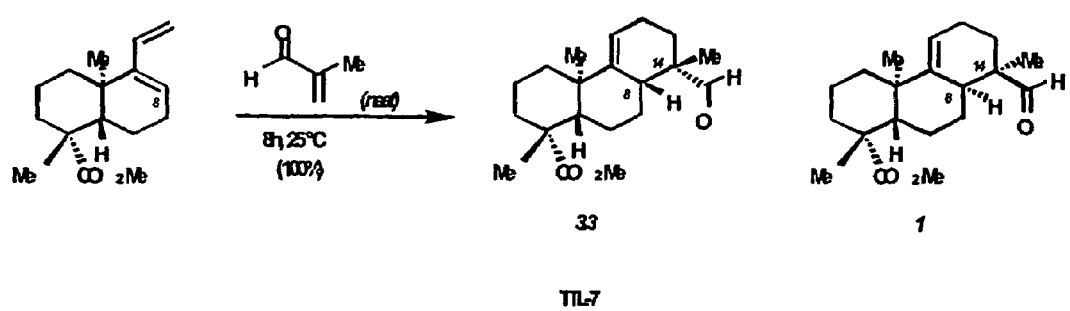
FIG. 29 also depicts the synthesis, isolation and purification of the compound of Formula IIB and its stereo-isomers, showing how to purify compounds in which to locate the moieties designated R9, R10 and R11 of in the compounds of Formula IIB and its stereo-isomers, in a stereo-specific manner on the ring.

The retrosynthetic strategy towards acanthoic acid is illustrated in FIG. 20. The C ring of 101 is envisioned to be constructed by a Diels-Alder cycloaddition reaction, thereby revealing dienophile 103 and an appropriately substituted diene, such as 104, as ideal coupling partners. See Oppolzer, W in *Comprehensive Org Synthesis*, Trost, B. M. Ed.; Oxford, N.Y.; Pergamon Press, 1991, 315–399. This reaction introduces both the unsaturation at the C9–C11 bond and the desired stereochemistry at the C8 and C13 carbons, permitting a convenient branch point between the syntheses of the compounds of Formula (II) and the compounds of Formula (IIB). Diene 104 could be produced by functionalization of ketone 105, whose C4 quaternary center was projected to be formed by a stereocontrolled alkylation of β-ketoester 107. This analysis suggested the use of (−) Wieland-Miesher ketone 107 as a putative starting material. Application of such a plan to the synthesis of acanthoic acid is depicted in FIGS. 21 and 23, as Schemes 5 and 6. All compounds exhibited satisfactory spectral and analytical data.

The synthesis began with optically pure enone 107, which was readily available through a D-proline-mediated asymmetric Robinson annulation (75–80% yield, >95% ee). See Buchschacher, P.; Fuerst, A.; Gutzwiller, J. *Org. Synth. Coll. Vol. VII* 1990, 368–3372.). Selective ketalization of the C9 ketone group of 107, followed by reductive alkylation across the enone functionality with methyl cyanoformate afforded ketoester 106 in 50% overall yield. See Crabtree, S. R.; Mander, L. N.; Sethi, P. S. *Org. Synth.* 1992, 70, 256–263. To introduce the desired functionalization at the C4 position, a second reductive alkylation procedure was implemented, see Coates, R. M.; Shaw, J. E. *J. Org. Chem.* 1970, 35, 2597–2601; Coates, R. M.; Shaw, J. E. *J. Org. Chem.* 1970, 35, 2601–2605. Compound 106 was first transformed to the corresponding methoxymethyl ether 108, which upon treatment with lithium in liquid ammonia and iodomethane gave rise to ester 110 in 58% overall yield and as a single diastereomer. See Welch, S. C.; Hagan, C. P. *Synthetic Comm.* 1973, 3, 29–32; Welch, S. C.; Hagan, C. P.; Kim, J. H.; Chu, P. S. *J. Org. Chem.* 1977, 42, 2879–2887; Welch, S. C.; Hagan, C. P.; White, D. H.; Fleming, W. P.; Trotter, J. W. *J. Amer. Chem. Soc.* 1977, 99, 549–556. The stereoselectivity of this addition arose from the strong preference of the intermediate enolate 109 to undergo alkylation at the less hindered equatorial side.

Figure 22:
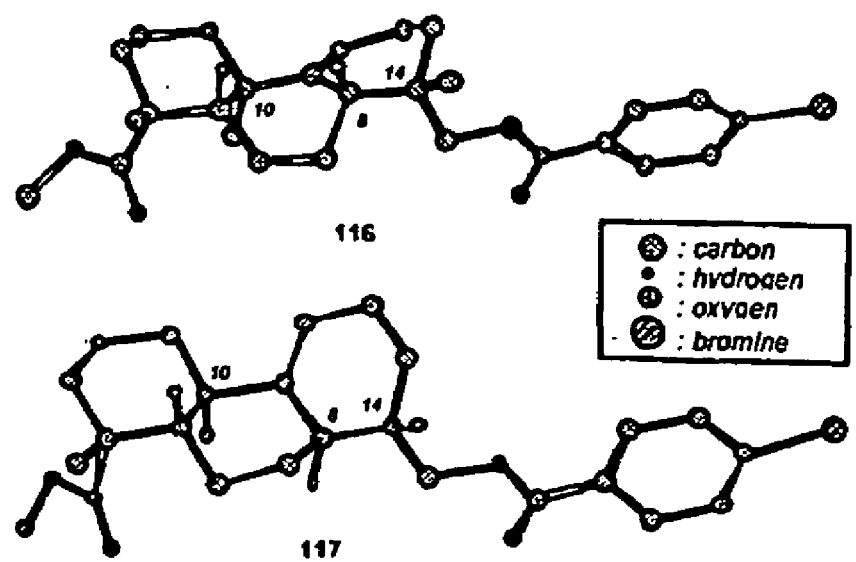
FIG. 22 depicts the Chem3D representation of ORTEP drawings of compound 116 and 117, showing only selected hydrogen atoms for sake of clarity.

With the bicyclic core at hand, the C ring was constructed. The C-ring was formed via a Diels-Alder reaction between methacrolein 103, see for example, FIG. 21, and the sulfur-containing diene 104. The synthesis of 104 was initiated with an acid-catalyzed deprotection of the C9 ketal of 110, followed by alkylation of the resulting ketone 105 with lithium acetylide•ethylene diamine complex. See Das, J.; Dickinson, R. A.; Kakushima, M.; Kingston, G. M.; Reid, G. R.; Sato, Y.; Valenta, Z. *Can. J. Chem.* 1984, 62, 1103–1111). This sequence afforded alkyne 111 as an 8:1 diasteromeric mixture at C9 (in favor of the isomer shown) and in 86% overall yield. At this point, the diastereofacial selectivity of the Diels-Alder reaction was evaluated, as was the overall feasibility of using a non-functionalized diene, such as 112. To this end, the diastereomeric mixture of propargyl alcohols 111 was partially reduced ($H_2$, Lindlar's catalyst) and dehydrated ($BF_3.Et_2O$) to produce diene 112 in 90% yield. (Coisne, J.-M.; Pecher, J.; Declercq, J.-P.; Germain, G.; van Meerssche, M. *Bull. Soc. Chim. Belg.* 1980, 89, 551–557). The Diels-Alder cycloaddition between 112 and methacrolein (103) under neat conditions at 25° C., afforded in quantitative yield a mixture of two diastereomeric aldehydes that were separated after reduction with sodium borohydride. The resulting alcohols 114 and 115 were transformed to the corresponding p-bromobenzoate esters (compounds 116 and 117 respectively), which upon recrystallization with dichloromethane/ethanol yielded crystals suitable for X-Ray analysis (FIG. 22).

The results of the X-ray analyses established that the tricyclic system had the expected stereochemistry at the C4 position and confirmed that the Diels-Alder reaction proceeded with exclusive endo orientation. Methacrolein was shown to produce exo Diels Alder products when reacting with cyclopentadiene: Kobuke, Y.; Fueno, T.; Furukawa, J. *J. Am. Chem. Soc.* 1970, 92, 6548–6553. This surprising observation was rationalized based on the steric repulsion exhibited by the methyl group: Yoon, T.; Danishefsky, S. J.; de Gala, S. *Angew. Chem. Int. Ed. Engl.* 1994, 33, 853–855). Second, after reduction, the major product of the cycloaddition was shown to be alcohol 114, which had the desired stereochemistry at the C8 center, thereby demonstrating a strong preference of diene 112 to undergo reaction with 103, see for example, FIG. 21, from the α-face (bottom side attack). Moreover, these data indicated that synthesis of acanthoic acid would require an inversion in the orientation of the incoming dienophile.

As discussed in Example 2–8, below, absent inversion of the incoming dienophile, the wholly novel compounds of Formula (IIB) were synthesized. The choice of an appropriate substituted dienophile allows essentially limitless selection of the $R_{11}$, and $R_{12}$ groups of the compounds of Formula (IIB).

The inversion of the dienophile required for the synthesis of the compound of Formula (I), its naturally occurring analogs, and the compounds of Formula (II) and (IIA), was accomplished by altering the atomic orbital coefficients at the termini of the diene, supporting the use of a heteroatom-containing diene, such as 104, during the cycloaddition. See generally Overman, L. E.; Petty, C. B.; Ban, T.; Huang, G. T. *J. Am. Chem. Soc.* 1983, 105, 6335–6338; Trost, B. M.; Ippen, J.; Vladuchick, W. C. *J. Am. Chem. Soc.* 1977, 99, 8116–8118; Cohen, T.; Kozarych, Z. *J. Org. Chem.* 1982, 47, 4008–4010; Hopkins, P. B.; Fuchs, P. L. *J. Org. Chem.* 1978, 43, 1208–1217; Petrzilka, M.; Grayson, J. I. *Synthesis,* 1981, 753–786). The construction of diene 104 and its utilization for the synthesis of 101 is shown in FIG. 23, Scheme 6.

Compound 104 was produced by a radical addition of thiophenol onto alkyne 111 (Greengrass, C. W.; Hughman, J. A.; Parsons, P. J. *J. Chem. Soc. Chem. Commun.* 1985, 889–890), followed by $POCl_3$-mediated dehydration of the resulting allylic alcohol (Trost, B. M.; Jungheim, L. N. *J. Am. Chem. Soc.* 1980, 102, 7910–7925; Mehta, G.; Murthy, A. N.; Reddy, D. S.; Reddy, A. V. *J. Am. Chem. Soc.* 1986, 108, 3443–3452) (2 steps, 70% yield). Interestingly, this dehydration was also attempted with $BF_3.Et_2O$, but proved ineffective in this case. With a substantial amount of 104 at hand, we investigated the Diels-Alder reaction, using 103 as the dienophile. Several thermal—(−78 to 80° C.) and Lewis acid—($BF_3.Et_2O$, $TiCl_4$, $AlCl_3$ and $SnCl_4$) catalyzed Diels-Alder conditions were tested. Best results were obtained with $SnCl_4$ in methylene chloride at −20° C. and afforded aldehyde 118 in 84% yield as a 4.2:1 mixture of diastereomers. To simplify the product characterization and allow adequate separation, this mixture was reduced with $NaBH_4$ and reductively desulfurized using Raney Ni. Alcohols 119 and 120 were thus obtained in 91% overall yield. The structure of these compounds was assigned by comparison to the products isolated from the reaction between 103 and 112. Treatment of the major diastereomer 120 with Dess-Martin periodinane, followed by Wittig methylenation installed the alkene functionality at the C13 center and produced 121 in 86% overall yield. The C-19 carboxylic acid was then deprotected. Exposure of 121 to LiBr in refluxing DMF gave rise to acanthoic acid 101 in 93% yield via an $S_N^2$-type displacement of the acyloxyl functionality. See Bennet, C. R.; Cambie, R. C. Tetrahedron 1967, 23, 927–941. Synthetic 101 had identical spectroscopic and analytical data with those reported for the natural product.

This Example provides a concise, stereoselective synthesis of Compound 101. The synthetic strategy is highlighted by the implementation of a Diels-Alder reaction between diene 104 and methacrolein (103), which set the stereochemistry at the C13 and C8 carbon centers. The described synthesis of 101 requires fourteen steps (starting with enone 107) and proceeds in approximately 9% overall yield. The overall efficiency and versatility of our strategy sets the foundation for the preparation of designed analogs with improved pharmacological profiles.

Examples 2–8

Stereoselective Synthesis of Compounds of Formula (IIB)

The procedure outline in Example 1, and depicted in FIG. 23, Scheme 6, may be modified or truncated to yield the compounds of Formula (II) or Formula (IIB).

Example 2

The compound herein designated TTL4 was synthesized by following the procedures of Example 1, as depicted in FIG. 21, to yield compound 114, herein designated TTL4.

Example 3

The compound herein designated TTL2 was synthesized by following the procedures of Example 1, as depicted in FIG. 21, to yield compound 114. Similar to the reaction depicted in FIG. 23, step (h), the compound 114 was then reacted with 3.0 equivalents LiBr, in DMF, at 160° C., for approximately three hours, to a yield of approximately 93% of the compound herein designated TTL2.

Example 4

Figure 14:
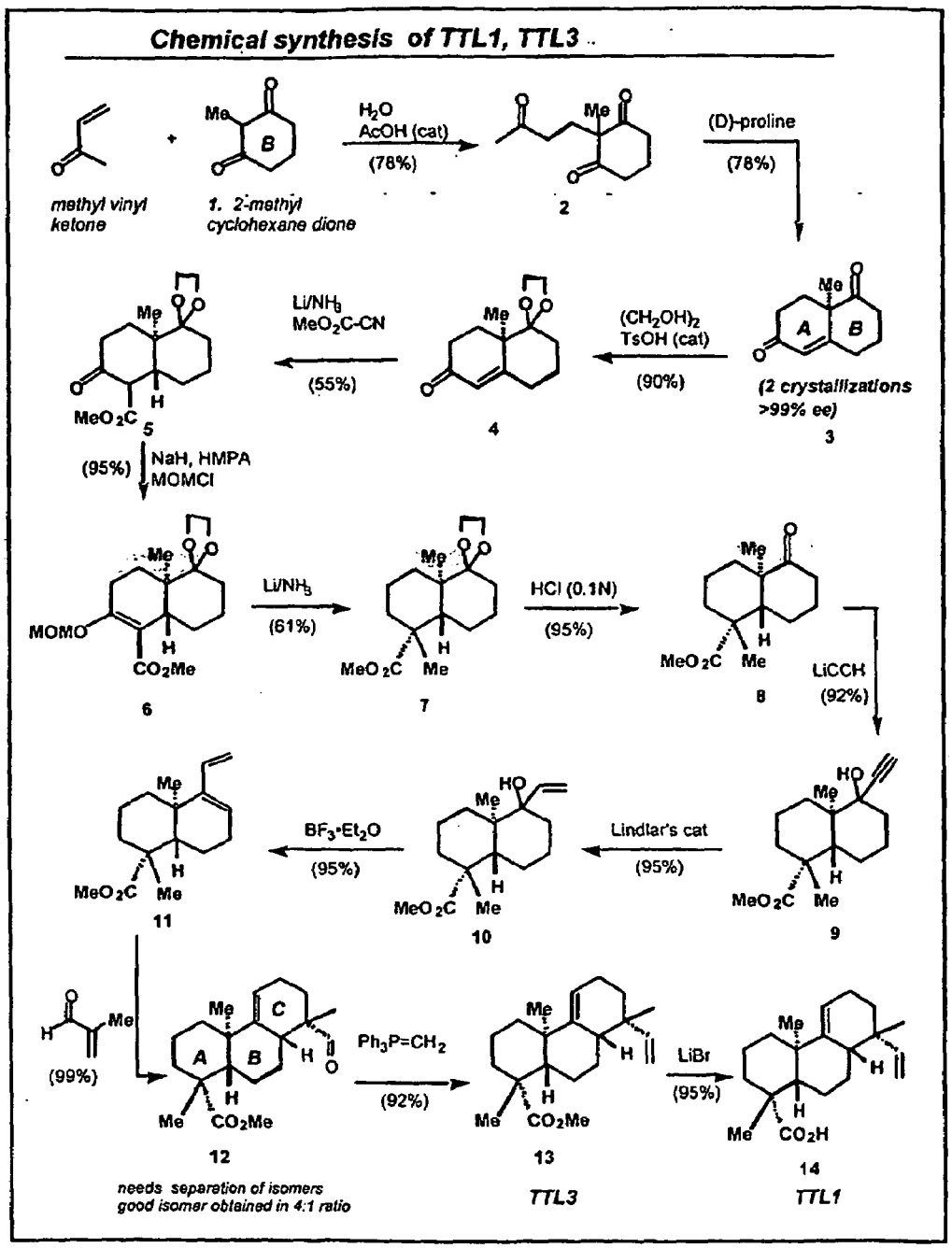
FIG. 14 depicts a complete chemical synthesis of certain compounds of the invention, identified herein as TTL1 and TTL3 in FIG. 17.
Figure 15:
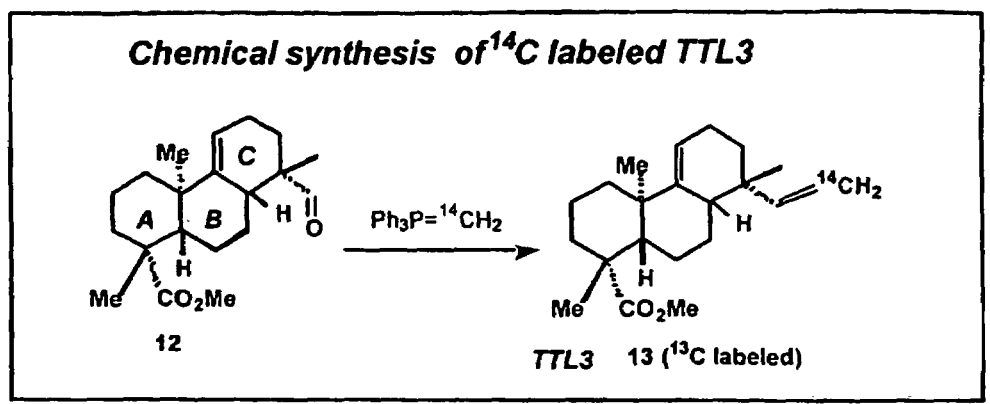
FIG. 15 depicts a chemical synthesis of a preferred $^{14}$C-labeled compound of the invention, identified as TTL3 in FIG. 17.
Figure 16:
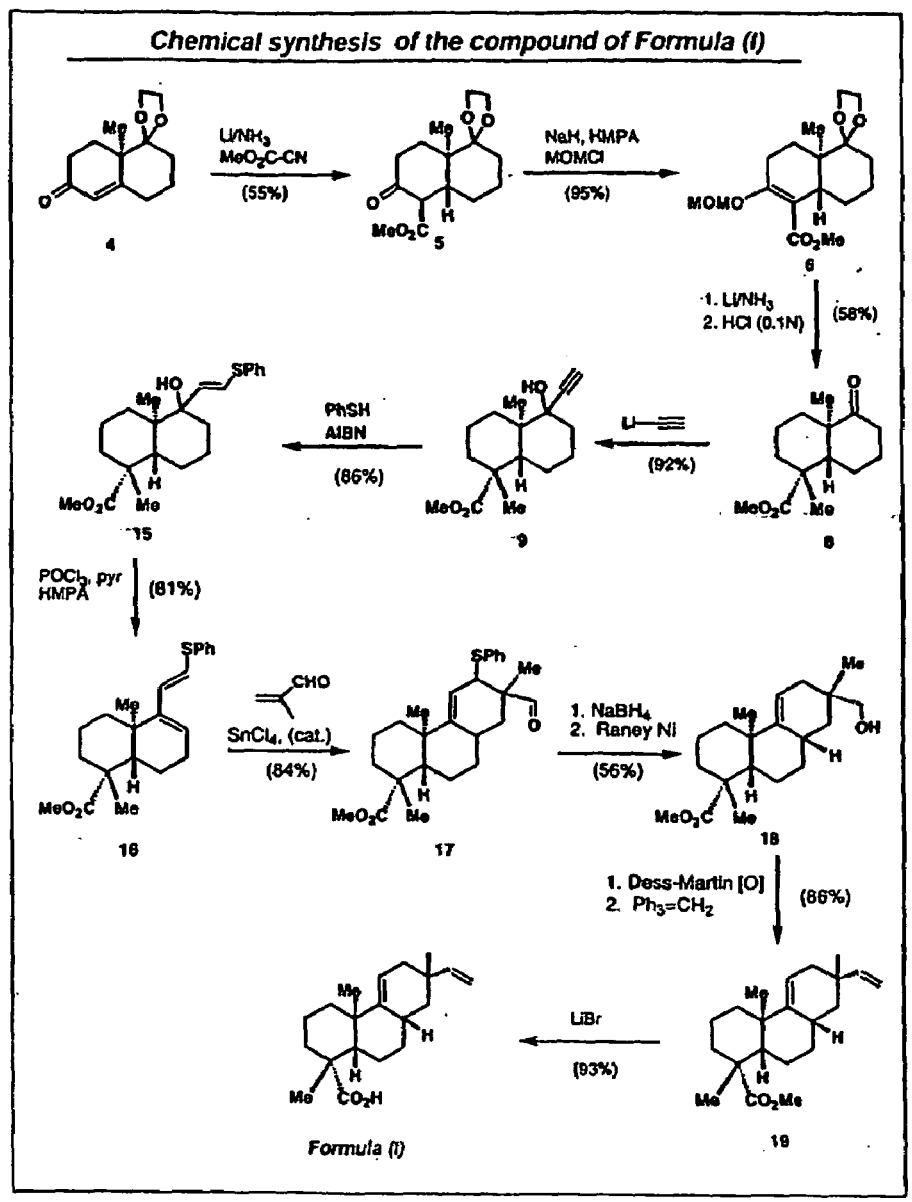
FIG. 16 depicts the complete chemical synthesis of the compound of Formula (I).

The compound herein designated TTL3 was synthesized by following the procedures as depicted in FIG. 14, to yield compound 13. This compound is herein designated TTL3.

Example 5

The compound herein designated TTL1 was synthesized by following the procedures as depicted in FIG. 14, to yield compound 13. This compound is herein designated TTL1.

Example 6

A compound of Formulae (IIB) wherein $R_{15}$ is a hydrogen and $R_9$ and $R_{15}$ are separately selected from the group consisting of $C_1$–$C_6$ alkyl, and $C_1$–$C_6$ substituted alkyl is synthesized by following the procedures therefor of Example 1, except that the dienophile is selected from one of the compound of Formulae (III) wherein $R_{15}$ is a hydrogen and $R_9$ and $R_{15}$ are separately selected from the group consisting of $C_1$–$C_6$ alkyl, and $C_1$–$C_6$ substituted alkyl, as in this Example.

Example 7

Specifically, a compound of Formulae (IIB) wherein $R_{14}$ is a hydrogen and $R_9$ and $R_{15}$ are separately selected from the group consisting of $C_1$–$C_6$ alkyl, and $C_1$–$C_6$ substituted alkyl is synthesized by following the procedures therefor of Example 1, except that the dienophile is selected from one of the compound of Formulae (III) wherein $R_{14}$ is a hydrogen and $R_9$ and $R_{15}$ are separately selected from the group consisting of $C_1$–$C_6$ alkyl, and $C_1$–$C_6$ substituted alkyl, as in this Example.

Example 8

A compound of Formulae (IIB) wherein $R_{14}$ is a hydrogen, and $R_9$ and $R_{15}$ are separately selected from $C_2$–$C_6$ alkenyl, $C_2$–$C_6$ substituted alkenyl, $C_1$–$C_6$ alcohol, and $C_5$–$C_6$ aryl, is synthesized by following the procedures therefor of Example 1, except that the dienophile is selected from one of the compound of Formulae (III) wherein $R_{14}$ is a hydrogen and $R_9$ and $R_{15}$ are separately selected from $C_2$–$C_6$ alkenyl, $C_2$–$C_6$ substituted alkenyl, $C_1$–$C_6$ alcohol, and $C_5$–$C_6$ aryl, as in this Example.

Examples 9–17

Materials and Methods.

Murine macrophage cells RAW 264.7 ($1 \times 10^6$/ml) were pretreated for 30–60 minutes with varying doses of the synthetic compound of Formula (I), the synthetic compound of formula (I) and a panel of analogs (diluted in 0.5% DMSO) prior to stimulation with various agents such as lipopolysaccharide (LPS) or a gram positive agent like heat-killed Staph aureus (SAC). Supernatants collected over a 72-hour period will be assayed for the levels of TNF-α, IL-1, IL-6, IL-10, IL-12 and other cytokines either by elisa or bioassay. Additional studies to evaluate the effects of the synthetic compound of Formulae (I), (II), (IIA) and (IIB) on cytokine signaling pathways such as, for example, Caspase-activity (Nr-1, Nr.3), transcription factors such as NF-kB, MAP-kinase activity (p38, ERK and JNK) will also be performed.

Results

Preclinical studies demonstrated that murine RAW 264.7 cells treated with increasing doses of the synthetic compounds of Formulae (I) and (IIB), specifically those designated TTL1 and TTL3 herein, at concentrations as high as 10 ug/ml showed similar viability compared to untreated controls indicating that the inhibitory effects of the synthetic compounds of Formulae (I) and (IIB) on TNF-α synthesis were not mediated by a direct cytotoxic effect.

Subsequent studies with the compound of Formula (I) as synthesized according to Example 1, TTL1 (as synthesized according to Example 2) and TTL3 (as synthesized according to Example 4) demonstrated that TTL1 exhibited approximately 10 fold greater activity compared to the compound of Formula (I) as synthesized according to Example 1 in inhibiting TNF-α and IL-1 synthesis. TTL3, as synthesized according to Example 4, contains an additional chemical modification exhibited approximately 100 times greater activity than TTL1, as synthesized according to Example 2. It is noted that similar to the compound of Formula (I) as synthesized according to Example 1, neither analog TTL1 nor TTL3 significantly inhibited IL-6 synthesis. TTL1 exhibited a ten (10)-fold greater activity compared to the compound of Formula (I) as synthesized according to Example 1 in inhibiting TNF-α and IL-1 synthesis.

TTL3 which contains an additional chemical modification exhibited approximately 100 times greater activity than TTL1. It is again important to note that similar to the compound of Formula (I) as synthesized according to Example 1, neither analog significantly inhibited IL-6 synthesis.

Example 18

Synthesis of compounds have alternative stereo-structure at ring position covalently bound to $R_6$. Various diastereomers of the compounds designated TTL1–TTL5 herein designated were prepared and isolated by (a) using L-proline in place of D-proline in the Robinson cyclization of triketone 2 to enone 3 and/or (b) purifying the stereoisomers at position C14 that were produced via the Diels-Alder reaction between diene 104 and methacrolein (103). Selection of the stereo-structure at these two chiral centers allows for the selection and isolation of four distinct diasteriomers corresponding to each TNF-α modulator herein described.

More specifically, the enantiomers at the ring position covalently linked to the R6 moiety, were synthesized by modifying the procedures depicted in FIG. 14 as follows: (L)-proline replaced (D)-proline in the Robinson cyclization of triketone 2 to enone 3. The cyclization utilizing L-proline thus afforded the (+) enantiomer of enone 3. FIG. 14 was otherwise followed using the same reactions and conditions as shown. The resulting product was the (+) enantiomer of TTL3.

Similarly, as noted above, the Diels-Alder reaction between diene 104 and methacrolein (103) sets the stereochemistry at the C13 and C8 carbon centers, or the C14 and C8 carbon centers depending on the orientation of the dienophile. Accordingly, the methods disclosed herein permit the synthesis and purification, and hence the use, of at least the diasteromers of the following compounds:

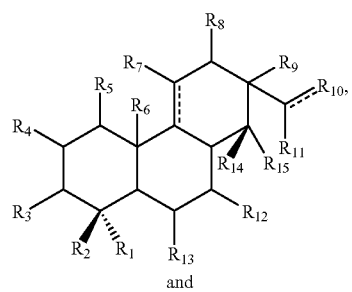

and

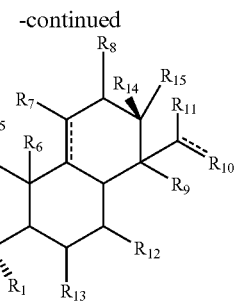

-continued wherein $R_1$–$R_{15}$ are as defined previously, and the chirality at the ring position directly covalently bound to $R_6$ and at the ring position designated $C_{14}$ (directly covalently bound to $R_{14}$ and $R_{15}$ in the former structure and to $R_9$ in the latter) may be separately selected from either (−) or (+), or may represent a racemic mixture of enantiomers. These structures are to be understood as within the meaning of the structures of Formulae (II) and (IIB), as those term are used herein.

Exemplary of the synthetic routes and routes of isolation, as well as certain of the disclosed diastereomers, are depicted in FIGS. 24, 25, 26, 27, 28 and 29.

Examples 19–21

Murine Macrophage and Human Macrophage cell-based assays were completed to test the activity of stereo-isomers, produced and isolated as described in Example 18, of the compound TTL3.

Example 19

LPS Stimulation of Human Macrophage Cell Line THP-1. Human monocytic THP-1 cells were washed in complete RPMI-1640 medium (CRPMI; contains 10% heat inactivated fetal calf serum, with 2 mM L-glutamine, 10 mM Hepes, 1 mM sodium pyruvate, 4.5 g/L glucose, 1.5 gL bicarbonate and 0.05 mM 2-mercaptoethanol) at 1000 rpm for 5 minutes and counted. To induce maturation, THP-1 cells were plated at a density of $1\times10^6$ cells/ml in either 24 or 96 well plates (Costar) and pretreated with 5 nM phorbol myristate acetate (PMA) for three days. After three days, the CRPMI was discarded and new medium added. Lipopolysaccharide (LPS, *E. coli* serotype 0111:B4 or 055:B5), was diluted to a 1 mg/ml stock in phosphate-buffered saline and stored at −80° C. Prior to use, the LPS was thawed and vortexed for 30 minutes. To evaluate the effect of different isoforms of TTL3 (including enantiomers, analogs, diastereomers) on LPS induced TNF-α production, cells were treated with the compounds for 1 hour, followed by a 5 hour incubation with 2 ug of LPS. A p38 kinase inhibitor SB203580 (Sigma) was used as a positive control (10 nM).

Example 20

LPS Stimulation of Murine Macrophage Cell Line RAW-264.7. RAW 264.7 cells were plated at $1\times10^5$ cells/well of a 24 well plate and allowed to adhere and spread overnight at 37° C. The next day, the media was replaced with fresh media (1 ml/well), and the cells were allowed to incubate for 15 to 20 minutes prior to pretreatment with inhibitors. Inhibitors tested include TTL3 enantiomer peaks A and B and a control inhibitor of p38 MAP kinase, SB203580. A 200× stock of each inhibitor was prepared in 100% DMSO in borosilicate glass vials, and 5 ul of this solution was added per well and mixed immediately. DMSO alone (0.5% DMSO in media) served as the vehicle control. The cells were pretreated with the inhibitors for 1 hour at 37° C. at concentrations ranging from 10 pg/ml to 10 ug/ml final concentration. A 100× stock of the LPS was prepared in media and added to the cells at a final concentration of 1 ug/ml. The cells were stimulated for 12 to 24 hours after which the supernatants were harvested and assayed for TNF-α by ELISA (Biosource).

Example 21

Example of human TNF-α ELISA Methodology. Supernatants were collected and stored at −80° C. until testing in a specific TNF-α ELISA. ELISA plates were coated with 100 uL/well of TNF-α capture antibody at 5 ug/ml for 20 hours at 4° C. Plates were washed 2 times with wash buffer and blocked by adding 300 uL/well of blocking solution for 2 hours at room temperature. Plates were washed 4 times and reconstituted with standards and samples added at 100 uL/well. At the same time 50 uL/well of biotinylated antibody (4 ug/mL) were added and incubated for 2 hours at room temperature with continual shaking (700 rpm). Plates were washed 4 times and strepavidin-HRP working solution was added for 30 minutes at room temperature. 100 uL/well of TMB was added for 30 minutes and the reaction was stopped by adding 50 uL/well of 1.8 N $H_2SO_4$.

Examples 19–21 also demonstrate the surprising ability of both the A and B enantiomers of TTL3 to inhibit TNF-α synthesis. In the above assays of Examples 19–21, no significant differences were observed with respect to the ability of these stereo-isomer to inhibit TNF-α synthesis.

Example 22

Strategy for Synthesis of TTL3 Analogs

A. Strategy 1

Figure 30:
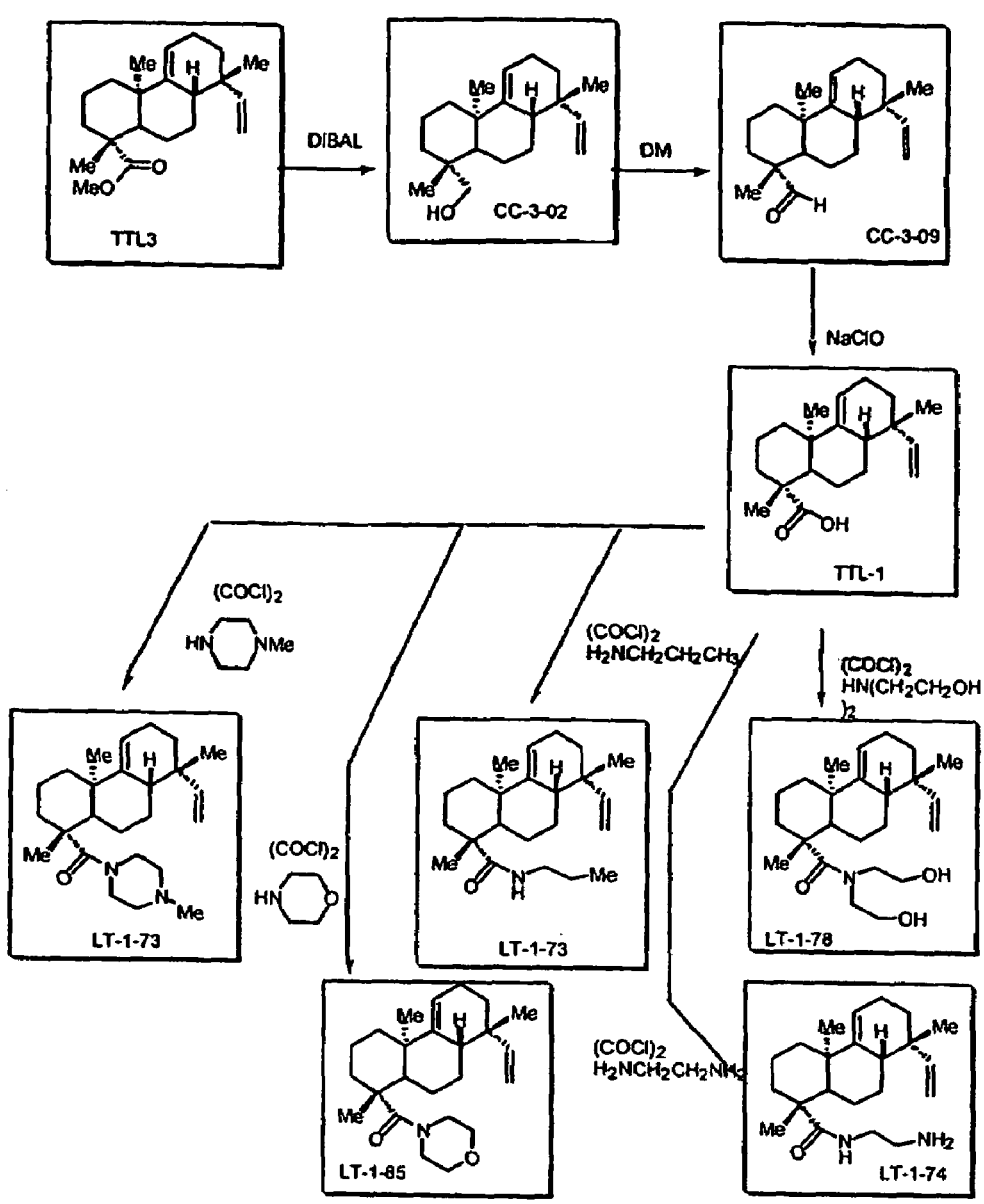
FIG. 30 depicts a strategy (Strategy 1) of the synthesis of TTL3 analogs, CC-3-02, CC-3-09, TTL-1, LT-1-73, LT-1-78, LT-1-85, and LT-1-74.

The compounds herein designated as CC-3-02, CC-3-09, TTL-1, LT-1-73, LT-1-73, LT-1-78, LT-1-85, and LT-1-74 were synthesized by following the strategy as depicted in FIG. 30.

B. Strategy 2

Figure 31:
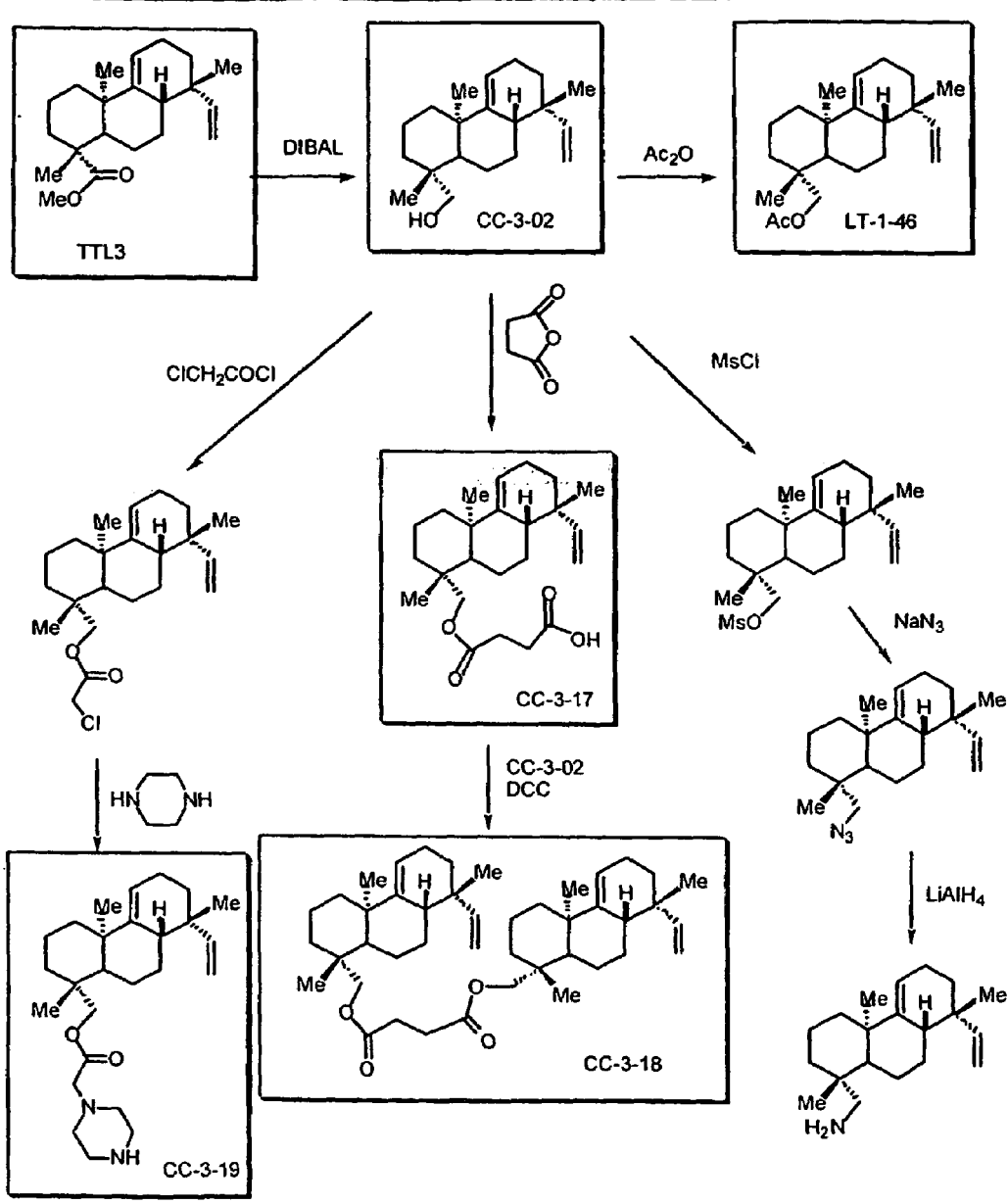
FIG. 31 depicts a strategy (Strategy 2) of the synthesis of TTL3 analogs, CC-3-02, LT-1-46, CC-3-19, CC-3-17, and CC-3-18.

The compounds herein designated as CC-3-02, LT-1-46, CC-3-19, CC-3-17, and CC-3-18 were synthesized by following the strategy as depicted in FIG. 31.

C. Strategy 3

Figure 32:
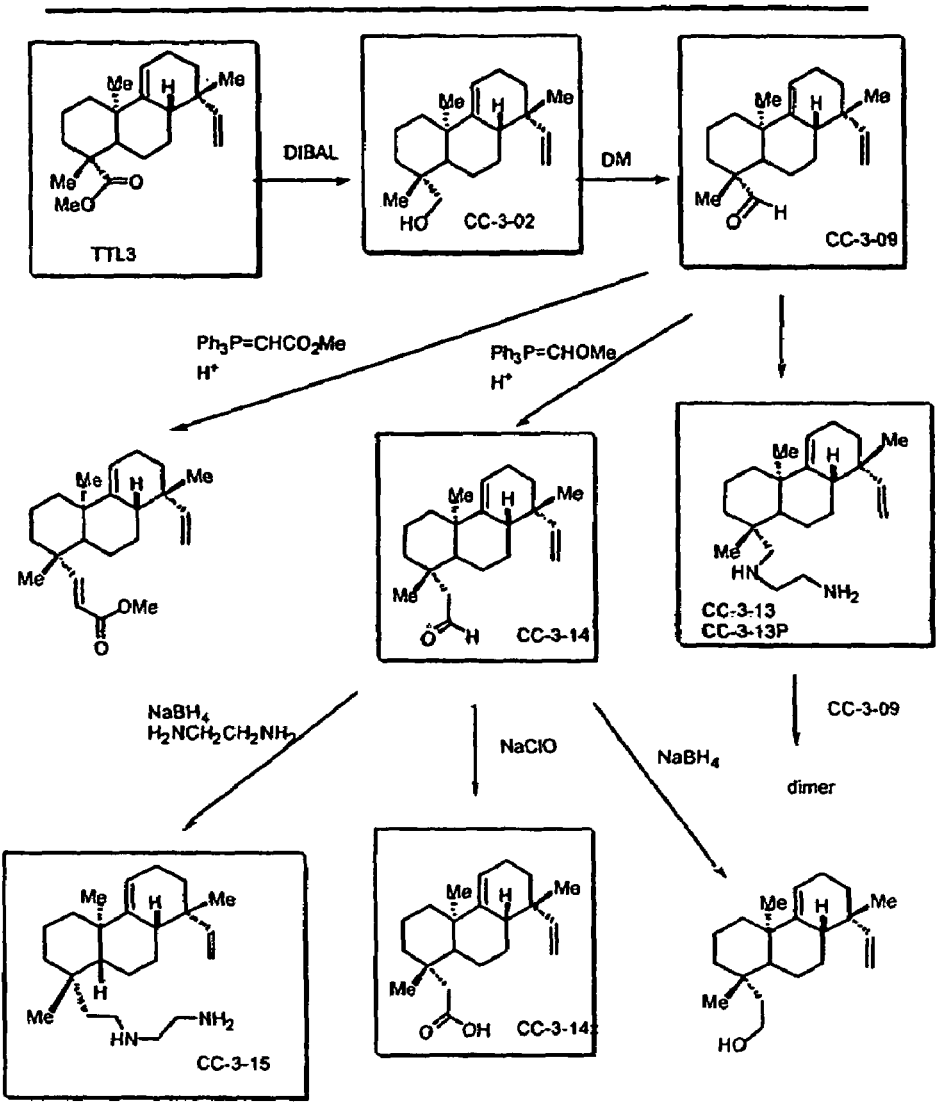
FIG. 32 depicts a strategy (Strategy 3) of the synthesis of TTL3 analogs, CC-3-02, CC-3-09, CC-3-14. CC-3-13, CC-3-13P, CC-3-15, and CC-3-14x.
Figure 35:
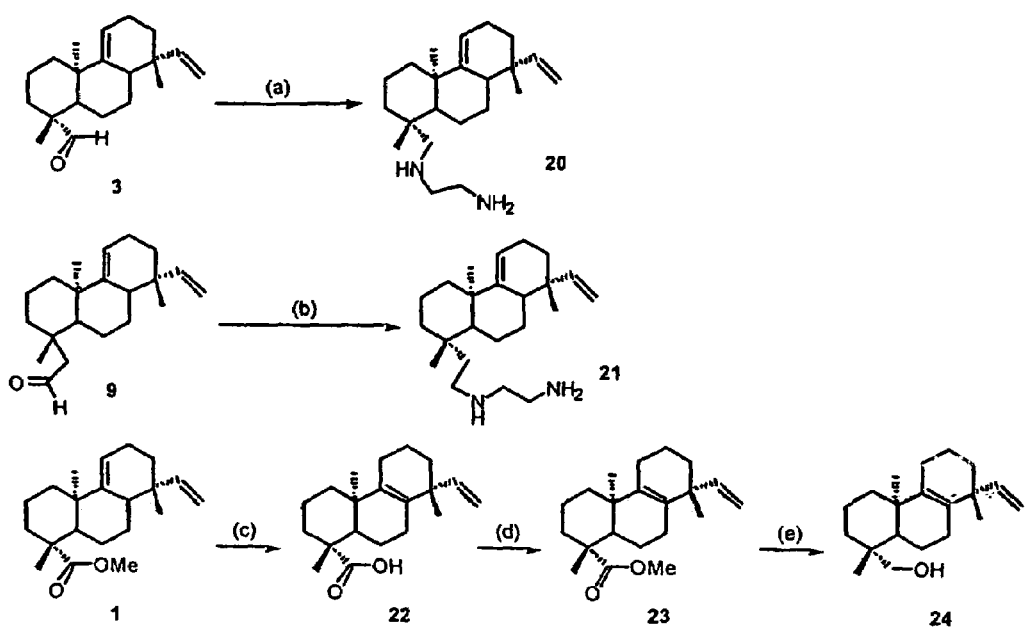
FIG. 35 depicts a schematic synthetic scheme (Scheme 3) of the synthesis of TTL3 analogs and certain compounds of the invention.
Figure 36:
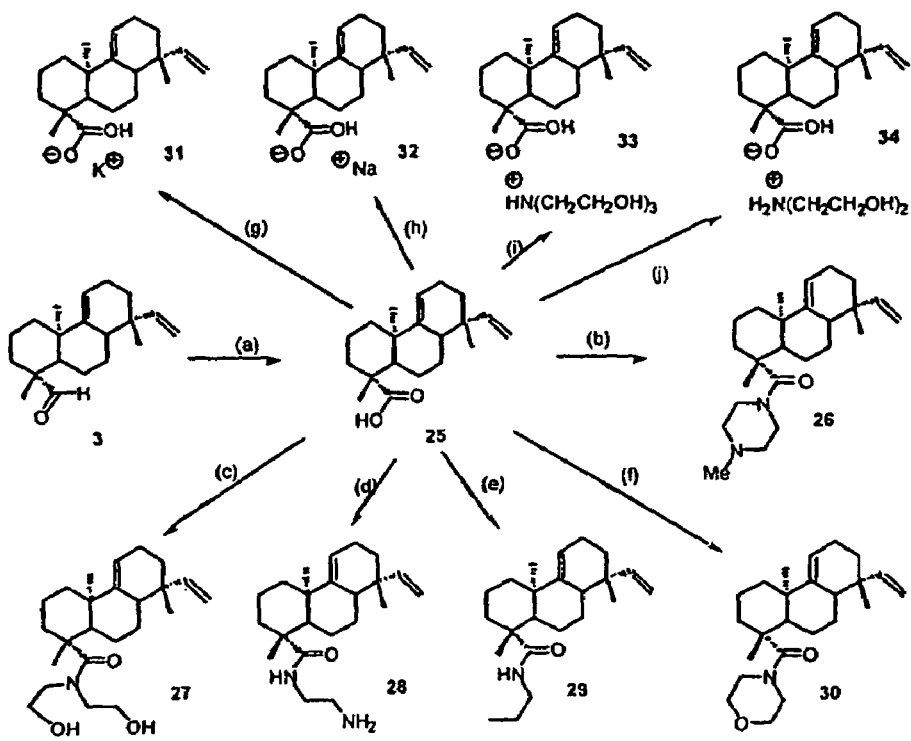
FIG. 36 depicts a schematic synthetic scheme (Scheme 4) of the synthesis of TTL3 analogs and certain compounds of the invention.
Figure 37:
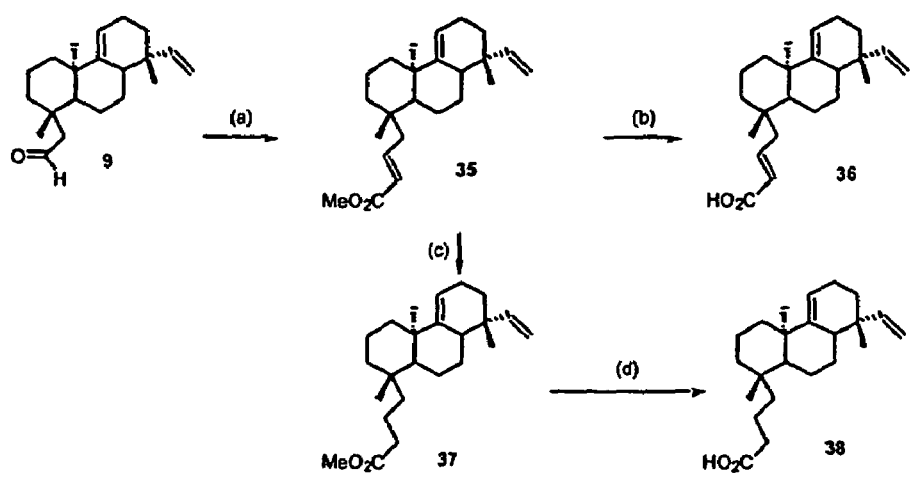
FIG. 37 depicts a schematic synthetic scheme (Scheme 5) of the synthesis of TTL3 analogs and certain compounds of the invention.

The compounds herein designated as CC-3-02, CC-3-09, CC-3-14, CC-3-13, CC-3-13P, CC-3-15, and CC-3-14x were synthesized by following the strategy as depicted in FIG. 32.

Example 23

Scheme for Synthesis of TTL3 Analogs

The synthesis of TTL3 analogs are demonstrated in FIGS. 33–37 and further detailed with the following descriptions:

Compound 1 (TTL3): colorless oil; $R_f$=0.75 (silica, 25% ether in hexanes); $^1$H NMR (400 MHz, $CDCl_3$) δ 5.96 (dd, 1H, J=16.8, 11.6 Hz), 5.50 (m, 1H), 4.98 (m, 2H), 3.62 (s, 3H), 2.20–2.11 (m, 1H), 2.10–1.91 (m, 4H), 1.90–1.70 (m, 4H), 1.69–1.51 (m, 3H), 1.50–1.38 (m, 3H), 1.36–1.24 (m, 1H), 1.17 (s, 3H), 1.04 (s, 3H), 0.90 (s, 3H); $^{13}$C NMR (100 MHz, $CDCl_3$) δ 177.9, 149.1, 143.8, 117.9, 111.7, 51.2, 47.7, 44.4, 41.4, 41.2, 38.9, 38.3, 37.7, 34.8, 30.4, 28.4, 24.8, 23.1, 22.3, 22.2, 20.6, 19.8.

Compound 2: To a well stirred solution of ester 1 (480 mg, 1.50 mmol) in $CH_2Cl_2$ (10 ml) was treated with DIBAL (6.0 mmol, 6.0 ml, 1M in $CH_2Cl_2$) at −78° C. After stirring for 30 min, the whole reaction mixture was allowed to warm up to rt for another 2 h. Methanol (5 ml) was added to quench the reaction mixture and the whole reaction mixture was diluted with ether (30 ml) and Rochelle salt (20 ml, 1N water solution). After stirring vigorously another 2 h at rt, the organic layer was extracted with ether (3×40 ml) and concentrated. The brown residue was purified through flash chromatography over silica gel using 20% ether in hexane as eluant to afford the desired product 2 (372 mg, 86%). White solid, $[α]^D$=+70 (c=1, benzene). $^1$H NMR ($CDCl_3$, 400 MHz) δ 5.95 (dd, J=11.2 Hz, J=12 Hz, 1H), 5.46 (m, 1H), 4.98 (t, J=8 HZ, 2H), 3.82 (d, J=12 Hz, 1H), 3.52 (d, J=12 Hz, 1H), 2.07–1.57 (m, 6H), 1.51–1.42 (m, 5H), 1.27–1.23 (m, 6H), 1.05 (s, 3H), 1.02 (s, 3H), 0.95 (s, 3H); $^{13}$C NMR ($CDCl_3$, 100 MHz) δ 150.39, 142.47, 117.05, 112.34, 64.85, 45.74, 42.11, 41.10, 38.46, 37.46, 35.36, 29.78, 26.32, 26.02, 24.95, 23.36, 19.14, 18.49; HRMS calcd. for $C_{20}H_{32}O$: 288.24; Found 288 (GC-MS).

Compound 3: To a well stirred solution of alcohol 2 (360 mg, 1.23 mmol) in $CH_2Cl_2$, was added portionwise Dess-Martin reagent (483 mg, 1.61 mmol) and the mixture was allowed to stir for 3 h at rt until tlc indicated complete consumption of starting material. The whole reaction mixture was extracted with $CH_2Cl_2$ (3×50 ml), washed with $NaHCO_3$ and concentrated. The brown residue was purified through silica gel chromatography over silica gel using 15% ether in hexane (v/v) as eluent to afford the desired product 3 (266 mg, 74%). 3: White solid, $[α]^D$=−142.2 (c=1, benzene). $^1$H-NMR ($CDCl_3$, 400 MHz) δ 9.94 (s, 1H), 5.94 (dd, J=11.6 Hz, J=12 Hz, 1H), 5.53 (m, 1H), 4.96 (t, J=8 Hz, 2H), 2.10–2.03 (m, 4H), 1.95–1.86 (m, 3H), 1.71–1.42 (m, 7H), 1.28–1.23 (m, 2H), 1.07 (s, 3H), 1.02 (s, 3H), 0.96 (s, 3H); $^{13}$C-NMR($CDCl_3$, 100 MHz) δ 206.39, 148.13, 142.42, 118.10, 112.39, 48.22, 46.55, 41.80, 40.67, 37.70, 36.70, 35.05, 24.96, 24.47, 23.92, 23.27, 20.54, 19.64, 18.47 HRMS calcd. for $C_{20}H_{30}O$: 309.21 (M+Na)$^+$ found 309 (ESI Mass Spec).

Ethyl Ester 4: To a well stirred solution of NaH (67 mg, 0.43 mmol) in THF (20 ml) at 0° C. was added triethyl phosphonoacetate (500 mg, 0.60 mmol). The reaction mixture was allowed to attend rt over a period of 4 h and treated with a solution (THF, 10 ml) of aldehyde 3 (76 mg, 0.27 mmol) and then the reaction mixture was heated under reflux for 16 h. After quenching with water, the organic layer was extracted with ether (2×60 ml). The ether extract was concentrated and purified over silica gel (5% ether/hexane, v/v) to afford the desired ester 4 (68 mg, 70%). 4: Oil ($R_f$=0.4, 10% ether/hexane, v/v), $^1$H-NMR($CDCl_3$, 400 MHz) δ 7.34 (d, J=16 Hz, 1H), 5.90 (dd, J=11.6 Hz, J=12 Hz, 1H), 5.76 (d, J=16 Hz, 1H), 5.48 (m, 1H), 4.97 (m, 2H), 4.18 (q, J=8 Hz, 2H), 2.09–1.74 (m, 6H), 1.66–1.42 (m, 8H), 1.30–1.17 (m, 5H), 1.06 (s, 3H), 0.98 (s, 3H), 0.95 (s, 3H); $^{13}$C-NMR($CDCl_3$, 100 MHz) δ 167.10, 154.47, 149.15, 142.41, 118.13, 117.43, 112.33, 60.18, 46.75, 42.38, 41.07, 39.93, 38.66, 37.74, 37.03, 29.67, 25.04, 24.81, 23.35, 20.19, 19.11, 14.45; HRMS calcd. for $C_{24}H_{36}O_2$ 356.54 Found 356.54.

Methyl Ester 5: To a well stirred solution of ester 4 (60 mg, 0.168 mmol) in methanol (10 ml), magnesium powder (50 mg, 6.25 mmol) was added and the whole reaction mixture was stirred at room temp. for 12 h. HCl (10 ml, 2M)

was added to the reaction mixture to dissolve the remaining magnesium. The reaction mixture was concentrated under reduced pressure and extracted with ether (2×50 ml) and the organic layer concentrated. The desired product 5 was purified through column chromatography using 10% ether/hexane (v/v) as eluent. 5: Oil (50 mg, 87% yield); $^1$H-NMR (CDCl$_3$, 400 MHz) δ 5.95(dd, J=11.2 Hz, J=12 Hz, 1H), 5.45 (m, 1H), 4.98 (m, 2H), 3.66 (s, 3H), 3.26–1.87 (m, 7H), 1.69–1.51(m,11H), 1.24–1.19 (m, 2H), 1.09 (s, 3H), 1.04 (s, 3H), 0.93 (s, 3H); HRMS Calcd. for C$_{23}$H$_{36}$O$_2$ 344.56; Found 344.56.

Acid 6: Ester 5 (50 mg, 0.14 mmol) was dissolved in a mixed solution of THF/H$_2$O (v/v, 1:1, 4 ml) and LiOH (30 mg) was added. After stirring for 30 min the reaction mixture was heated under reflux for 12 hours. The reaction mixture was diluted with water, acidified with HCl solution (3 N) and extracted with ether (2×50 ml). The desired product 6 was purified through column chromatography over silica gel using 50% ether/hexane (v/v). 6: White solid (34 mg, 71%); $^1$H-NMR (CDCl$_3$, 400 MHz) δ 5.95 (dd, J=11.2 Hz, J=12 Hz, 1H), 5.46 (m, 1H), 5.00–4.95 (m, 2H), 2.27–2.17 (m, 3H), 2.09–1.88 (m, 10H), 1.69–1.37 (m, 7H), 1.24–1.18 (m, 1H), 1.09 (s, 3H), 1.04 (s, 3H), 0.83 (s, 3H); $^1$C-NMR(CDCl$_3$, 100 MHz) δ 178.62, 152.06, 143.69, 118.13, 113.52, 67.09, 48.16, 43.67, 42.52, 39.42, 38.38, 36.98, 31.02, 30.45, 29.48, 28.43, 27.33, 26.26, 24.64, 21.17, 20.41, 19.86, 16.62; HRMS Calcd. for C$_{22}$H$_{34}$O$_2$ 329.24 (M–H)$^+$, found 329.20.

Unsaturated Acid 7: To a solution of methyl ester 4 (60 mg, 0.17 mmol) in THF/H$_2$O (1:1, v/v, 8 ml), LiOH (40 mg, excess) was added at rt. After stirring for 30 min the reaction mixture was allowed to reflux for 12 h. The reaction mixture was diluted with water and acidified with HCl solution (3 N, 40 ml) and extracted with ether (2×50 ml). The desired product was purified through column chromatography over silica gel using ether/hexane (1:1, v/v). 7: White solid (42 mg, 76%), $^1$H NMR (CDCl$_3$, 400 MHz) δ 7.45 (d, J=16 Hz, 1H), 5.94 (dd, J=11.2 Hz, J=12 Hz, 1H), 5.76 (d, J=16 Hz, 1H), 5.48 (m, 1H), 5.00–4.95 (m, 2H), 2.15–1.74 (m, 5H), 1.64–1.50 (m, 7H), 1.47–1.42 (m, 5H), 1.06 (s, 3H), 0.99 (s, 3H), 0.95 (s, 3H); $^{13}$C NMR(CDCl$_3$, 100 MHz) δ 171.03, 157.41, 149.02, 142.37, 117.55, 117.20, 112.37, 46.82, 42.36, 41.01, 40.18, 38.50, 38.21, 37.75, 37.01, 29.82, 25.04, 24.75, 23.35, 20.18, 19.11; HRMS Calcd for C$_{22}$H$_{32}$O$_2$ 351 (M+Na)$^+$ Found 351 (ESI Mass Spec.).

Vinyl ether 8: Methoxy methyl triphenyl phosphonium chloride was stirred in THF (476.1 mg, 1.39 mmol) and treated with 4.8 equivalent of potassium t-butoxide, followed by addition of aldehyde 3 (80 mg, 0.28 mmol). The reaction was completed within 30 minutes. After the reaction mixture was concentrated, the residue was redissolved in ethyl ether and extracted with NaCl solution. After the chromatography column purification, 87 mg of the product was obtained (99% yield).

Aldehyde 9: To a well stirred solution of compound 8 (50 mg, 0.159 mmol) in acetone (10 ml), was added p-toluene sulphonic acid (50 mg, 0.26 mmol) and the reaction was allowed to stir for 2 h at rt. TLC indicated the complete formation of desired product. Solvent was removed and the reaction mixture was extracted with ether (3×40 ml) and washed with sat. NaHCO$_3$ and sat. NaCl solution. The crude product was purified through column chromatography using 4% ether hexane as eluent. 9: Oil (88%), [α]$^D$=+4.4 (c=1, benzene), $^1$H-NMR (CDCl$_3$, 400 MHz) δ 5.94 (dd, J=11.2 Hz, J=12 Hz, 1H), 5.48 (m, 1H), 5.01–4.96 (m, 2H), 2.55 (d, J=12 Hz, 1H), 2.37 (d, J=12 Hz, 1H), 2.09–1.93 (m, 3H), 1.76–1.71 (m, 2H), 1.63–1.13 (m, 12H), 1.09 (s, 3H), 1.07 (s, 3H), 1.06 (s, 3H); $^{13}$C-NMR(CDCl$_3$, 100 MHz) δ 204.26, 150.23, 142.24, 117.26, 112.46, 47.22, 42.43, 40.81, 39.02, 38.08, 37.03, 29.06, 25.59, 25.00, 23.39, 19.90, 19.07; HRMS calcd for C$_{21}$H$_{32}$O 323.25 Found 323.23.

Acid 10: To a solution of 17 mg of aldehyde 10 (0.056 mmol) in tBuOH/H$_2$O (3:1) was added 23.3 mg of NaH$_2$PO$_4$.H$_2$O (0.17 mmol) and the reaction mixture was stirred to completely dissolve the salt before adding 84.5 μl of 2M 1-methyl-2-butene in THF. The reaction was stirred for 30 minutes, then it was treated with 15.3 mg of NaClO$_2$ (0.17 mmol). When the reaction was done, it was neutralized with NH$_4$Cl. The product was collected via the extraction with CH$_2$Cl$_2$ and purified through chromatography column to produce 17.0 mg of acid 10 (96%). 10: $^1$H-NMR (CDCl3, 300 MHz) δ 6.00–5.90 (m, 1H), 5.48 (d, J=3 Hz, 1H), 5.02–4.95 (m, 2H), 2.58 (d, J=12.6 Hz, 1H), 2.30 (d, J=12.6 Hz, 1H), 1.25 (s, 3H), 1.07 (s, 3H), 1.02 (s, 3H).

Acid 12: To a well stirred solution of alcohol 2 (70 mg, 0.24 mmol) in DCM (8 ml), DMAP (5 mg, cat.) and succinic anhydride (30 mg, 0.28 mmol) were added and the reaction mixture was allowed to stir for 8 h at rt. The reaction mixture was extracted with DCM (2×40 ml) and washed with water (30 ml). The desired product was purified through column chromatography over silica gel using 12–16% ether in hexane to afford acid 12. 12: Solid (73 mg, 78%). IR (neat) 3312 2920, 1732, 1708 cm$^{-1}$; $^1$H-NMR (CDCl$_3$, 400 MHz) δ 5.95 (dd, J=11.2 Hz, 12 Hz, 1H), 5.48 (m, 1H), 5.0–4.96 (m, 2H), 4.34 (d, J=12 Hz, 1H), 4.03 (d, J=12 Hz, 1H), 2.70–2.61 (m, 4H), 2.09–1.91 (m, 4H), 1.80–1.39 (m, 10H), 1.25–1.08 (m, 6H), 1.05 (s, 3H), 0.91 (s, 3H); $^{13}$C-NMR (CDCl$_3$, 100 MHz) δ 177.32, 172.02, 150.09, 142.32, 117.24, 112.41, 67.12, 45.88, 42.19, 40.99, 37.97, 37.21, 36.11, 29.80, 29.01, 26.77, 25.97, 25.00, 23.39, 19.94, 19.10, 18.78; HRMS Calcd for C$_{24}$H$_{36}$O$_4$ 411.25 (M+Na)$^+$ Found 411.25.

Acid 11: This compound was prepared using the procedure described above for acid 12. In this case maleic anhydride was used instead of succinic anhydride. 11: (68 mg, 71%); $^1$H-NMR (CDCl$_3$, 500 MHz) δ 6.01 (dd, J=11.2 Hz, J=12 Hz, 1H), 5.46 (brd, 1H), 5.09–4.95 (m, 2H), 4.36 (d, J=8 Hz, 1H), 4.02 (d, J=8 Hz, 1H), 2.48–2.36 (m, 3H), 2.16–1.92 (m, 5H), 1.86–1.38 (m, 9H), 1.35–1.11 (m, 10H), 0.98–0.81 (m, 5H); $^{13}$C-NMR(CDCl$_3$, 100 MHz) δ 173.96, 169.08, 146.28, 138.46, 113.29, 108.44, 93.15, 88.18, 62.60, 41.65, 37.95, 36.75, 33.71, 32.93, 29.11, 28.66, 25.54, 25.46, 25.43, 22.54, 20.69, 19.06, 15.61, 14.45; HRMS Calcd for C$_{25}$H$_{38}$O$_4$ 425.26 Found 425.26.

Ester 13: To a well stirred solution of alcohol 2 (22 mg, 0.079 mmol) and acid 12 (24 mg, 0.0617 mmol) in DCM (10 ml), was added DCC (17 mg, 0.080 mmol) and DMAP (5 mg, cat.) and the reaction mixture was allowed to stir at rt for 12 h. The mixture was extracted with DCM (20×2 ml) and washed with water (15 ml). The desired product was isolated through silica gel chromatography. 13: Solid (30 mg, 70%); $^1$H-NMR(CDCl$_3$, 400 MHz) δ 5.95 (dd, J=11.2 Hz, J=12 Hz, 2H), 5.48 (m, 2H), 5.00–4.95 (m, 4H), 4.32 (d, J=12 Hz, 2H), 4.03 (d, J=12 Hz, 2H), 2.62 (s, 4H), 2.05–1.70 (m, 6H), 1.76–1.70 (m, 3H), 1.56–1.42 (m, 23 H), 1.20 (s, 6H), 0.98 (s, 6H), 0.93 (s, 6H); $^{13}$C-NMR(CDCl$_3$, 100 MHz) δ 172.18, 150.10, 142.32, 117.23, 112.41, 66.95, 45.87, 42.18, 40.99, 37.97, 37.19, 36.13, 29.40, 26.82, 25.98, 25.00, 23.39, 19.95, 19.13, 18.77; HRMS Calcd for C$_{44}$H$_{66}$O$_4$ 681.48 (M+Na)$^+$ Found 681.48.

Chloro Acetyl Derivative 14: To a well stirred solution of alcohol 2 (40 mg, 0.1389 mmol) and DMAP (10 mg, cat.) in DCM (10 ml) at 0° C., was added chloroacetyl chloride (23 mg, 0.20 mmol). The reaction mixture was allowed to stir at rt for another 2 h and then quenched with water and extracted with ether (2×40 ml). The combined ether layer was concentrated and purified through column chromatography. The desired product was eluted with 8% ether/hexane. 14: Solid (39 mg, 82%). $^1$H-NMR(CDCl$_3$, 400 MHz) δ 5.93(dd, J=1.2 Hz, J=13 Hz, 1H), 5.48 (brd, 1H), 5.01–4.96 (m, 2H), 4.43(d, J=8 Hz, 1H), 4.13(d, J=8 Hz, 1H), 4.06 (s, 2H), 2.09–1.96 (m, 3H), 1.92–1.71(m, 2H), 1.65–1.42 (m, 14H), 1.22 (s, 3H), 1.14 (s, 3H) 0.97 (s, 3H); $^{13}$C-NMR(CDCl$_3$, 100 MHz) δ 167.28, 149.96, 142.26, 117.37, 112.47, 68.58, 45.91, 42.19, 41.06, 40.93, 37.95, 37.70, 37.37, 36.04, 29.80, 26.69, 25.95, 25.01, 23.39, 19.94, 19.09, 18.82.

Morpholine Derivative 15: To a well stirred solution chloro acvetyl derivative 14 (24 mg, 0.066 mmol) in DCM, was added morpholine (15 mg, 0.17 mmol). The reaction mixture was heated under reflux for 12 h and the reaction mixture was extracted with DCM (2×30 ml) and washed with water (15 ml). The desired product was purified through column chromatography over silica gel. 15: Oil (20 mg, 71%); $^1$H-NMR(CDCl$_3$, 400 MHz) δ 5.94 (dd, J=11.2 Hz, J=12 Hz, 1H), 5.47 (m, 1H), 5.00–4.95 (m, 2H), 4.36 (d, J=12 Hz, 1H), 4.05 (d, J=12 Hz, 1H), 3.75–3.73 (m, 4H), 3.20 (s, 2H), 2.58–2.56 (m, 4H), 2.08–1.42 (m, 16H), 1.24 (s, 3H), 1.05 (s, 3H), 0.92 (s, 3H); $^{13}$C-NMR(CDCl$_3$, 100 MHz) δ 170.15, 150.02, 142.27, 117.28, 112.43, 81.54, 66.82, 59.62, 53.32, 52.0, 45.87, 42.17, 37.96, 37.67, 37.18, 29.78, 26.89, 25.95, 24.99, 19.93, 19.10, 18.79; HRMS Calcd. for C$_{26}$H$_{41}$NO$_3$ 416.31 (M+H)$^+$ Found 416.31.

Piperazine Derivative 16: Compound 16 was prepared according to the procedure described above, using piperazine insead of morpholine. 16: Oil (77%), $^1$H-NMR (CDCl$_3$, 400 MHz) δ 5.93 (dd, J=11.2 Hz, J=12 Hz, 1H), 5.48 (brd, 1H), 5.00–4.95 (m. 2H), 4.37 (d, J=10 Hz, 1H), 4.05 (d, J=10 Hz, 1H), 3.20 (s, 2H), 2.63 (brd, 2H), 2.60–2.57 (m, 5H), 2.4–2.2 (brd, 3H), 2.08–1.94 (m, 5H), 1.71–1.42 (m, 10H), 1.20 (s, 3H), 1.05 (s, 3H), 0.87 (s, 3H); $^{13}$C-NMR(CDCl$_3$, 100 MHz) δ 170.90, 150.28, 117.21, 112.39, 66.71, 59.78, 53.75, 53.47, 51.58, 51.25, 45.84, 42.15, 40.94, 37.93, 37.66, 37.17, 36.16, 29.78, 26.88, 25.95, 24.96, 23.25, 19.92, 19.10, 18.76; HRMS Calcd. for C$_{26}$H$_{42}$N$_2$O$_2$ 415.33 (M+H)$^+$, Found 415.33.

Compound 17: To a well stirred solution of product 16 (30 mg, 0.072 mmol) in DCM, was added triethyl amine (0.4 ml) and tosyl chloride (19 mg, 0.1 mmol). The reaction mixture was allowed to stir at rt for 15 h and was then quenched with water and extracted with methylene chloride (3×30 ml). The desired product was purified over silica gel using 25–30% ether/hexane as eluent. 17: White solid (40 mg, 69%); $^1$H-NMR (CDCl$_3$, 400 MHz) δ 7.62 (d, J=8 Hz, 2H), 7.31 (d, J=8 Hz, 2H), 5.92 (dd, J=11.2 Hz, 12 Hz, 1H), 5.47 (m, 1H), 5.0–4.95 (m, 2H), 4.36 (d, J=12 Hz, 1H), 4.03 (d, J=12 Hz, 1H), 3.24 (brd, 1H), 3.08 (brd, 4H), 2.72 (brd, 3H), 2.44 (s, 3H), 2.42–1.90 (m, 4H), 1.63–1.40 (m, 10H), 1.24–1.05 (m, 4H), 1.05 (s, 3H), 1.03 (s, 3H), 0.89 (s, 3H); $^{13}$C-NMR (CDCl$_3$, 100 MHz) δ 194.25, 149.93, 142.28, 131.92, 129.56, 127.72, 117.32, 112.45, 55.87, 51.90, 45.50, 42.15, 40.89, 37.93, 37.68, 36.15, 29.80, 26.85, 25.94, 24.98, 23.37, 19.92, 19.08, 18.79. HRMS Calcd for C$_{33}$H$_{48}$N$_2$O$_4$S 591.32 Found 591.32.

Ester 18: A solution of alchohol 2 (20 mg, 0.069 mmol) and 4-methyl morpholine (20 mg, 0.173 mmol) in methylene chloride (10 ml) was cooled to 0° C. and treated with ethyl propiolate (10 mg, 0.10 mmol). The whole reaction mixture was allowed to stir for overnight. Water (25 ml) was added in the reaction mixture and extracted with methylene chloride (2×30 ml). The combined organic extracts were combined and concentrated. Finally the desire product was purified through silica gel chromatography using 20% ether/hexane (v/v) as eluent. Oil (18 mg, 64%), $^1$H-NMR(CDCl$_3$, 400 MHz) δ 7.61 (d, J=12 Hz, 1H), 5.93 (dd, J=11.2 Hz, J=13 Hz, 1H), 5.48 (brd, 1H), 5.16 (d, J=13 Hz, 1H), 5.02–4.96 (m, 2H), 4.13 (q, J=8 Hz, 2H), 3.99 (d, J=8 Hz, 1H), 3.69 (d, J=8 Hz, 1H), 2.09–1.78 (m, 6H), 1.62–1.40 (m, 15H), 1.06 (s, 3H), 1.04 (s, 3H), 0.97 (s, 3H); $^1$C-NMR (CDCl$_3$, 100 MHz) δ 167.80, 163.03, 149.96, 142.25, 117.39, 112.46, 95.71, 73.70, 59.72, 45.76, 42.15, 40.90, 37.94, 37.60, 35.87, 26.70, 25.96, 24.98, 23.37, 19.93, 19.09, 18.79, 14.52.

Acetate 19: 8.7 mg of alcohol 2 was dissolved in 0.5 ml CH$_2$Cl$_2$, and treated with 5 equiv of pyridine, and 2.5 equiv of acetic anhydride. The reaction was stirred at room temperature for two hours and was then quenched with NaHCO$_3$/H$_2$O and extracted with ether. After chromatography column, 8.3 mg of pure product 19 was obtained (84%). 19: $^1$H-NMR (CDCl$_3$, 400 MHz) δ 5.95 (q, J=11.6 Hz, 1H), 5.48 (d, J=4.4 Hz, 1H), 5.01–4.96 (m, 2H), 4.29 (d, J=11.2 Hz, 1H), 4.01 (d, J=10.8 Hz, 1H), 2.05 (s, 3H), 1.25 (s, 3H), 1.06 (s, 3H), 0.94 (s, 3H); $^{13}$C-NMR (CDCl$_3$, 100 MHz) δ 18.77, 19.14, 19.95, 21.17, 23.39, 25.00, 25.99, 26.83, 29.81, 36.14, 37.11, 37.22, 37.70, 41.01, 42.20, 45.86, 66.67, 112.42, 117.23, 142.36, 150.15, 171.22.

Amine 20: A solution of aldehyde 3 (40 mg, 0.14 mmol) in dry MeOH (12 ml) was treated with ethylene diamine (0.4 ml, 3.36 mmol) at rt. The reaction mixture was allowed to stir at rt for 4 h until tlc confirmed the disappearance of starting material. The mixture was then cooled to 0° C. and NaBH$_4$ (11 mg, 0.28 mmol) was added portionwise. The reaction mixture again allowed to stir for overnight and it was then quenched with saturated ammonium chloride solution (25 ml). Extraction was made with methylene chloride (2×35 ml). The desired product was purified through silica gel column chromatography. 20: Oil (42 mg, 90%); IR (neat) 3382, 2924 cm$^{-1}$; $^1$H-NMR(CDCl$_3$, 400 MHz) δ 5.95 (dd, J=11.2 Hz, J=12 Hz, 1H), 5.45 (brd, 1H), 5.00–4.95 (m, 2H), 2.78–2.75 (m, 3H), 2.66–2.63 (m, 2H), 2.47 (d, J=11.6 Hz, 1H), 2.10–1.83 (m, 6H), 1.63–1.44 (m, 10H), 1.42 (s, 3H), 1.05 (s, 3H), 0.85 (s, 3H); $^3$C-NMR(CDCl$_3$, 100 MHz) δ 150.69, 142.47, 116.85, 112.24, 53.38, 51.68, 46.35, 42.24, 41.31, 38.14, 37.34, 37.24, 36.54, 30.38, 27.64, 26.18, 24.98, 23.38, 20.00, 19.33, 18.54; HRMS Calcd for C$_{22}$H$_{38}$N$_2$ 331.31 (M+H)$^+$, Found 331.31.

Amine 21: Amine 21 was synthesized according to the same procedure described above for amine 19, using aldehyde 9 as starting material. 21: $^1$H-NMR(CDCl$_3$, 400 MHz) δ 5.98 (dd, J=11.2 Hz, J=12 Hz, 1H), 5.45 (brd, 1H), 5.00–4.95 (m, 2H), 2.94 (brd, 1H), 2.80 (brd, 1H), 2.82–2.79 (m, 2H), 2.60–2.35 (brd, 4H), 2.09–1.90 (m, 6H), 1.67–1.42 (m, 7H), 1.24–1.17 (m, 5H), 1.24 (s, 3H), 1.10 (s, 3H), 0.85 (s, 3H); $^{13}$C-NMR(CDCl$_3$, 100 MHz) δ 150.82, 142.46, 125, 38, 116.89, 112.31, 51.47, 47.14, 45.82, 42.46, 41.28, 38.23, 37.73, 37.28, 35.65, 31.22, 30.41, 28.63, 26.11, 25.03, 23.43, 19.99, 19.36, 18.76; HRMS Calcd for C$_{23}$H$_{40}$N$_2$ 344.55 Found 344.31.

Compound 22. 150 mg of ester 1 (0.475 mmol) and 173 mg of LiBr were dissolved in DMF and heated at 165° C. for two days. The reaction was quenched with H$_2$O and the product extracted with ethyl ether and purified using chromatography column. The reaction yielded 74.6 mg of white crystal product 22 (52%). $^1$H-NMR (CDCl$_3$, 400 MHz) δ 5.60 (q, J=10.4 Hz, 1H), 4.98 (dd, J=8.4 Hz, 1H), 4.76 (dd, J=15.2 Hz, 1H), 1.26 (s, 3H), 1.05 (s, 3H), 0.93 (s, 3H); $α_D$=–144.06.

Compound 23: 10 mg of compound 22 (0.33 mmol) were dissolved in 2.5 ml of methanol, and treated with 2.5 ml of (trimethylsilyl) diazomethane, and 2.5 ml of benzene. The reaction was stirred at room temperature for 20 minutes, then worked up with $H_2O$, and extracted with ether. The mixture was purified by silica gel column purification to afford 8.2 mg of compound 23. 23: white solid (82% yield). $^1$H-NMR (CDCl$_3$, 300 MHz) δ 5.61 (q, J=10.2 Hz, 1H), 4.97 (dd, J=8.7 Hz, 1H), 4.76 (dd, J=15.3 Hz, 1H), 3.63 (s, 3H), 1.19 (s, 3H), 1.05 (s, 3H), 0.82 (s, 3H); $^{13}$C-NMR (CDCl$_3$, 100 MHz) δ 19.22, 20.22, 20.93, 22.20, 26.29, 27.44, 29.73, 30.00, 37.76, 38.86, 39.00, 40.25, 42.56, 45.13, 52.42, 54.81, 113.80, 131.17, 140.28, 147.83, 179.27; $α_D$=−121.6.

Compound 24: 7.8 mg of ester 23 (0.025 mmol) was dissolved in dry $CH_2Cl_2$ and treated at −78° C. with 4.0 equivalent DIBALH for 10 minutes. The reaction was quenched with Rochelle salt solution and the product was collected by extraction with ether and purified through chromatography column. 24: (6.5 mg, 94% yield). $^1$H-NMR (CDCl$_3$, 300 MHz) δ 5.62 (q, J=10.5 Hz, 1H), 4.96 (dd, J=8.4 Hz, 1H), 4.75 (dd, J=15.3 Hz, 1H), 3.78 (d, J=10.8 Hz, 1H), 3.48 (d, J=10.8 Hz, 1H), 1.25 (s, 3H), 1.04 (s, 3H), 0.99 (s, 3H); $^{13}$C-NMR (CDCl$_3$, 100 MHz) δ 14.15, 14.37, 14.75, 16.09, 20.27, 21.57, 22.09, 23.75, 30.75, 31.70, 32.97, 33.77, 34.03, 36.48, 61.10, 107.97, 124.66, 135.63, 142.29; $α_D$=−53.8.

Compound 25. 53.2 mg of aldehyde 3 (0.19 mmol) was dissolved in tBuOH/$H_2O$ (3:1), and treated with 76.45 mg of $NaH_2PO_4.H_2O$ (0.56 mmol). The reaction mixture was stirred to completely dissolve the salt before the addition of 277.5 µl of 2M 1-methyl-2-butene in THF. The reaction was stirred for 30 minutes, then it was treated with 50.2 mg of $NaClO_2$ (0.56 mmol). When the reaction was done, it was neutralized with $NH_4Cl$. The product was collected via the extraction with $CH_2Cl_2$ and purified through chromatography column to produce 44 mg of compound 25 (78%). 25: white solid; $R_f$=0.30 (silica, 30% ether in hexanes); $^1$H NMR (400 MHz, CDCl$_3$) δ 5.96 (dd, 1H, J=14.4, 9.6 Hz), 5.52 (m, 1H), 4.98–4.95 (m, 2H), 2.20–1.72 (m, 10H), 1.64–1.58 (m, 3H), 1.57–1.37 (m, 4H), 1.22 (s, 3H), 1.04 (s, 3H), 0.99 (s, 3H); $^{13}$C NMR (100 MHz, CDCl$_3$) δ 182.9, 149.3, 143.9, 118.1, 111.9, 47.5, 44.2, 41.3, 41.2, 38.9, 38.0, 37.6, 34.8, 28.4, 24.7, 23.0, 22.4, 21.9, 20.3, 19.5.

Compound 26. 3.5 mg of acid 25 (0.012 mmol) was dissolved in dry $CH_2Cl_2$ and treated with 10 equivalents of $(COCl)_2$ followed by two drops of DMF. When the reaction stopped bubbling, the $CH_2Cl_2$ solvent and excess $(COCl)_2$ were evaporated under vacuum and the reaction residue was redissolved in dry benzene and then treated with 5 equivalent of N-methyl piperazine. When the reaction was done, the solvent was evaporated under vacuum, and the product was collected by the extraction with ether and $NH_4Cl$ solution. After the chromatography column, 3.0 mg of pure product 26 was obtained (65% yield). 26: $^1$H-NMR (CDCl$_3$, 300 MHz) δ 5.95 (q, J=11.6 Hz, 1H), 5.46 (d, J=2.4 Hz, 1H), 5.00–4.94 (m, 2H), 3.73–3.68 (m, 4H), 2.48 (s, 3H), 2.10–2.03 (m, 4H), 1.25 (s, 3H), 1.09 (s, 3H), 1.03 (s, 3H); $α_D$=+8.6.

Compound 27. 10 mg of acid 25 (0.033 mmol) was dissolved in dry $CH_2Cl_2$ and treated with 10 equivalents of $(COCl)_2$ followed by two drops of DMF. When the reaction stopped bubbling, the $CH_2Cl_2$ solvent and excess $(COCl)_2$ were evaporated under vacuum and the reaction residue was redissolved in dry benzene and then treated with 5 equivalent of diethanolamine. When the reaction was done, the solvent was evaporated under vacuum, and the product was collected by the extraction with ether and $NH_4Cl$ solution. After the chromatography column, 9.2 mg of pure product was obtained (75% yield). $^1$H-NMR (CDCl$_3$, 300 MHz) δ 5.95 (q, J=11.6 Hz, 1H), 5.46 (s, 1H), 4.96 (m, 2H), 2.99 (s, 7H), 2.37 (d, 1H), 1.29 (s, 3H), 1.09 (s, 3H), 1.02 (s, 3H); $α_D$=−41.2.

Amine 28: 5.0 mg of acid 25 (0.017 mmol) was dissolved in dry $CH_2Cl_2$ and treated with 10 equivalents of $(COCl)_2$ followed by two drops of DMF. When the reaction stopped bubbling, the $CH_2Cl_2$ solvent and excess $(COCl)_2$ were evaporated under vacuum and the reaction residue was redissolved in dry benzene and then treated with 5 equivalent of ethylene diamine. When the reaction was done, the solvent was evaporated under vacuum, and the product was collected by the extraction with ether and $NH_4Cl$ solution. After the chromatography column, 3.0 mg of pure product was obtained (52% yield).

Compound 29. 5.0 mg of acid 25 (0.017 mmol) was dissolved in dry $CH_2Cl_2$ and treated with 10 equivalents of $(COCl)_2$ followed by two drops of DMF. When the reaction stopped bubbling, the $CH_2Cl_2$ solvent and excess $(COCl)_2$ were evaporated under vacuum and the reaction residue was redissolved in dry benzene and then treated with 5 equivalent of propylamine. When the reaction was done, the solvent was evaporated under vacuum, and the product was collected by the extraction with ether and $NH_4Cl$ solution. After the chromatography column, 3.7 mg of pure product was obtained (63% yield).

Compound 30. 4.5 mg of acid 25 (0.015 mmol) was dissolved in dry $CH_2Cl_2$ and treated with 10 equivalents of $(COCl)_2$ followed by two drops of DMF. When the reaction stopped bubbling, the $CH_2Cl_2$ solvent and excess $(COCl)_2$ were evaporated under vacuum and the reaction residue was redissolved in dry benzene and then treated with 5 equivalent of morpholine. When the reaction was done, the solvent was evaporated under vacuum, and the product was collected by the extraction with ether and $NH_4Cl$ solution. After the chromatography column, 5.0 mg of pure product was obtained (89% yield). $^1$H-NMR (CDCl$_3$, 400 MHz) δ 5.95 (q, J=11.6 Hz, 1H), 5.47 (s, 1H), 4.99–4.95 (m, 2H), 3.64–3.60 (m, 8H), 1.29 (s, 3H), 1.11 (s, 3H), 1.03 (s, 3H); $^{13}$C-NMR (CDCl$_3$, 100 MHz) δ 21.24, 22.82, 23.22, 24.90, 25.16, 27.35, 34.36, 37.65, 39.71, 40.37, 41.42, 41.62, 46.32, 46.47, 46.71, 51.29, 67.02, 111.68, 117.10, 143.89, 149.84; $α_D$=−47.1.

Compound 31. To a solution of 14.5 mg of acid 25 (0.048 mmol) in THF was added 1 equivalent of KOH dissolved in 200 µl of water and the mixture was stirred for 1 h. Evaporation of the solvent afforded pure salt 31 (100%).

Compound 31. To a solution of 24.5 mg of acid 25 (0.072 mmol) in THF was added 1 equivalent of NaOHOH dissolved in 200 µl of water and the mixture was stirred for 1 h. Evaporation of the solvent afforded pure salt 32 (100%).

Compound 33. To a solution of 20.1 mg of acid 25 (0.052 mmol) in THF was added 1 equivalent of triethanolamine dissolved in 200 µl of methanol and the mixture was stirred for 1 h. Evaporation of the solvent afforded pure salt 33 (100%).

Compound 34. To a solution of 20.1 mg of acid 25 (0.052 mmol) in THF was added 1 equivalent of diethanolamine dissolved in 200 µl of methanol and the mixture was stirred for 1 h. Evaporation of the solvent afforded pure salt 34 (100%).

Ester 35. Methyl (triphenylplphosphoranylidene) acetate (90.7 mg, 0.27 mmol) and aldehyde 9 (27.3 mg, 0.09 mmol) were dissolved in dried $CH_2Cl_2$ and stirred at room temperature. The reaction was completed within one day and then neutralized with $NH_4Cl$. Both trans and cis products were collected by the extraction with $CH_2Cl_2$. They were separated through the chromatography column. 24.4 mg and 2.5 mg of trans and cis ester were obtained and were separable by column chromatography (84% total yield). Trans 35: $^1$H-NMR ($CDCl_3$, 400 MHz) δ 7.00–6.92 (m, 1H), 5.96 (q, J=11.6 Hz, 1H), 5.80 (d, J=15.2 Hz, 1H), 4.47 (d, J=4.4 Hz, 1H), 5.00–4.96 (m, 2H), 3.72 (s, 3H), 2.45 (m, 1H), 2.35 (m, 1H), 1.08 (s, 3H), 1.06 (s, 3H), 0.89 (s, 1H); $^{13}$C-NMR ($CDCl_3$, 100 MHz) δ 18.82, 19.01, 19.90, 23.37, 24.97, 28.84, 35.94, 37.15, 37.22, 37.69, 37.85, 38.11, 40.98, 42.40, 46.55, 51.42, 112.38, 117.04, 122.38, 142.45, 148.03, 150.67, 166.73; $α_D$=−12.02. Cis: $^1$H-NMR ($CDCl_3$, 400 MHz) δ 6.32–6.25 (m, 1H), 5.97 (q, J=11.6 Hz, 1H), 5.83 (d, J=11.6 Hz, 1H), 5.47 (d, J=8 Hz, 1H), 5.00–4.96 (m, 2H), 3.71 (s, 3H), 3.19–3.13 (m, 1H), 2.61–2.55 (m, 1H), 1.15 (s, 3H), 1.07 (s, 3H), 0.90 (s, 3H).

Acid 36. 8 mg of trans ester 35 (0.023 mmol) and 2.70 mg of LiOH (0.113 mmol) were dissolved in 1 ml of $THF/H_2O$ (1:1). The reaction mixture was refluxed at 60° C. overnight. The completed reaction was neutralized with HCl (1M) and extracted with $CH_2Cl_2$. After the purification by chromatography column, 7.3 mg of pure product 36 was obtained (95%). 36: $^1$H-NMR ($CDCl_3$, 400 MHz) δ 7.12–7.04 (m, 1H), 5.96 (q, J=11.6 Hz, 1H), 5.82 (d, J=15.6 Hz, 1H), 5.48 (d, J=4.4 Hz, 1H), 5.01–4.97 (m, 2H), 2.53–2.46 (m, 1H), 2.23–2.19 (m, 1H), 1.09 (s, 3H), 1.07 (s, 3H), 0.88 (s, 3H); $^{13}$C-NMR ($CDCl_3$, 100 MHz) δ 38.12, 42.76, 42.93, 43.82, 47.29, 48.87, 48.91, 49.74, 52.77, 53.70, 60.01, 61.21, 61.64, 61.84, 62.05, 64.90, 66.35, 70.54, 136.46, 141.09, 141.19, 146.10; $α_D$=−15.17.

Ester 37. In a moisture-free flask, 5 mg of trans ester 35 (0.14 mmol) were dissolved in dry methanol. 1.7 mg Mg (0.07 mmol), which was freshly activated by heat, was added into the reaction flask. The reaction was stirred at room temperature overnight. When the reaction was done, the remaining Mg was dissolved by HCl (2M), and the mixture was then extracted with ether. 2.9 mg of yellow solid was obtained after the chromatography column (54% yield). 36: $^1$H-NMR ($CDCl_3$, 400 MHz) δ 5.96 (q, J=11.6 Hz, 1H), 5.45 (d, J=4 Hz, 1H), 5.00–4.95 (m, 2H), 3.67 9s, 3H), 2.27 (m, 2H), 1.25 (s, 3H), 1.05 (s, 3H), 0.83 (s, 3H); $^{13}$C-NMR ($CDCl_3$, 100 MHz) δ 18.59, 19.31, 19.99, 20.26, 23.44, 25.05, 26.16, 28.58, 29.81, 32.01, 35.25, 36.11, 37.3, 37.35, 37.75, 38.28, 41.41, 42.46, 46.94, 112.25, 116.75, 116.73, 142.60, 151.09; $α_D$=−22.1.

Acid 38. 5 mg of ester 37 (0.014 mmol) and 1.70 mg of LiOH (0.07 mmol) were dissolved in 1 ml of $THF/H_2O$ (1:1). The reaction mixture was refluxed at 65° C. overnight. The completed reaction was neutralized with HCl (1M) and extracted with $CH_2Cl_2$. After the purification by chromatography column, 3.9 mg of pure product 38 was obtained (81%). $^1$H-NMR ($CDCl_3$, 400 MHz) δ 5.96 (q, J=11.6 Hz, 1H), 5.45 (d, J=4 Hz, 1H0, 5.00–4.95 (m, 2H), 2.37 (m, 2H), 1.25 (s, 3H), 1.05 (s, 3H), 0.84 (s, 3H); $^3$C-NMR ($CDCl_3$, 100 MHz) δ 18.58, 19.28, 19.98, 23.42, 25.03, 26.12, 28.55, 29.79, 30.40, 31.94, 34.91, 36.09, 37.32, 37.73, 38.25, 41.38, 42.44, 46.93, 112.24, 116.73, 116.75, 142.55, 151.04; $α_D$=+3.4.

Example 24

The effects of seven different TTL3 analogs on viability and TNF-α synthesis of THP-1 cells was analyzed.

The ability to inhibit TNF-α production was analyzed in THP-1 cells, a human acute monocytic leukemia cell line that is widely used to assess monocyte functions. In order to induce maturation, THP-1 cells were plated at $1×10^6$ cells/ml and pretreated with 5 nM PMA for two days. Differentiated THP-1 cells were pretreated with various concentrations of NPI-1302a-3 or its analogs for 1 hour, followed by a 4 hour incubation with 1 μg of LPS (Sigma, St. Louse, Mo.). The P38 inhibitor (10 μM, SB 203580; Sigma, St. Louis, Mo.) was used as a positive control. Supernatants were collected and stored at −80° C. until assayed for TNF-α activity. A resazurin assay was performed for each analog to evaluate the effects on cell metabolism and viability.

A preparation of the dye resazurin, commercially-available as alamarBlue™ (Biosource International Inc., 820 Flynn Road, Camarillo, Calif.), was used for the cytotoxicity assays described herein. The assays and experiments described herein were conducted in substantially the same manner as described in the scientific literature, for example, in Magnani, E and Bettini, E., "Resazurin detection of energy metabolism changes in serum-starved PC12 cells and of neuroprotective agent effect," Brain Res Protoc., 2000 July;5(3):266–72 and in Nociari M. M., Shalev A., Benias P., and Russo C. J, "A novel one-step, highly sensitive fluorometric assay to evaluate cell-mediated cytotoxicity," Immunol. Methods 213, 157–167 (1998), see also U.S. Pat. No. 5,501,959, entitled "Antibiotic and Cytotoxic Drug Susceptibility Assays using Resazurin and Poising Agents," the entire specification of which is incorporated herein by reference.

To detect the presence of human TNFα, fluorescent linked immunosorbent assay or FLISA was developed and optimized. 100 μl of beads (6 μm, Spherotech) coated with goat anit-mouse IgG (1 mg/ml, R and D Systems) were mixed with 4 μl of biotin-anti-IgG hTNFα mouse IgG (0.1 mg/ml, R and D Systems) and 2 μl of FMAT Blue-streptavidin (0.1 mg/ml, Applied Biosystems). 50 μl of the mixtures was combined with 50 μl of the supernatant isolated from treated THP-1 cells and added to the black wall FLISA plates (Applied Biosystems) and incubated overnight. The plates were scanned at factory set PMT setting, and the values were plotted and analyzed by Applied Biosystems software.

Tables 10–23 also summarize the effects of seven TTL3 analog families on viability and TNF-α synthesis of THP-1 cells.

TABLE 1

Inhibition of LPS-Induced TNF-α Synthesis by the Compound of Formula (I) and TTL1

|  | LPS | Formula (I) (0.1 μg/ml) | Formula (I) (1 μg/ml) | Formula (I) (10 μg/ml) | TTL1 (0.1 μg/ml) | TTL1 (1 μg/ml) | TTL1 (5.4 μg/ml) |
|---|---|---|---|---|---|---|---|
| TNF-α (ng/ml) | 120 | 108 | 67 | 50 | 57 | 60 | 38 |

TABLE 2

Inhibition of SAC-Induced TNF-α Synthesis by the Compound of Formula (I) and TTL1

|  | SAC | Formula (I) (0.1 µg/ml) | Formula (I) (1 µg/ml) | Formula (I) (10 µg/ml) | TTL1 (0.1 µg/ml) | TTL1 (1 µg/ml) | TTL1 (5.4 µg/ml) |
|---|---|---|---|---|---|---|---|
| TNF-α (ng/ml) | 385 | 410 | 275 | 165 | 250 | 285 | 150 |

TABLE 3

Inhibition of SAC-Induced IL-1 Synthesis by the Compound of Formula (I) and TTL1

|  | SAC | Formula (I) (0.1 µg/ml) | Formula (I) (1 µg/ml) | Formula (I) (10 µg/ml) | TTL1 (0.1 µg/ml) | TTL1 (1 µg/ml) | TTL1 (5.4 µg/ml) |
|---|---|---|---|---|---|---|---|
| IL-1α (pg/ml) | 700 | 1350 | 1050 | 350 | 950 | 400 | 300 |

TABLE 4

The Compound of Formula (I) and TTL1 Do Not Inhibit SAC-Induced IL-6 Synthesis

|  | SAC | Formula (I) (0.1 µg/ml) | Formula (I) (1 µg/ml) | Formula (I) (10 µg/ml) | TTL1 (0.1 µg/ml) | TTL1 (1 µg/ml) | TTL1 (5.4 µg/ml) |
|---|---|---|---|---|---|---|---|
| IL-6 (ng/ml) | 75 | 65 | 90 | 80 | 83 | 86 | 65 |

TABLE 5

TTL3 Inhibits SAC-Induced TNF-α Synthesis

|  | Unstimulated | SAC | 0.001 µg/ml | 0.01 µg/ml | 0.1 µg/ml | 1 µg/ml | 10 µg/ml |
|---|---|---|---|---|---|---|---|
| TNF-α (ng/ml) | 5 | 375 | 80 | 75 | 85 | 60 | 80 |

TABLE 6

TTL3 Inhibits SAC-Induced IL-1 Synthesis

|  | Unstimulated | SAC | 0.001 µg/ml | 0.01 µg/ml | 0.1 µg/ml | 1 µg/ml | 10 µg/ml |
|---|---|---|---|---|---|---|---|
| IL-1α (pg/ml) | 0 | 650 | 200 | 220 | 190 | 180 | 170 |

TABLE 7

Inhibition of LPS-Induced TNF-α Synthesis by TTL3 (TNF-α (ng/ml))
LPS (1 µg/ml) + TTL3 (µg/ml)

| LPS alone | $(1 \times 10^{-7})$ | $(1 \times 10^{-6})$ | $(1 \times 10^{-5})$ | $(1 \times 10^{-4})$ | $(1.0)$ | $(1 \times 10^{2})$ |
|---|---|---|---|---|---|---|
| 88 | 41 | 18 | 10 | 15 | 13 | 4 |

TABLE 8

TTL3 Inhibits Mortality After LPS/D-Gal Administration

| Treatment* | Mortality 24 hours | Mortality 48 hours |
|---|---|---|
| LPS/D-Gal | 10/10 | 10/10 |
| LPS/D-Gal + DMSO | 8/10 | 9/10 |
| LPS/D-Gal + TTL3 | 2/10 | 2/10 |

*All treatments were i.p., TTL3 administration 45 minutes prior to LPS

TABLE 9

Assays Reflecting Examples 19–21

|  | Murine | | Human | |
|---|---|---|---|---|
|  | Dynamic Range (pg/ml) | Sensitivity (pg/ml) | Dynamic Range (pg/ml) | Sensitivity (pg/ml) |
| TNF-α | 15.63–1,000 | ≈15 | 8.19–800 | ≈10–15 |
| IL-1β | 15.63–1,000 | ≈20–30 | 3.28–800 | ≈4–5 |
| IL-1Ra | NT | NT | 8.19–800 | ≈10 |
| IL-6 | 15.63–1,000 | ≈15 | 8.19–800 | ≈10 |

TABLE 9-continued

Assays Reflecting Examples 19–21

| | Murine | | Human | |
|---|---|---|---|---|
| | Dynamic Range (pg/ml) | Sensitivity (pg/ml) | Dynamic Range (pg/ml) | Sensitivity (pg/ml) |
| IL-8 | Not Produced | Not Producted | 3.28–800 | ≈4–5 |
| IL-10 | 31.25–2,000 | ≈31 | 3.28–800 | ≈5–8 |
| IL-12 | 7.81–500 | ≈15 | 10–1,000 | ≈10 |

TABLE 10

The Effect of Series 1 Analogs on Cell Viability.

| Compound | 10 ug/ml | 1 ug/ml | 100 ng/ml |
|---|---|---|---|
| TTL-1 | 85* | 100 | 100 |
| NPI-1302a-3 | 100 | 100 | 100 |
| TTL-4 | 100 | 100 | 100 |
| TTL-7 | 100 | 100 | 100 |
| TTL-14 | NA | 100 | 100 |
| TTL-15 | 100 | 100 | 100 |
| LT-1-33 | 75** | 80* | 100 |
| LT-1-37 | 55** | 50** | NA |
| LT-1-39 | 80* | 100 | 100 |
| LT-1-45 | 90* | 100 | 100 |
| LT-4-32 | 100 | 100 | 100 |

*Mild reduction in viability
**Marked reduction in viability
NA: Data are not available

TABLE 11

Percent TNF-α Inhibition by Series 1 Analogs

| Compound | 10 ug/ml | 1 ug/ml | 100 ng/ml |
|---|---|---|---|
| TTL-1 | 50 | 30 | 10 |
| TTL-3 | 70 | 55 | 30 |
| TTL-4 | 0 | 0 | 0 |
| TTL-7 | 0 | 0 | 0 |
| TTL-14 | 45 | 30 | 25 |
| TTL-15 | 0 | 0 | 0 |
| LT-1-33 | 40 | 20 | 0 |
| I. LT-1-37 | 50 | 45 | 0 |
| II. LT-1-39 | 50 | 30 | 15 |
| LT-1-45 | 50 | 30 | 0 |
| LT-4-32 | 0 | 0 | 0 |

TABLE 12

The Effect of Series 2 Analogs on Cell Viability.

| Compound | 10 ug/ml | 1 ug/ml | 100 ng/ml |
|---|---|---|---|
| TTL-1 | 70** | 100 | 100 |
| TTL-1Na | 80* | 90* | NA |
| TTL-1K | NA | NA | NA |
| LT-1-43 | 90* | 100 | NA |
| LT-1-44 | 90* | 100 | NA |

TABLE 13

Percent TNF-α Inhibition by Series 2 Analogs

| Compound | 10 ug/ml | 1 ug/ml | 100 ng/ml |
|---|---|---|---|
| TTL-1 | 50 | 30 | 10 |
| TTL-1Na | 50 | 40 | NA |
| TTL-1K | NA | 50 | 10 |
| LT-1-43 | 20 | 10 | NA |
| LT-1-44 | 0 | 0 | 0 |

TABLE 14

The Effect of Series 3 Analogs on Cell Viability.

| Compound | 10 ug/ml | 1 ug/ml | 100 ng/ml |
|---|---|---|---|
| LT-1-73 | NA | 100 | 100 |
| LT-1-74 | NA | 100 | 100 |
| LT-1-78 | 100 | 100 | 100 |
| LT-1-83 | 70** | 100 | 100 |
| LT-1-85 | 80* | 100 | 100 |
| LT-1-89 | 100 | 100 | 100 |

TABLE 15

Percent TNF-α Inhibition by Series 3 Analogs.

| Compound | 10 ug/ml | 1 ug/ml | 100 ng/ml |
|---|---|---|---|
| LT-1-73 | 25 | 25 | 0 |
| LT-1-74 | NA | 30 | 25 |
| LT-1-78 | 20 | 0 | 0 |
| LT-1-83 | 50 | 0 | 0 |
| LT-1-85 | 55 | 45 | 10 |
| LT-1-89 | 20 | 10 | 10 |

TABLE 16

The Effect of Series 4 Analogs on Cell Viability.

| Compound | 10 ug/ml | 1 ug/ml | 100 ng/ml |
|---|---|---|---|
| LT-1-90 ra | 45** | 90* | 100 |
| CC-3-13 ra | 20** | 75** | 95* |
| CC-3-15 ra | 100 | 100 | NA |
| CC-3-19 P | 70** | 100 | 100 |
| CC-3-22 | 100 | 100 | 100 |
| CC-3-23 | 100 | 100 | 100 |

TABLE 17

Percent TNF-α Inhibition by Series 4 Analogs

| Compound | 10 ug/ml | 1 ug/ml | 100 ng/ml |
|---|---|---|---|
| LT-1-90 ra | NA | 50 | 0 |
| CC-3-13 ra | 95 | 50 | 10 |
| CC-3-15 ra | 65 | 25 | NA |
| CC-3-19 P | 50 | 0 | 0 |
| CC-3-22 | 20 | 0 | 0 |
| CC-3-23 | 0 | 0 | 0 |

TABLE 18

The Effect of Series 5 Analogs on Cell Viability.

| Compound | 10 ug/ml | 1 ug/ml | 100 ng/ml |
|---|---|---|---|
| LT-1-98 | 100 | 100 | 100 |
| LT-1-97 | 100 | 100 | 100 |

TABLE 18-continued

The Effect of Series 5 Analogs on Cell Viability.

| Compound | 10 ug/ml | 1 ug/ml | 100 ng/ml |
|---|---|---|---|
| LT-1-104 | 100 | 100 | 100 |
| CC-3-17 | 75** | 85* | 90* |
| CC-3-20 | 100 | 100 | 100 |
| CC-3-25 | 90* | 100 | 100 |
| CC-3-27 | 100 | 100 | 100 |

TABLE 19

Percent TNF-α Inhibition by Series 5 Analogs

| Compound | 10 ug/ml | 1 ug/ml | 100 ng/ml |
|---|---|---|---|
| LT-1-98 | 55 | 0 | 0 |
| LT-1-97 | 50 | 20 | 0 |
| LT-1-104 | 25 | 0 | 0 |
| CC-3-17 | 25 | 20 | 10 |
| CC-3-20 | 50 | 20 | 0 |
| CC-3-25 | 30 | 10 | 0 |
| CC-3-27 | 15 | 0 | 0 |

TABLE 20

The Effect of Series 6 Analogs on Cell Viability

| Compound | 10 ug/ml | 1 ug/ml | 100 ng/ml |
|---|---|---|---|
| CC-3-09 | 100 | 100 | 100 |
| CC-3-14 | NA | 100 | 100 |

TABLE 21

Percent TNF-α Inhibition by Series 6 Analogs

| Compound | 10 ug/ml | 1 ug/ml | 100 ng/ml |
|---|---|---|---|
| CC-3-09 | 10 | 0 | 0 |
| CC-3-14 | NA | 30 | 25 |

TABLE 22

The Effect of Series 7 Analogs on Cell Viability

| Compound | 10 ug/ml | 1 ug/ml | 100 ng/ml |
|---|---|---|---|
| LT-1-99 | 100 | 100 | 100 |
| LT-1-96 (trans) | 100 | 100 | 100 |
| LT-1-96 (cis) | 100 | 100 | 100 |
| LT-1-102 | 100 | 100 | 100 |
| CC-3-24 | 100 | 100 | 100 |
| CC-3-26 | 100 | 100 | 100 |
| CC-3-45 | 100 | 100 | 100 |
| LT-1-46 | 90* | 90* | 100 |
| CC-3-69 | NA | 100 | 100 |
| CC-3-21 | NA | 100 | 100 |

TABLE 23

Percent TNF-α inhibition by Series 7 Analogs 1

| Compound | 10 ug/ml | 1 ug/ml | 100 ng/ml |
|---|---|---|---|
| LT-1-99 | 50 | 50 | 20 |
| LT-1-96 (trans) | 50 | 0 | 0 |
| LT-1-96 (cis) | 50 | 0 | 0 |
| LT-1-102 | 0 | 0 | 0 |
| CC-3-24 | 55 | 25 | 0 |
| CC-3-26 | 20 | 0 | 0 |
| CC-3-45 | 0 | 0 | 0 |
| LT-1-46 | 20 | 0 | 0 |
| CC-3-69 | NA | 20 | 0 |
| CC-3-21 | NA | 0 | 0 |

While specific embodiments of the broadly diclosed invention have been shown and described in detail, and exemplified to illustrate the application of and the underlying principles of the invention, it will be understood by tbpose of skill in the art that the invention may be embodied otherwise without departing from such principles.

What is claimed is:

1. A compound having the following chemical structure:

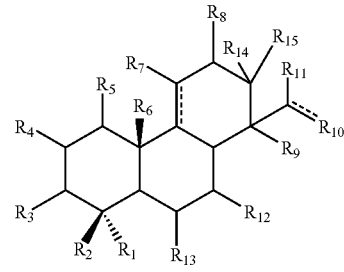

wherein:

$R_1$ is selected from the group consisting of hydrogen, a halogen, COOH, $C_1$–$C_{12}$ carboxylic acids, $C_1$–$C_{12}$ acyl halides, $C_1$–$C_{12}$ acyl residues, $C_1$–$C_{12}$ esters, $C_1$–$C_{12}$ secondary amides, $(C_1$–$C_{12})(C_1$–$C_{12})$ tertiary amides, $(C_1$—$C_{12})$ cyclic amides, $(C_1$–$C_{12})$ amines, $C_1$–$C_{12}$ alcohols, $(C_1$–$C_{12})(C_1$–$C_{12})$ ethers, $C_1$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls;

$R_2$ and $R_9$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, $C_1$–$C_{12}$ alcohol, $C_1$–$C_{12}$ acyl, and $C_5$–$C_{12}$ aryl;

$R_3$–$R_5$, $R_7$, $R_8$, and $R_1$–$R_{13}$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, and $C_5$–$C_{12}$ aryl;

$R_6$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, and $C_2$–$C_{12}$ alkynyl;

$R_{10}$ is selected from a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_{12}$ alcohol, and $C_5$–$C_{12}$ aryl; and $R_{14}$ and $R_{15}$ are separately selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_6$ alcohol, and $C_5$–$C_6$ aryl;

wherein the compound includes the prodrug esters of the above compounds, and the acid-addition salts thereof, and wherein both $R_1$ and $R_2$ are not simultaneously methyl.

2. The compound of claim 1, wherein:

$R_1$ is selected from hydrogen, a halogen, and $C_1$–$C_{12}$ carboxylic acids, $C_1$–$C_{12}$ acyl halides, $C_1$–$C_{12}$ acyl residues, $C_2$–$C_{12}$ esters, $C_2$–$C_{12}$ secondary amides, $(C_1$–$C_{12})(C_1$–$C_{12})$ tertiary amides, $C_2$–$C_{12}$ alcohols, $(C_1$–$C_{12})(C_1$–$C_{12})$ ethers, $C_2$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls.

3. The compound of claim 1, wherein:

$R_1$ is selected from the group consisting of hydrogen, a halogen, COOH, $C_1$–$C_6$ carboxylic acids, $C_1$–$C_6$ acyl halides, $C_1$–$C_6$ acyl residues, $C_1$–$C_6$ esters, $C_1$–$C_6$ secondary amides, $(C_1$–$C_6)(C_1$–$C_6)$ tertiary amides, $C_1$–$C_{12}$ cyclic amides, $C_1$–$C_{12}$ amines, $C_1$–$C_6$ alcohols, $(C_1$–$C_6)(C_1$–$C_6)$ ethers, $C_1$–$C_6$ alkyls, $C_1$–$C_{16}$ substituted alkyls, $C_2$–$C_6$ alkenyls, $C_2$–$C_{12}$ substituted alkenyls, and $C_5$–$C_6$ aryls.

4. The compound of claim 1, wherein $R_{10}$ is selected from the group consisting of $C_2$–$C_6$ alkyl groups and $C_2$–$C_6$ alkenyl groups.

5. The compound of claim 1, wherein $R_3$–$R_5$, $R_7$, $R_8$, $R_{11}$–$R_{15}$ is each hydrogen.

6. The compound of claim 5, wherein $R_3$–$R_5$, $R_7$, $R_8$, $R_{11}$–$R_{15}$ is each hydrogen; $R_2$, $R_6$, and $R_9$ are each methyl; and $R_{10}$ is $CH_2$.

7. The compound of claim 1, wherein $R_{15}$ is hydrogen, and $R_{14}$ is selected from hydrogen, a halogen, $C_1$–$C_{12}$ carboxylic acids, $C_1$–$C_{12}$ acyl halides, $C_1$–$C_{12}$ acyl residues, $C_2$–$C_{12}$ esters, $C_2$–$C_{12}$ secondary amides, $(C_1$–$C_{12})(C_1$–$C_{12})$ tertiary amides, $C_2$–$C_{12}$ alcohols, $(C_1$–$C_{12})(C_1$–$C_{12})$ ethers, $C_2$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls.

8. The compound of claim 1, wherein $R_{15}$ is hydrogen, and $R_{14}$ is selected from hydrogen, a halogen, $C_2$–$C_6$ alcohols, $C_2$–$C_6$ alkyls, $C_1$–$C_6$ substituted alkyls, $C_2$–$C_6$ alkenyls, $C_2$–$C_6$ substituted alkenyls, and $C_5$–$C_6$ aryls.

9. The compound of claim 1, wherein $R_1$ is $C_1$–$C_{12}$ secondary amide.

10. The compound of claim 9, wherein $R_{10}$ is selected from the group consisting of $C_2$–$C_6$ alkyl groups and $C_2$–$C_6$ alkenyl groups.

11. The compound of claim 9, wherein $R_3$–$R_5$, $R_7$, $R_8$, $R_{11}$–$R_{15}$ is each hydrogen.

12. The compound of claim 11, wherein $R_3$–$R_5$, $R_7$, $R_8$, $R_{11}$–$R_{15}$ is each hydrogen; $R_2$, $R_6$, and $R_9$ are each methyl; and $R_{10}$ is $CH_2$.

13. The compound of claim 9, wherein $R_{15}$ is hydrogen, and $R_{14}$ is selected from hydrogen, a halogen, $C_1$–$C_{12}$ carboxylic acids, $C_1$–$C_{12}$ acyl halides, $C_1$–$C_{12}$ acyl residues, $C_2$–$C_{12}$ esters, $C_2$–$C_{12}$ secondary amides, $(C_1$–$C_{12})(C_1$–$C_{12})$ tertiary amides, $C_2$–$C_{12}$ alcohols, $(C_1$–$C_{12})(C_1$–$C_{12})$ ethers, $C_2$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls.

14. The compound of claim 9, wherein $R_{15}$ is hydrogen, and $R_{14}$ is selected from hydrogen, a halogen, $C_2$–$C_6$ alcohols, $C_2$–$C_6$ alkyls, $C_1$–$C_6$ substituted alkyls, $C_2$–$C_6$ alkenyls, $C_2$–$C_6$ substituted alkenyls, and $C_5$–$C_6$ aryls.

15. A compound having the following chemical structure:

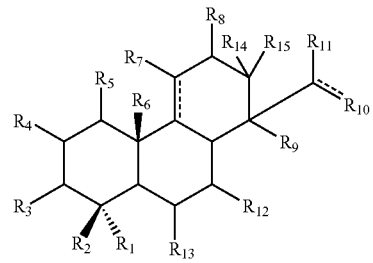

wherein:

$R_1$ is selected from the group consisting of hydrogen, a halogen, COOH, $C_1$–$C_{12}$ carboxylic acids, $C_1$–$C_{12}$ acyl halides, $C_1$–$C_{12}$ acyl residues, $C_1$–$C_{12}$ esters, $C_1$–$C_{12}$ secondary amides, $(C_1$–$C_{12})(C_1$–$C_{12})$ tertiary amides, $(C_1$–$C_{12})$ cyclic amides, $(C_1$–$C_{12})$ amines, $C_1$–$C_{12}$ alcohols, $(C_1$–$C_{12})(C_1$–$C_{12})$ ethers, $C_1$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls;

$R_2$ and $R_9$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, $C_1$–$C_{12}$ alcohol, $C_1$–$C_{12}$ acyl, and $C_5$–$C_{12}$ aryl;

$R_3$–$R_5$, $R_7$, $R_8$, and $R_{11}$–$R_{13}$ are each separately selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, $C_2$–$C_{12}$ alkynyl, and $C_5$–$C_{12}$ aryl;

$R_6$ is selected from hydrogen, a halogen, $C_1$–$C_{12}$ alkyl, $C_1$–$C_{12}$ substituted alkyls, $C_2$–$C_{12}$ alkenyl, $C_2$–$C_{12}$ substituted alkenyl, and $C_2$–$C_{12}$ alkynyl;

$R_{10}$ is selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_{12}$ alcohol, and $C_5$–$C_{12}$ aryl; and $R_{14}$ and $R_{15}$ are separately selected from hydrogen, a halogen, $CH_2$, $C_1$–$C_6$ alkyl, $C_1$–$C_6$ substituted alkyl, $C_2$–$C_6$ alkenyl, $C_2$–$C_6$ substituted alkenyl, $C_1$–$C_6$ alcohol, and $C_5$–$C_6$ aryl;

wherein the compound includes the prodrug esters of the above compounds, and the acid-addition salts thereof, and wherein both $R_1$ and $R_2$ are not simultaneously methyl.

16. The compound of claim 15, wherein:

$R_1$ is selected from hydrogen, a halogen, and $C_1$–$C_{12}$ carboxylic acids, $C_1$–$C_{12}$ acyl halides, $C_1$–$C_{12}$ acyl residues, $C_2$–$C_{12}$ esters, $C_2$–$C_{12}$ secondary amides, $(C_1$–$C_{12})(C_1$–$C_{12})$ tertiary amides, $C_2$–$C_{12}$ alcohols, $(C_1$–$C_{12})(C_1$–$C_{12})$ ethers, $C_2$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls.

17. The compound of claim 15, wherein:

$R_1$ is selected from the group consisting of hydrogen, a halogen, COOH, $C_1$–$C_6$ carboxylic acids, $C_1$–$C_6$ acyl halides, $C_1$–$C_6$ acyl residues, $C_1$–$C_6$ esters, $C_1$–$C_6$ secondary amides, $(C_1$–$C_6)(C_1$–$C_6)$ tertiary amides, $C_1$–$C_{12}$ cyclic amides, $C_1$–$C_{12}$ amines, $C_1$–$C_6$ alcohols, $(C_1$–$C_6)(C_1$–$C_6)$ ethers, $C_1$–$C_6$ alkyls, $C_1$–$C_{16}$ substituted alkyls, $C_2$–$C_6$ alkenyls, $C_2$–$C_{12}$ substituted alkenyls, and $C_5$–$C_6$ aryls.

18. The compound of claim 15, wherein $R_{10}$ is selected from the group consisting of $C_2$–$C_6$ alkyl groups and $C_2$–$C_6$ alkenyl groups.

19. The compound of claim 15, wherein $R_3$–$R_5$, $R_7$, $R_8$, $R_{11}$–$R_{15}$ is each hydrogen.

20. The compound of claim 19, wherein $R_3$–$R_5$, $R_7$, $R_8$, $R_{11}$–$R_{15}$ is each hydrogen; $R_2$, $R_6$, and $R_9$ are each methyl; and $R_{10}$ is $CH_2$.

21. The compound of claim 15, wherein $R_{15}$ is hydrogen, and $R_{14}$ is selected from hydrogen, a halogen, and $C_1$–$C_{12}$ carboxylic acids, $C_1$–$C_{12}$ acyl halides, $C_1$–$C_{12}$ acyl residues, $C_2$–$C_{12}$ esters, $C_2$–$C_{12}$ secondary amides, $(C_1$–$C_{12})(C_1$–$C_{12})$ tertiary amides, $C_2$–$C_{12}$ alcohols, $(C_1$–$C_{12})(C_1$–$C_{12})$ ethers, $C_2$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls.

22. The compound of claim 15, wherein $R_{15}$ is hydrogen, and $R_{14}$ is selected from hydrogen, a halogen, $C_2$–$C_6$ alcohols, $C_2$–$C_6$ alkyls, $C_1$–$C_6$ substituted alkyls, $C_2$–$C_6$ alkenyls, $C_2$–$C_6$ substituted alkenyls, and $C_5$–$C_6$ aryls.

23. The compound of claim 15, wherein $R_1$ is $C_1$–$C_{12}$ secondary amide.

24. The compound of claim 23, wherein $R_{10}$ is selected from the group consisting of $C_2$–$C_6$ alkyl groups and $C_2$–$C_6$ alkenyl groups.

25. The compound of claim 23, wherein $R_3$–$R_5$, $R_7$, $R_8$, $R_{11}$–$R_{15}$ is each hydrogen.

26. The compound of claim 25, wherein $R_3$–$R_5$, $R_7$, $R_8$, $R_{11}$–$R_{15}$ is each hydrogen; $R_2$, $R_6$, and $R_9$ are each methyl; and $R_{10}$ is $CH_2$.

27. The compound of claim 15, wherein $R_{15}$ is hydrogen, and $R_{14}$ is selected from hydrogen, a halogen, and $C_1$–$C_{12}$ carboxylic acids, $C_1$–$C_{12}$ acyl halides, $C_1$–$C_{12}$ acyl residues, $C_2$–$C_{12}$ esters, $C_2$–$C_{12}$ secondary amides, $(C_1$–$C_{12})(C_1$–$C_{12})$ tertiary amides, $C_2$–$C_{12}$ alcohols, $(C_1$–$C_{12})(C_1$–$C_{12})$ ethers, $C_2$–$C_{12}$ alkyls, $C_1$–$C_{12}$ substituted alkyls, $C_2$–$C_{12}$ alkenyls, $C_2$–$C_{12}$ substituted alkenyls, and $C_5$–$C_{12}$ aryls.

28. The compound of claim 15, wherein $R_{15}$ is hydrogen, and $R_{14}$ is selected from hydrogen, a halogen, $C_2$–$C_6$ alcohols, $C_2$–$C_6$ alkyls, $C_1$–$C_6$ substituted alkyls, $C_2$–$C_6$ alkenyls, $C_2$–$C_6$ substituted alkenyls, and $C_5$–$C_6$ aryls.

\* \* \* \* \*